US009185915B2

(12) United States Patent
Guilhabert-Goya et al.

(10) Patent No.: US 9,185,915 B2
(45) Date of Patent: Nov. 17, 2015

(54) **SANDPAPER MUTANTS OF *BACILLUS* AND METHODS OF THEIR USE TO ENHANCE PLANT GROWTH, PROMOTE PLANT HEALTH AND CONTROL DISEASES AND PESTS**

(75) Inventors: Magalie Guilhabert-Goya, Davis, CA (US); Sarah F. Hovinga, Sacramento, CA (US); Daniel M. Joo, Davis, CA (US); Jonathan S. Margolis, Davis, CA (US); Sarah J. Mills, Woodland, CA (US); Varghese Thomas, Davis, CA (US); Damian Curtis, Davis, CA (US); Reed Nate Royalty, Davis, CA (US); Roy Whitson, Fresno, CA (US)

(73) Assignee: Bayer CropScience LP, Research Triangle Park, NC (US)

(*) Notice: Subject to any disclaimer, the term of this patent is extended or adjusted under 35 U.S.C. 154(b) by 0 days.

(21) Appl. No.: 13/330,576

(22) Filed: Dec. 19, 2011

(65) Prior Publication Data
US 2012/0231951 A1    Sep. 13, 2012

Related U.S. Application Data

(60) Provisional application No. 61/425,742, filed on Dec. 21, 2010, provisional application No. 61/505,023, filed on Jul. 6, 2011, provisional application No. 61/511,522, filed on Jul. 25, 2011, provisional application No. 61/556,039, filed on Nov. 4, 2011.

(51) Int. Cl.
*C07K 14/32* (2006.01)
*A01N 63/00* (2006.01)

(52) U.S. Cl.
CPC ............... *A01N 63/00* (2013.01); *C07K 14/32* (2013.01)

(58) Field of Classification Search
None
See application file for complete search history.

(56) References Cited

U.S. PATENT DOCUMENTS

| | | | |
|---|---|---|---|
| 6,015,553 | A | 1/2000 | Germida et al. |
| 6,060,051 | A | 5/2000 | Heins et al. |
| 6,103,228 | A | 8/2000 | Heins et al. |
| 6,291,426 | B1 | 9/2001 | Heins et al. |
| 6,417,163 | B1 | 7/2002 | Heins et al. |
| 6,524,998 | B1 | 2/2003 | Kloepper et al. |
| 6,638,910 | B2 | 10/2003 | Heins et al. |
| 6,896,883 | B2 | 5/2005 | Bergstrom et al. |
| 2010/0064393 | A1 | 3/2010 | Berka et al. |
| 2011/0154544 | A1* | 6/2011 | Riggs ........................... 800/298 |
| 2014/0005047 | A1 | 1/2014 | Hungenberg et al. |

FOREIGN PATENT DOCUMENTS

| | | | |
|---|---|---|---|
| EP | 2460407 | A1 | 6/2012 |
| WO | WO 00/38510 | A1 | 7/2000 |
| WO | WO 00/42855 | A1 | 7/2000 |
| WO | WO 2007/104570 | A2 | 9/2007 |
| WO | WO 2008/152589 | A2 | 12/2008 |
| WO | WO2010030554 | A1 | 3/2010 |
| WO | 2010/128003 | A2 | 11/2010 |
| WO | WO2010128003 | A2 | 11/2010 |
| WO | WO20100128003 | A2 | 11/2010 |
| WO | WO2012087980 | A1 | 6/2012 |

OTHER PUBLICATIONS

Monograph—Bacillus subtilis strain QST 713, vol. 1, Rapporteur Member State: Germany, pp. 1-161, May 15, 2001.*
Bais, et al., "Biocontrol of Bacillus subtilis Against Infection of Arabidopsis Roots by Pseudomonas syringae is Facilitated by Biofilm Formation and Surfactin Production," Plant Physiol. (2004) 134:307-319.
Branda, et al., "Fruiting Body Formation by Bacillus subtilis," Proc. Natl. Acad. Sci. USA (2001) 98:11621-11626.
Calvio, et al., "Autoregulation of swrAA and Motility in Bacillus subtilis," Journal of Bacteriology (2008) 190:5720-5728.
Calvio et al., "Swarming Differentiation and Swimming Motility in Bacillus subtilis Are Controlled by swrA, a Newly Identified Dicistronic Operon," Journal of Bacteriology (2005) 187(15):5356-5366.
Chen et al., "Comparative analysis of the complete genome sequence of the plant growth-promoting bacterium Bacillus amyloliquefaciens FZB42," Nature Biotechnology (2007) 25(9):1007-1014.
Kearns et al., "Cell Population Heterogeneity During Growth of Bacillus subtilis," Genes & Development (2005) 19:3083-3094.
Kearns, et al., "Genes Governing Swarming in Bacillus subtilis and Evidence for a Phase Variation Mechanism Controlling Surface Motility," Molecular Microbiology (2004) 52(2):357-369.
Kloeper et al., "Induced systemic resistance and promotion of plant growth by Bacillus spp.," Phytopathology (2004) 94(11):1259-1266.
Lemon, et al., "Biofilm Development with an Emphasis on Bacillus subtilis," (2008) Current Topics in Microbiology and Immunology (2008) 322:1-16.
McLoon, A., et al., "Tracing the Domestication of a Biofilm-Forming Bacterium" Journal of Bacteriology, Apr. 2011 2027-2034.
Morikawa, "Beneficial biofilm formation by industrial bacteria Bacillus subtilis and Related Species," Journal of Bioscience and Bioengineering (2006) 101(1):1-8.
Osera et al., "SwrAA Activates Poly-•-glutamate Synthesis in Addition to Swarming in Bacillus subtilis," Microbiology (2009) 155, 2282-2287.
Patrick, J.E. and Kearns, D.B., "Laboratory Strains of Bacillus subtilis Do Not Exhibit Swarming Motility," Journal of Bacteriology (2009) 191(22): 7129-7133.
Rudrappa et al., "Causes and Consequences of Plant-Associated Biofilms," FEMS Microbiology Ecology (2008) 64:153-166.
Stanley, N. and Lazazzera, B., "Defining the Genetic Differences Between Wild and Domestic Strains of Bacillus subtilis that Affect Poly-•-DL-Glutamic Acid Production and Biofilm Formation," Molecular Microbiology (2005) 57(4): 1143-1158.

(Continued)

*Primary Examiner* — S. Devi
(74) *Attorney, Agent, or Firm* — Michelle L. Samonek; Adam L. Lunceford

(57) ABSTRACT

The present invention relates to novel strains of *Bacillus* and methods of their use for enhancing the growth, promoting plant health or controlling diseases or pests of a plant.

9 Claims, 39 Drawing Sheets

(56) References Cited

OTHER PUBLICATIONS

Calvio, C., et al., "Swarming Differentiation and Swimming Motility in Bacillus subtilis are Controlled by swrA, a Newly Identified Dicistronic Operon," Journal of Bacteriology, vol. 187, No. 15, Jul. 20, 2005, pp. 5356-5366.

Kearns, D.B., et al., "Genes Governing Swarming in Bacillus subtilis and Evidence for a Phase Variation Mechanism Controlling Surface Motility," Molecular Microbiology, vol. 52, No. 2, Apr. 1, 2004, pp. 357-369.

Merckling, T., et al., "Development of Serenade as a Biopesticide Against Plant Bacterial Diseases," Annual COST873 Meeting—Management Committee Meeting, Oct. 26, 2009, pp. 1-35.

Patrick, J.E., et al., "Laboratory Strains of Bacillus subtilis Do Not Exhibit Swarming Motility," Journal of Bacteriology, vol. 191, No. 22, Sep. 11, 2009, pp. 7129-7133.

Stanley, N.R., et al., "Defining the Genetic Differences Between Wild and Domestic Strains of Bacillus subtilis that Affect Poly-[gamma]-dl-glutamic Acid Production and Biofilm Formation," Molecular Microbiology, vol. 57, No. 4, Jul. 5, 2005, pp. 1143-1158.

"Review Report for the Active Substance Bacillus subtilis QST713", Jul. 14, 2006, pp. 1-24, Retrieved from the Internet: URL:http://ec.europa.eu/food/plant/protection/evaluation/newactive/bacillus_subtilis_report_final.pdf.

International Search Report and Written Opinion of the International Searching Authority, International Patent Application No. PCT/US2011/065936, Jun. 1, 2012, 19 pages.

Choudhary, D.K., et al, "Interactions of Bacillus spp, and plants—With special reference to induced systemic resistance (ISR)," Microbiological Research, vol. 64, No. 5, pp. 493-513, Sep. 29, 2009.

Dawar, S., et al., "Application of Bacillus Species in Control of Meloidogyne javanica (Treub) Chitwood on Cowpea and Mash Bean", Pak. J. Bot., 2008, 40:439-444.

Kokalis-Burelle, N., et al., "Field Evaluation of Plant Growth-Promoting Rhizobacteria Amended Transplant Mixes and Soil Solarization for Tomato and Pepper Production in Florida", Plant and Soil, 2002, 238:257-266.

Lian, L.H., et al., "Proteases from Bacillus: A New Insight into the Mechanism of Action for Rhizobacterial Suppression of Nematode Populations", Letters of Applied Microbiology, 2007, 45:262-269.

Lobna, M. & Zawam, H., "Efficacy of some Biocontrol Agents on Reproduction and Development of Meloidogyne incognita Infecting Tomato", Journal of American Science, 2010, 6:495-509.

Merckling, T., et al., "AgraQuest: Development of Serenade as a Biopesticide Against Plant Bacterial Diseases," Annual COST873 Meeting—Management Committee Meetign, 35 pages, Oct. 26, 2009.

Niknam, G.R., et al., "Induction of Systemic Resistance by Bacillus subtilis Isolate Bst Against Rotylenchulus Reniformis in Tomato," Nematologia Mediterranea, vol. 31, No. 2, pp. 239-243, Jan. 1, 2003.

Siddiqui, Z.A. & Akhtar, M.S., "Effects of Antagonistic Fungi, Plant Growth-Promoting Rhizobacteria, and Arbuscular Mycorrhizal Fungi Alone and in Combination on the Reproduction of Meloidogyne incognita and Growth of Tomato", J. Gen. Plant Pathol., 2009, 75:144-153.

Tariq, M. & Dawar, S., "Impact of Biocontrol Bacteria with Rhizophora mucronata Plant Parts in Suppression of Meloidogyne javanica (treub) Chitwood on Crop Plants", Archives of Phytopathology and Plant Protection, 2010, 43:754-760.

Tian, B., et al., "Bacteria Used in the Biological Control of Plant-Parasitic Nematodes: Populations, Mechanisms of Action, and Future Prospects", FEMS Microbiol. Ecol., 2007, 61:197-213.

AgraQuest "SERENADE® MAX" Product Sheet, available online Sep. 10, 2010.

International Search Report & Written Opinion of the International Searching Authority, PCT/US2012/047963, dated Nov. 23, 2012.

* cited by examiner

Figure 1
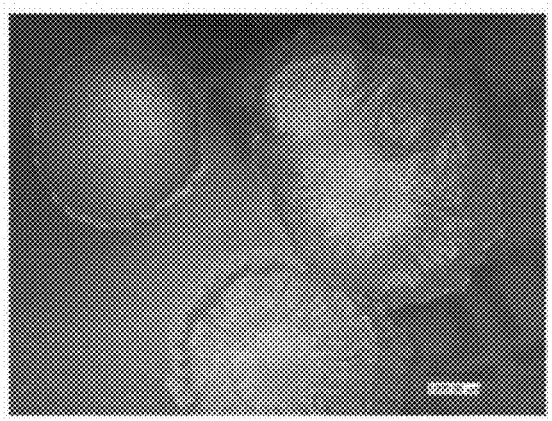
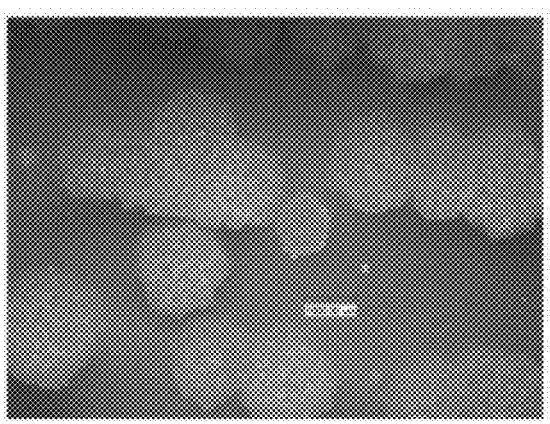
QST713 Wild-type          QST713 Sandpaper Variant

|  | Start codon change in AQ30004 ↓ | Deletion in AQ30002 ↓ | Insertion in *B. subtilis* 168 ↓ |

```
                                                                          60
QST713        TTGAAGAGGGCAAGTATTGTGCGTGAAAAAAAA-TATTATGAATTAGTGGAACAACTAAA
AQ30004       TTCAAGAGGGCAAGTATTGTGCGTGAAAAAAAA-TATTATGAATTAGTGGAACAACTAAA
AQ30002       TTGAAGAGGGCAAGTATTGTGCGTG-AAAAAAA-TATTATGAATTAGTGGAACAACTAAA
Bamy_FZB42    TTGAAGAGGGCAAGTATTGTGCGTGAAAAAAAA-TATTATGAATTAGTGGAACAACTAAA
Bsub_3610     TTGAAGAGGGCAAGTATTGTGCGTGAAAAAAAA-TATTATGAATTAGTGGAACAATTAAA
Bsub_168      TTGAAGAGGGCAAGTATTGTGCGTGAAAAAAAAATATTATGAATTAGTGGAACAATTAAA
Batr_1942     TTGAAGAGGGCAAGTATTGTGCGTGAAAAAAAA-TACTATGAATTAGTGGAACAATTAAA
Bpum_SAFR-032 TTGAAAAGGGCAAGTATTCTGAGAGAGAAAAAA-TATTACGAGTTGGTAGAGGAGCTTAA
Bpum_2808     TTGAAAAGGGCAAGTATTGTGAGAGAGAAAAAA-TATTACGAGTTGGTAGAGGAGCTTAA
              ** ** ************** ** *****  ** ** ** ** ** **    *  * **

120
QST713        AGACAGAACAAAAGACGTCACATTTTCATCAACAAAAGCACTAAGTCTTCTTATGCTGTT
AQ30004       AGACAGAACAAAAGACGTCACATTTTCATCAACAAAAGCACTAAGTCTTCTTATGCTGTT
AQ30002       AGACAGAACAAAAGACGTCACATTTTCATCAACAAAAGCACTAAGTCTTCTTATGCTGTT
Bamy_FZB42    AGACCGAACAAAAGACGTTACATTTTCATCAACAAAAGCACTAAGTCTTCTTATGCTGTT
Bsub_3610     AGACAGAACACAAGACGTAACATTTTCAGCTACAAAAGCACTAAGTCTTCTTATGCTGTT
Bsub_168      AGACAGAACACAAGACGTAACATTTTCAGCTACAAAAGCACTAAGTCTTCTTATGCTGTT
Batr_1942     AGACCGAACACAAGACGTAACATTTTCAGCTACAAAACCACTAAGTCTTCTAATGCTCTT
Bpum_SAFR-032 GAGTCGTACGAAAGATGTGACGTTTTCCGCTACAAAGGCATTAAGTCTGCTCATGCTGTT
Bpum_2808     GAGTCGTACGAAAGATGTGACGTTTTCGGCTACAAAGGCATTAAGTCTACTCATGCTGTT
               *  **   **** ** ** *****  * *****  *** *******   **  ***** **

180
QST713        CAGCAGATACCTGGTCAATTACACAAATGTTGAATGCGTTCACGAAATCAATGAAGAGTG
AQ30004       CAGCAGATACCTGGTCAATTACACAAATGTTGAATGCGTTCACGAAATCAATGAAGAGTG
AQ30002       CAGCAGATACCTGGTCAATTACACAAATGTTGAATGCGTTCACGAAATCAATGAAGAGTG
Bamy_FZB42    CAGCAGATACCTGGTCAATTACACAAATGTTGAATGTGTTCACGATATCAATGAGGAGTG
Bsub_3610     CAGCAGATATTTGGTCAATTACACCAATGTCGAATCAGTAAATGACATTAATGAGGAATG
Bsub_168      CAGCAGATATTTGGTCAATTACACCAATGTCGAATCACTAAATGACATTAATGAGGAATG
Batr_1942     TAGCAGATATTTAGTCAATTACACAAATGTAGAATCAGTGAACGATATTAATGAGGAATG
Bpum_SAFR-032 AAGCAGGTACTTGGTCAATTACACAACGGTAGAATCAGTCGACGAAATAGATGAAGACTG
Bpum_2808     AAGCAGGTACTTGGTCAATTACACAACGGTAGAATCAGTCGACGAGATCGATGAAGACTG
               *****  **   * ***********   **  ****    *   **  * ****  * **
                                                                         240
```

Figure 5B (continued)

```
QST713          TGCGAAGCATTATTTCACTTACTTAATGAAAAACCATAAACGTTTAGGAATTAATCTGAC
AQ30004         TGCGAAGCATTATTTCACTTACTTAATGAAAAACCATAAACGTTTAGGAATTAATCTGAC
AQ30002         TGCGAAGCATTATTTCACTTACTTAATGAAAAACCATAAACGTTTAGGAATTAATCTGAC
Bamy_FZB42      TGCAAAGCATTATTTCACCTACTTAATGAAAAACCATAAACGTTTAGGAATCAATCTGAC
Bsub_3610       CGCCAAACATTATTTTAACTACTTAATGAAAAACCATAAGCGATTAGGAATTAATCTGAC
Bsub_168        CGCCAAACATTATTTTAACTACTTAATGAAAAACCATAAGCGATTAGGAATTAATCTGAC
Batr_1942       CGCCGAGCATTATTTTAATTATTTAATGAAAAATCATAAACGGTTGGGAATCAATCTGAC
Bpum_SAFR-032   TGCTGAGATATACTTCAATTATTTAATGGATAATCATAAGAGACTTGGTATAAACTTAAC
Bpum_2808       TGCTGAGATATACTTCAATTATTTAATGGATAATCATAAGAGACTTGGTATAAACTTAAC
                 **  *     ** ** *   **  ******  *   ** *****    *   *  **  ** **     *  **
                                                                                     300
QST713          GGATATTAAGCGGTCCATGCTTCTGATCAGCGGCGTGATCGAGGTGGAGGTTGACCACTA
AQ30004         GGATATTAAGCGGTCCATGCTTCTGATCAGCGGCGTGATCGAGGTGGAGGTTGACCACTA
AQ30002         GGATATTAAGCGGTCCATGCTTCTGATCAGCGGCGTGATCGAGGTGGAGGTTGACCACTA
Bamy_FZB42      GGATATTAAACGGTCCATGCTTTTGATCAGCGGTGTAATCGAGGTGGAAGTCGACCACTA
Bsub_3610       AGATATAAAAGGTCGATGCATCTAATCAGCGGGTTATTGGATGTGGATGTAAACCACTA
Bsub_168        AGATATAAAAGGTCGATGCATCTAATCAGCGGGTTATTGGATGTGGATGTAAACCACTA
Batr_1942       AGACATAAAACGATCAATGCTCCTCATCGGCGGTGTGTTGGACGTCGAGGTAAACCATTA
Bpum_SAFR-032   CGACATCAAGAGATCGATGCAGCTGCTTGGCGGCATACTAGATGTAGATGTCAATCACTA
Bpum_2808       CGACATCAAGAGGTCCATGCAGCTTCTCGGCGGCATACTAGATGTAGATGTGAATCACTA
                 **   **  **     *  **   ****     *   *    ****    *     *  **   **  **  **     *    **   **
```

Figure 5C

```
                                                                              68
Bamy_QST713      MKRASIVREKKYYELVEQLKDRTKDVTFSSTKALSLLRLFSRYLVNYTRVECVREIREEC
Bamy_FZB42       MKRASIVREKKYYELVEQLKDRTKDVTFSSTKALSLLRLFSRYLVNYTRVECVRDINEEC
Bsub_3610        MKRASIVREKKYYELVEQLKDRTQDVTFSATKALSLLRLFSRYLVNYTRVESVRDINEEC
Batr_1942        MKRASIVREKKYYELVEQLKDRTQDVTFSATKALSLLRLFSRYLVNYTRVESVRDINEEC
Bpum_SAFR-032    MKRASIVREKKYYELVEELKSRTKDVTFSATKALSLLRLLSRYLVNYTTVESVREIDEDC
Bpum_7061        MKRASIVREKKYYELVEELKSRSKDVTFSATKALSLLRLLSRYLVNYTTVESVDEIDEDC
Blic_14580       MKRASIVREKKYYELVEQLKVRSQDVTFSATKAVCLLRLFSRYLVNYTSVESVRDINEDC
                 *****************::**  *::****:***:****:*******:**:*:*::**:*

117
Bamy_QST713      AKHYFTYLMKNHKRLGINLTDIKRSNLLISGVIEVEVDHYLKDFSLSNVTLNMTEER
Bamy_FZB42       AKHYFTYLMKNHKRLGINLTDIKRSNLLISGVIEVEVDHYLKDFSLSNVTLNMTEER
Bsub_3610        AKHYFNYLMKNHKRLGINLTDIKRSNLLISGLLDVDVRHYLKDFSLSNVTLNMTKER
Batr_1942        AKHYFNYLMKNHKRLGINLTDIKRSNLLISGVLDVDVRHYLKDFSLSNVTLNMSQER
Bpum_SAFR-032    AKIYFNYLMDNHKRLGINLTDIKRSNQLLGGILDVDVRHYLKDFSLSNVTLNMSQER
Bpum_7061        AKIYFNYLMDNHKRLGINLTDIKRSNQLLGGILDVDVRHYLKDFSLSNVTLNMSQER
Blic_14580       AKLYFNYLMDNHKRLGINLTDIKRSNQLIGGILDVEVRHYLKDFSLSNVTLNMSQER
                 *::**:***::************ *:::::*::*:*:**:****************: *:
```

SANDPAPER MUTANTS OF *BACILLUS* AND METHODS OF THEIR USE TO ENHANCE PLANT GROWTH, PROMOTE PLANT HEALTH AND CONTROL DISEASES AND PESTS

CROSS-REFERENCE TO RELATED APPLICATIONS

The present application claims priority to U.S. Provisional Patent Application No. 61/425,742, filed on Dec. 21, 2010; U.S. Provisional Patent Application No. 61/505,023, filed on Jul. 6, 2011; U.S. Provisional Patent Application No. 61/511,522, filed on Jul. 25, 2011; and U.S. Provisional Patent Application No. 61/556,039, filed on Nov. 4, 2011. Each of the foregoing applications is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 237-US_SeqList_ST25.txt, date recorded: Mar. 13, 2014, file size 24 kilobytes).

FIELD OF INVENTION

The present invention relates to the field of bacterial mutants and their ability to enhance plant growth, promote plant health and control plant diseases and pests.

BACKGROUND OF INVENTION

The *Bacillus* genus comprises numerous endospore-forming bacteria that have myriad uses in the agricultural and animal nutrition fields, among others. Several strains of *Bacillus* are currently marketed for use as plant growth promoters and/or biocontrol agents against insect pests and diseases (see, e.g., Masaaki Morikawa, "Beneficial Biofilm Formation by Industrial Bacteria *Bacillus subtilis* and Related Species," Journal of Bioscience and Bioengineering (2006) 101(1):1-8; Kloepper, et al., "Induced Systemic Resistance and Promotion of Plant Growth by *Bacillus* spp.," Phytopathology (2004) 94(11):1259-1266). These organic, environmentally-friendly alternatives have found wide-spread acceptance among agronomists and horticulturists due to their effectiveness as plant growth promoters and as biopesticides.

*Bacillus subtilis* is a Gram-positive soil bacterium, which is often found in the plant rhizosphere. *B. subtilis*, like many species of bacteria, can exhibit two distinct modes of growth, a free-swimming, planktonic mode of growth and a sessile biofilm mode in which an aggregate of cells secrete an extracellular matrix to adhere to each other and/or to a surface (Branda, et al., "Fruiting Body Formation by *Bacillus subtilis*," Proc. Natl. Acad. Sci. USA (2001) 98:11621-11626; Hamon and Lazazzera, "The Sporulation Transcription Factor Spo0A is Required for Biofilm Development in *Bacillus subtilis*," Mol. Microbiol. (2001) 52:847-860). The pathways utilized by bacteria such as *B. subtilis* to build biofilms are extremely diverse, varying enormously within and among different species and under different environment conditions (Bais, et al., "Biocontrol of *Bacillus subtilis* Against Infection of *Arabidopsis* Roots by *Pseudomonas syringae* is Facilitated by Biofilm Formation and Surfactin Production," Plant Physiol. (2004) 134:307-319; Lemon et al., "Biofilm Development with an Emphasis on *Bacillus subtilis*," (2008) Current Topics in Microbiology and Immunology (2008) 322:1-16). It has somewhat recently been recognized that biofilm formation by specific strains of *B. subtilis* and related species may help control infection caused by plant pathogens (Morikawa (2006), supra).

Biofilm morphology and chemical composition vary across species and strains. Mucoid colony morphology and production of γ-polyglutamic acid occurring in wild *Bacillus subtilis* strains has been correlated with enhanced biofilm formation, while flat, dry colony morphology occurring in domestic (or lab) strains has been correlated with decreased biofilm formation. See Stanley, N. and Lazazzera, B. "Defining the Genetic Differences Between Wild and Domestic Strains of *Bacillus subtilis* that Affect Poly-γ-DL-Glutamic Acid Production and Biofilm Formation," Molecular Microbiology (2005) 57(4): 1143-1158 at 1145. The Branda paper (supra, 2001) described deficiencies in biofilms with non-mucoid colony morphology, such as flat, small, dry colonies, which grew laterally and eventually fused with each other, leading to small colonies lacking aerial structures. The Stanley paper, however, described a hybrid *Bacillus subtilis* strain having a loss of function mutation in the swrA locus that formed flat, dry colonies and showed enhanced biofilm formation. (The hybrid strain was a congression-made combination of a domestic strain with the DNA from a wild strain that is responsible for mucoid colony morphology.) Applicants have found that wild *Bacillus* strains with reduction or loss of function mutations to the swrA locus produce flat, dry colonies that form robust biofilms and, further, that formulated fermentation products consisting of such cells enhance plant health, lead to more robust root colonization compared to strains containing the wild type swrA gene, and control plant diseases and pests, such as nematodes.

Commercial agriculture and home gardening would both benefit from the availability of different and improved sources of *Bacillus* strains for use in enhancing plant growth, promoting plant health, controlling plant pests and diseases and providing alternatives to chemical nematicides. The present invention provides a new class of such bacterial strains and improved methods of their use by manipulation of biofilm formation.

SUMMARY OF INVENTION

The present invention provides compositions comprising a variant of spore-forming bacteria where the variant has a mutation in the swrA gene that results in impaired swarming ability and enhanced plant health promotion and that may also cause the following characteristics compared to a strain containing a wildtype swrA gene: a sandpaper cell or colony morphology consisting of flat, dry, highly compacted, and very crispy cells or colonies; more robust root colonization; and/or formation of long chains of cells during early exponential phase in liquid culture. Such mutation is referred to herein as a swrA mutation and cells with such swrA mutation are swrA$^-$ cells.

In such compositions of variants of spore-forming bacteria, the swrA$^-$ cells comprise at least about 3.5% of the total cells in the composition and at least 70% of the swrA$^-$ cells are spores. The present invention further provides such compositions wherein the swrA$^-$ cells comprise at least 10% of the total cells in the composition, or comprise at least 50% of the total cells in the composition, or comprise 100% of the total cells in the composition. The present invention further provides such compositions wherein at least about 80%, at least about 85%, or at least about 90% of the swrA⁻ cells and/or of the total cells in the composition are spores.

In some embodiments, the spore-forming bacteria are from the genus *Bacillus*. In still others, they are from a *Bacillus* species within the *Bacillus subtilis* clade (see FIG. 6). In yet others, the species is selected from the group consisting of *B. pumilus, B. atrophaeus, B. amyloliquefaciens, B. subtilis* and *B. licheniformis*. In yet others, the *Bacillus* species is *Bacillus subtilis* QST713.

The present invention provides compositions comprising swrA⁻ cells, wherein the loss of swrA function can be the result of any mutation that disrupts, interferes with or otherwise adversely affects its function. Examples of such mutations include but are not limited to at least one nucleic acid base pair change in a start codon for swrA, and/or at least one nucleic acid base pair deletion in swrA, and/or at least one nucleic acid base pair insertion in swrA, and/or disruption of a swrA promoter or other control element of swrA, and/or any other genetic or genetic type event that causes loss of swrA function (e.g., transposons, over expression, dominant negative mutants, RNAi, antisense, knock-outs, knock-ins, etc.).

The present invention involves uses of and compositions comprising spore-forming bacterial cells having a mutation in a swrA ortholog wherein the mutation reduces swarming ability of the bacterial cells in comparison to isogenic bacterial cells not having the mutation. In one embodiment, the swarming ability is measured by growth on a non-liquid surface.

The spore-forming bacterial cells having the mutation in the swrA ortholog may be from a *Bacillus* species within the *Bacillus subtilis* clade. In one embodiment, the spore-forming bacterial cells are wild. In another, the *Bacillus* species is selected from the group consisting of *B. pumilus, B. atrophaeus, B. amyloliquefaciens, B. subtilis* and *B. licheniformis*.

The spore-forming bacterial cells having the mutation in the swrA ortholog have various characteristics compared to isogenic bacterial cells not having the mutation, including at least one of the following: (i) the formation of a more robust biofilm; (ii) a biofilm that is flat, dry and thick; and (iii) formation of long chains in liquid culture in response to shear forces (that create a highly turbulent environment).

In other embodiments, the more robust biofilm further comprises one or more of the following characteristics in comparison to isogenic cells not having the mutation: (i) vegetative cells having a diameter that is at least about 1.5 times greater, (ii) cells having an extra cell coat, (iii) a large white (electron transparent) region when visualized with a transmission electron microscope, (iv) the appearance of the biofilm of AQ30002 shown in FIG. 12, 13 or 14, and (v) cells that form long chains in liquid culture.

In one embodiment, the swrA ortholog has at least about 90% identity to a swrA wildtype gene of the same *Bacillus* species as the bacterial cells comprising the mutation. In another embodiment, the swrA ortholog has at least about 95% identity, at least about 96% identity, at least about 97% identity, at least about 98% identity, or at least about 99% identity to a swrA wildtype gene of the same *Bacillus* species as the bacterial cells having the mutation. In still another embodiment, the wildtype swrA gene with at least about 99% sequence identity to the swrA ortholog is from the same strain as the bacterial cells having the mutation. In still another embodiment the swrA ortholog has at least about 90% identity to any one of the swrA nucleotide sequences provided in SEQ ID NOS. 1 and 5-10.

In another embodiment the mutation in the swrA ortholog is at a position corresponding to one or more of positions 26-34 of the swrA gene set forth as SEQ ID NO. 1 or at a position corresponding to one or more of positions 1-3 of the swrA gene set forth as SEQ ID NO. 1. In one variation, the mutation is an insertion or deletion.

In one embodiment, the compositions of spore-forming bacterial cells described above comprise at least 3.5% of the total bacterial cells in the composition and/or at least about 70% of the spore-forming bacterial cells in the composition are spores.

In another embodiment, the invention encompasses compositions comprising spore-forming bacterial swrA⁻ cells, wherein the swrA⁻ cells comprise at least 3.5% of the total bacterial cells in the composition and/or wherein at least about 70% of the spore-forming bacterial cells are spores. In some embodiments, swrA activity has been reduced by means other than mutation of the swrA gene. swrA activity may be reduced by various agents, including small molecules, drugs, chemicals, compounds, siRNA, ribozymes, antisense oligonucleotides, swrA inhibitory antibodies, swrA inhibitory peptides, aptamers or mirror image aptamers. In one embodiment the mutation in the swrA gene in the swrA⁻ cells is at a position corresponding to one or more of positions 26-34 of the swrA gene set forth as SEQ ID NO. 1 or at a position corresponding to one or more of positions 1-3 of the swrA gene set forth as SEQ ID NO. 1. In one variation, the mutation is an insertion or deletion. In another aspect the swrA⁻ cells are the result of a knock-out of the swrA gene.

In one embodiment, the spore-forming bacterial cells of the present invention are *Bacillus subtilis* QST713 bacterial cells having a mutation in the swrA gene and compositions thereof. In one aspect, the *Bacillus subtilis* QST713 bacterial cells comprise at least one nucleic acid base pair change in a start codon and/or at least one nucleic acid base pair insertion or deletion in a swrA gene. In other aspects, the insertion or deletion in the swrA gene occurs at one or more of the base pairs at positions 26-34 of SEQ ID NO. 1. In yet another aspect, the swrA⁻ cells of *Bacillus subtilis* QST713 are selected from the group consisting of the strain AQ30002 (aka QST30002) and the strain AQ30004 (aka QST30004), deposited as Accession Numbers NRRL B-50421 and NRRL B-50455, respectively. In still another aspect of the invention, the *Bacillus subtilis* QST713 having the mutation in the swrA gene is wildtype for epsC, sfp and degQ. In another aspect the *Bacillus subtilis* QST713 having the mutation is otherwise isogenic to *Bacillus subtilis* QST713. In some embodiments, compositions of the *Bacillus subtilis* QST713 cells having the mutation comprise at least about 3.5% of the total bacterial cells in the composition.

The present invention provides compositions comprising one or more *B. subtilis* strains selected from the group consisting of AQ30002 (aka QST30002) and AQ30004 (aka QST30004), deposited as Accession Numbers NRRL B-50421 and NRRL B-50455, respectively.

In one embodiment, the spore-forming bacteria cells having the mutation in the swrA ortholog are from a *Bacillus* species within the *Bacillus subtilis* clade and comprise a wildtype sfp ortholog. In another embodiment, these bacterial cells further comprise a wildtype degQ ortholog and a wildtype epsC ortholog. In one aspect, the sfp ortholog, the degQ ortholog and the epsC ortholog each have at least about 90% sequence identity to a sfp gene, a degQ gene and a epsC gene, respectively, from any one of *B. pumilus, B. atrophaeus, B. amyloliquefaciens, B. subtilis* and *B. licheniformis, B. aerophilus, B. stratosphericus, B. safensis, B. altitudinus, B. vallismortis, B. halotolerans, B. mojavensis, B. sonorensis,* and *B. aerius*. In yet another aspect, the at least about 90% sequence identity is to the sfp gene, the degQ gene and the epsC gene of any one of *B. subtilis* strain 3610, *B. amyloliquefaciens* strain FZB42, *B. pumilus* SAFR-032, *B. lichenformis* strain 14580, or *B. atrophaeus* strain 1942. In still another aspect, the sfp ortholog has at least about 90% sequence identity to SEQ ID NO. 11, the epsC ortholog has at least about 90% sequence identity to SEQ ID NO. 12 and the degQ ortholog has at least about 90% sequence identity to SEQ ID NO. 13. In yet another aspect, the sequence identity described in this paragraph is at least about 95%, at least about 96%, at least about 97%, at least about 98%, or at least about 99%.

The present invention further provides any of the spore-forming bacteria or compositions of the present invention further comprising a formulation inert or other formulation ingredient, such as polysaccharides (starches, maltodextrins, methylcelluloses, proteins, such as whey protein, peptides, gums), sugars (lactose, trehalose, sucrose), lipids (lecithin, vegetable oils, mineral oils), salts (sodium chloride, calcium carbonate, sodium citrate), and silicates (clays, amorphous silica, fumed/precipitated silicas, silicate salts). In some embodiments, such as those in which the compositions are applied to soil, the compositions of the present invention comprise a carrier, such as water or a mineral or organic material such as peat that facilitates incorporation of the compositions into the soil. In some embodiments, such as those in which the composition is used for seed treatment or as a root dip, the carrier is a binder or sticker that facilitates adherence of the composition to the seed or root. In another embodiment in which the compositions are used as a seed treatment the formulation ingredient is a colorant. In other compositions, the formulation ingredient is a preservative.

The present invention further provides any of the compositions of the present invention further comprising at least one other active ingredient or agent in addition to the swrA⁻ cells. Such other active ingredients or agents can be a chemical or another strain of bacteria. Examples of suitable active ingredients or agents include but are not limited to an herbicide, a fungicide, a bactericide, an insecticide, a nematicide, a miticide, a plant growth regulator, a plant growth stimulant and a fertilizer.

The present invention further provides compositions wherein the swrA⁻ cells comprise from about $1\times10^2$ cfu/g to about $1\times10^{10}$ cfu/g in the composition. The present invention further provides such compositions wherein the swrA⁻ cells comprise at least $1\times10^6$ cfu/g, or comprise at least $1\times10^7$ cfu/g, or comprise at least $1\times10^8$ cfu/g, or comprise at least $1\times10^9$ cfu/g.

The present invention includes fermentation products of spore-forming bacteria of the present invention and compositions comprising such fermentation products. In one aspect, these fermentation products include spore-forming bacterial cells, their metabolites and residual fermentation broth. In other aspects, spore-forming bacterial cells of the fermentation product are largely spores. In another aspect, the compositions comprising fermentation products further comprise formulation inerts and formulation ingredients, as described herein. In some embodiments, the concentrated fermentation broth is washed, for example, via a diafiltration process, to remove residual fermentation broth and metabolites so that the fermentation product is largely spores.

The present invention also provides methods of treating a plant to enhance plant health (such as by promoting plant health, enhancing resistance to abiotic stress, or improving plant vigor) and/or control a plant disease and/or control a plant pest, wherein the method comprises applying one or more of the compositions of the present invention or the spore-forming bacteria of the present invention to the plant, to a part of the plant and/or to the locus surrounding the plant, such as to a plant's growth media. Thus, for example, the present invention further provides such methods wherein the compositions of the present invention are applied to the soil. For example, the composition can be applied before, during or after the plant or plant part comes into contact with the soil. As further examples, the methods of the present invention include but are not limited to applying the composition using an application method such as soil surface drench, shanking in, injection, chemigation or application in-furrow.

The methods of the present invention can be used on any plant part. Examples of such plant parts include but are not limited to the seed, root, corm, tuber, bulb, slip and rhizome.

Compositions and spore-forming bacteria of the present invention are useful to control plant parasitic nematodes, such as, for example, root-knot, cyst, lesion and ring nematodes, including *Meloidogyne* spp., *Heterodera* spp., *Globodera* spp., *Pratylenchus* spp. and *Criconemella* sp. In some embodiments, the targets are root knot nematodes, such as *M. incognita* (cotton root knot nematode), *M. javanica* (Javanese root knot nematode), *M. hapla* (Northern root knot nematode), and *M. arenaria* (peanut root knot nematode). In some embodiments symptoms and/or nematodes are reduced by at least about 5%, at least about 10%, at least about 20%, at least about, 30%, at least about 40%, at least about 50%, at least about 60%, at least about 70%, at least about 80%, or at least about 90%.

In another aspect, the uses, methods, spore-forming bacteria having a mutation in the swrA ortholog, and compositions described herein increase crop yield by about 10% to about 20%, about 10% to about 30%, about 10% to about 40%, about 10% to about 90%, about 20% to about 80%, about 30% to about 70%, about 40% to about 60%, or about 5% or more, about 10% or more, about 20% or more, about 30% or more, about 40% or more, about 50% or more, about 60% or more, about 70% or more, about 80% or more, or about 90% or more compared to an untreated plant, crop, fruit, or vegetable. In yet another aspect, the methods and compositions described herein increase crop yield by about 5%, about 10%, about 20%, about 30%, about 40%, about 50%, about 60% about 70%, about 80%, or about 90% compared to an untreated plant, crop, fruit, or vegetable.

Representative plants that can be treated using the compositions of the present invention include but are not limited to the following monocots and dicots: bulb vegetables; cereal grains (such as wheat, barley, rice); corn (maize), citrus fruits (such as grapefruit, lemon, and orange); cotton and other fiber crops; curcurbits; fruiting vegetables; leafy vegetables (such as celery, head and leaf lettuce, and spinach); legumes (such as soybeans, green beans, chick peas, lentils); oil seed crops; peanut; pome fruit (such as apple and pear); stone fruits (such as almond, pecan, and walnut); root vegetables; tuber vegetables; corm vegetables; tobacco, strawberry and other berries; cole crops (such as broccoli, cabbage); grape; plants used for biomass production (such as miscanthus, bamboo), pineapple; and flowering plants, bedding plants, and ornamentals (such as fern and hosta). Compositions of the present invention are also used to treat perennial plants, including plantation crops such as banana and coffee and those present in forests, parks or landscaping.

When used as a seed treatment, the compositions of the present invention are applied at a rate of about $1\times10^2$ to about $1\times10^9$ cfu/seed, depending on the size of the seed. In some embodiments, the application rate is $1\times10^3$ to about $1\times10^7$ cfu/seed.

When used as a soil treatment, the compositions and spore-forming bacterial cells of the present invention can be applied as a soil surface drench, shanked-in, injected and/or applied in-furrow or by mixture with irrigation water. The rate of application for drench soil treatments, which may be applied at planting, during or after seeding, or after transplanting and at any stage of plant growth, is about $4 \times 10^{11}$ to about $8 \times 10^{12}$ cfu per acre. In some embodiments, the rate of application is about $1 \times 10^{12}$ to about $6 \times 10^{12}$ cfu per acre. The rate of application for in-furrow treatments, applied at planting, is about $2.5 \times 10^{10}$ to about $5 \times 10^{11}$ cfu per 1000 row feet. In some embodiments, the rate of application is about $6 \times 10^{10}$ to about $4 \times 10^{11}$ cfu per 1000 row feet. Those of skill in the art will understand how to adjust rates for broadcast treatments (where applications are at a lower rate but made more often) and other less common soil treatments.

The compositions and spore-forming bacterial cells of the present invention may be mixed with other chemical and non-chemical additives, adjuvants and/or treatments, wherein such treatments include but are not limited to chemical and non-chemical fungicides, insecticides, miticides, nematicides, fertilizers, nutrients, minerals, auxins, growth stimulants and the like.

The present invention provides a substantially pure culture and/or a biologically pure culture of a sandpaper cell isolated from a mixture of different cell types. For example, the invention provides such substantially pure cultures and/or biologically pure cultures wherein the mixture of different cell types is QST713, deposited as NRRL Accession No. B21661. The present invention provides substantially pure cultures and/or biologically pure cultures of *B. subtilis* strain AQ30002 (aka QST30002) or AQ30004 (aka QST30004), deposited as Accession Nos. NRRL B-50421 and NRRL B-50455, respectively.

The present invention provides substantially pure cultures and/or biologically pure cultures of a *B. subtilis* strain having all of the physiological and morphological characteristics of *B. subtilis* strain AQ30002 (aka QST30002) or AQ30004 (aka QST30004), deposited as Accession Nos. NRRL B-50421 and NRRL B-50455, respectively.

The present invention also provides progeny of substantially pure cultures and/or biologically pure cultures of any of the cultures of the present invention, wherein the culture has all of the physiological and morphological characteristics of *B. subtilis* strain AQ30002 (aka QST30002) or AQ30004 (aka QST30004), deposited as Accession Nos. NRRL B-50421 and NRRL B-50455, respectively.

The present invention also provides compositions comprising a substantially pure culture and/or a biologically pure culture of one or more of the swrA⁻ cells of the present invention.

BRIEF DESCRIPTION OF THE DRAWINGS

FIG. 1 shows a comparison of colony morphologies in QST713 wild type and QST713 sandpaper variants grown on nutrient agar plates. In contrast to the wild type colonies, colony morphologies of sandpaper variants are highly compacted and highly hydrophobic.

FIG. 5A shows the alignment of various swrA genomic DNA encompassing the predicted swrA transcript. Bsub__168=*B. subtilis* strain 168 (SEQ ID NO: 28); Bsub__3610=*B. subtilis* strain 3610 (SEQ ID NO: 7); QST713=QST713 wild type (SEQ ID NO: 1); AQ30002 and AQ30004=representative strains of the present invention (SEQ ID NO: 3 and SEQ ID NO: 4, respectively); Bamy_FZB42=*B. amyloliquefaciens* strain FZB42 (SEQ ID NO: 5); Bpum_SAFR-032=*B. pumilus* strain SAFR-032 (SEQ ID NO: 6); and Blic__14580=*B. licheniformis* strain 14580 (SEQ ID NO: 10).

FIG. 5B shows the alignment of various swrA genomic DNA encompassing the predicted swrA transcript. QST713=QST713 wild type (SEQ ID NO: 29); AQ30002 and AQ30004=representative strains of the present invention (SEQ ID NO: 31 and SEQ ID NO: 30, respectively); Bamy FZB42=*B. amyloliquefaciens* strain FZB42 (SEQ ID NO: 32); Bsub__3610=*B. subtilis* strain 3610 (SEQ ID NO: 33); Bsub__168=*B. subtilis* strain 168 (SEQ ID NO: 34); Batr__1942=*B. atrophaeus* strain 1942 (SEQ ID NO: 35); Bpum_SAFR-032=*B. pumilus* strain SAFR-032 (SEQ ID NO: 36); Bpum__2808=*B. pumilus* 2808 (SEQ ID NO: 37).

FIG. 5C shows the alignment of various swrA proteins obtained from their predicted swrA transcripts. Bamy_QST713=QST713 wild type (SEQ ID NO: 2); Bamy_FZB42=*B. amyloliquefaciens* strain FZB42 (SEQ ID NO: 38); Bsub__3610=*B. subtilis* strain 3610 (SEQ ID NO: 39); Batr__1942=*B. atrophaeus* strain 1942 (SEQ ID NO: 40); Bpum_SAFR-032=*B. pumilus* strain SAFR-032 (SEQ ID NO: 41); Bpum__7061=*B. pumilus* 7061 (SEQ ID NO: 42); Blic__14580=*B. licheniformis* strain 14580 (SEQ ID NO: 43).

DETAILED DESCRIPTION OF INVENTION

Figure 2:
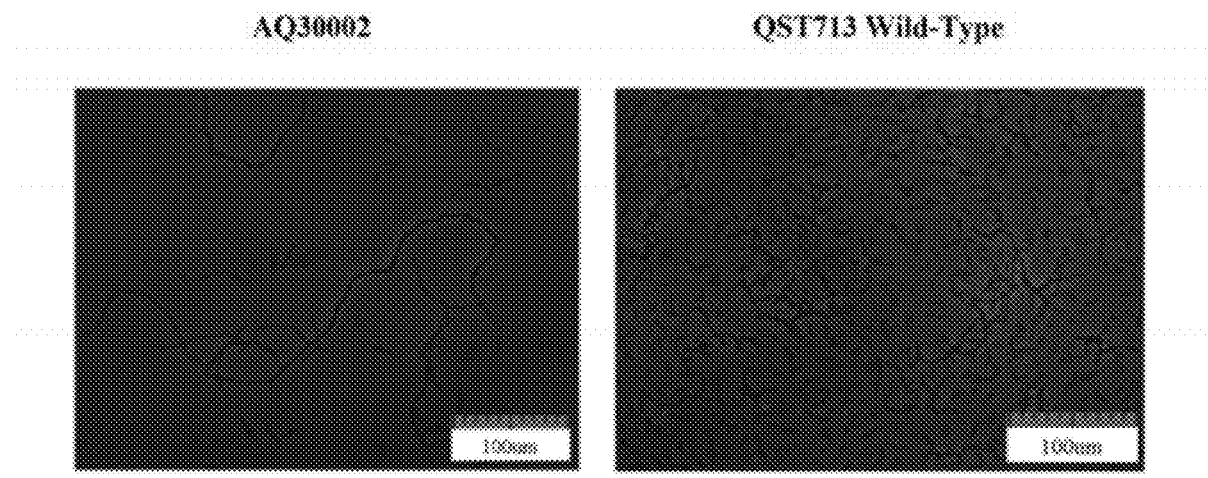
FIG. 2 shows images of AQ30002 swrA⁻ and QST713 wild type swrA⁺ cells during exponential growth phase in liquid culture.

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

The SERENADE® product (U.S. EPA Registration No. 69592-12) contains a unique, patented strain of *Bacillus subtilis* (strain QST713) and many different lipopeptides that work synergistically to destroy disease pathogens and provide superior antimicrobial activity. The SERENADE® product is used to protect plants such as vegetables, fruit, nut and vine crops against diseases such as Fire Blight, Botrytis, Sour Rot, Rust, Sclerotinia, Powdery Mildew, Bacterial Spot and White Mold. The SERENADE® products are available as either liquid or dry formulations which can be applied as a foliar and/or soil treatment. Copies of U.S. EPA Master Labels for SERENADE® products, including SERENADE® ASO, SERENADE® MAX, and SERENADE® SOIL, are publicly available through National Pesticide Information Retrieval System's (NPIRS®) USEPA/OPP Pesticide Product Label System (PPLS).

SERENADE® ASO (Aqueous Suspension-Organic) contains 1.34% of dried QST713 as an active ingredient and 98.66% of other ingredients. SERENADE® ASO is formulated to contain a minimum of $1 \times 10^9$ cfu/g of QST713 while the maximum amount of QST713 has been determined to be $3.3 \times 10^{10}$ cfu/g. Alternate commercial names for SERENADE® ASO include SERENADE® BIOFUNGICIDE, SERENADE® SOIL and SERENADE® GARDEN DISEASE. For further information, see the U.S. EPA Master Labels for SERENADE® ASO dated Jan. 4, 2010, and SERENADE® SOIL, each of which is incorporated by reference herein in its entirety.

SERENADE® MAX contains 14.6% of dried QST713 as an active ingredient and 85.4% of other ingredients. SERENADE® MAX is formulated to contain a minimum of $7.3 \times 10^9$ cfu/g of QST713 while the maximum amount of QST713 has been determined to be $7.9 \times 10^{10}$ cfu/g. For further information, see the U.S. EPA Master Label for SERENADE® MAX, which is incorporated by reference herein in its entirety.

Wild type *Bacillus subtilis* QST713, its mutants, its supernatants, and its lipopeptide metabolites, and methods for their use to control plant pathogens and insects are fully described in U.S. Pat. Nos. 6,060,051; 6,103,228; 6,291,426; 6,417,163; and 6,638,910; each of which is specifically and entirely incorporated by reference herein for everything it teaches. In these U.S. Patents, the strain is referred to as AQ713, which is synonymous with QST713. *Bacillus subtilis* QST713 has been deposited with the NRRL on May 7, 1997 under the provisions of the Budapest Treaty on the International Recognition of the Deposit of Microorganisms for the Purpose of Patent Procedure under Accession Number B21661. Any references in this specification to QST713 refer to *Bacillus subtilis* QST713 (aka AQ713) as present in the SERENADE® products, deposited under NRRL Accession No. B21661, or prepared in bioreactors under conditions that simulate production of the SERENADE® product.

At the time of filing U.S. patent application Ser. No. 09/074,870 in 1998, which corresponds to the above patents, the strain was designated as *Bacillus subtilis* based on classical, physiological, biochemical and morphological methods. Taxonomy of the *Bacillus* species has evolved since then, especially in light of advances in genetics and sequencing technologies, such that species designation is based largely on DNA sequence rather than the methods used in 1998. After aligning protein sequences from *B. amyloliquefaciens* FZB42, *B. subtilis* 168 and QST713, approximately 95% of proteins found in *B. amyloliquefaciens* FZB42 are 85% or greater identical to proteins found in QST713; whereas only 35% of proteins in *B. subtilis* 168 are 85% or greater identical to proteins in QST713. However, even with the greater reliance on genetics, there is still taxonomic ambiguity in the relevant scientific literature and regulatory documents, reflecting the evolving understanding of *Bacillus* taxonomy over the past 15 years. For example, a pesticidal product based on *B. subtilis* strain FZB24, which is as closely related to QST 713 as FZB42, is classified in documents of the U.S. EPA as *B. subtilis* var. *amyloliquefaciens*. Due to these complexities in nomenclature, this particular *Bacillus* species is variously designated, depending on the document, as *B. subtilis*, *B. amyloliquefaciens*, and *B. subtilis* var. *amyloliquefaciens*. Therefore, we have retained the *B. subtilis* designation of QST713 rather than changing it to *B. amyloliquefaciens*, as would be expected currently based solely on sequence comparison and inferred taxonomy.

Figure 4:
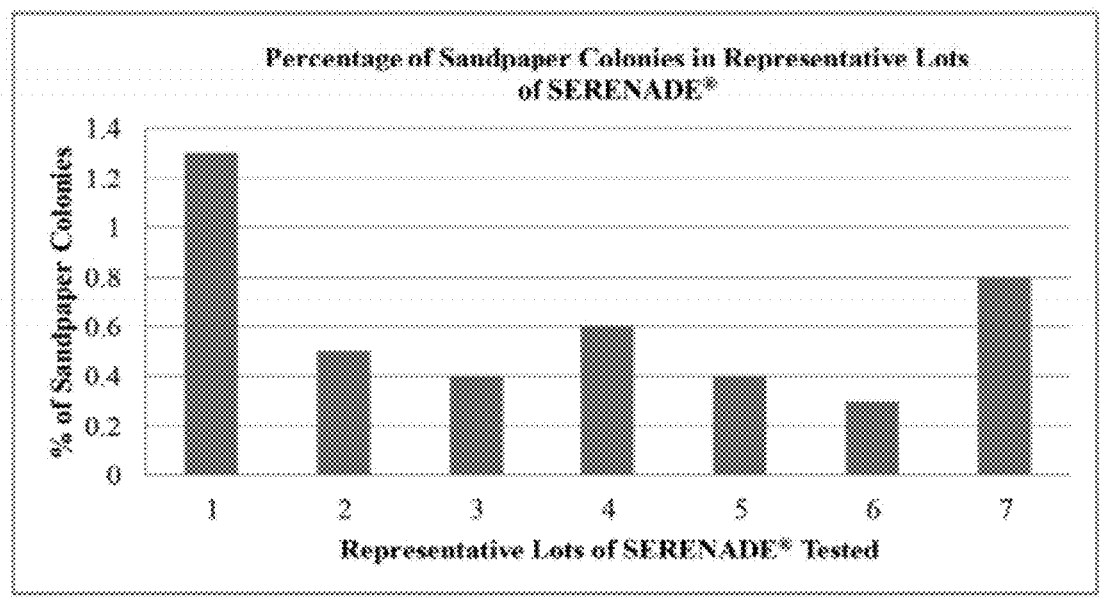
FIG. 4 shows quantification of sandpaper colonies in representative commercial batches of SERENADE® ASO.
Figure 12:
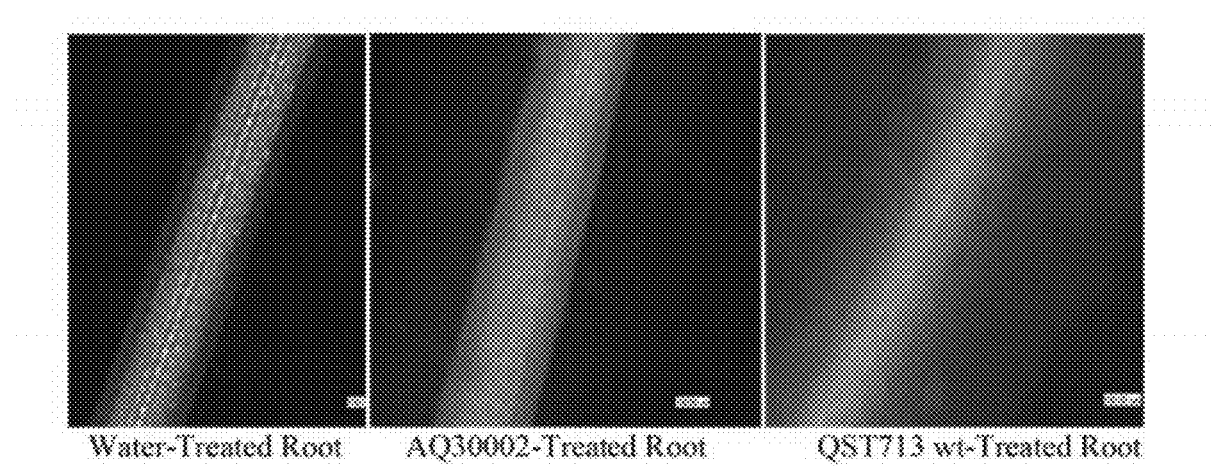
FIG. 12 shows images of root colonization with *Bacillus subtilis* AQ30002 swrA⁻ ("AQ30002") and QST713 wild type swrA⁺ ("QST713 wt").
Figure 13:
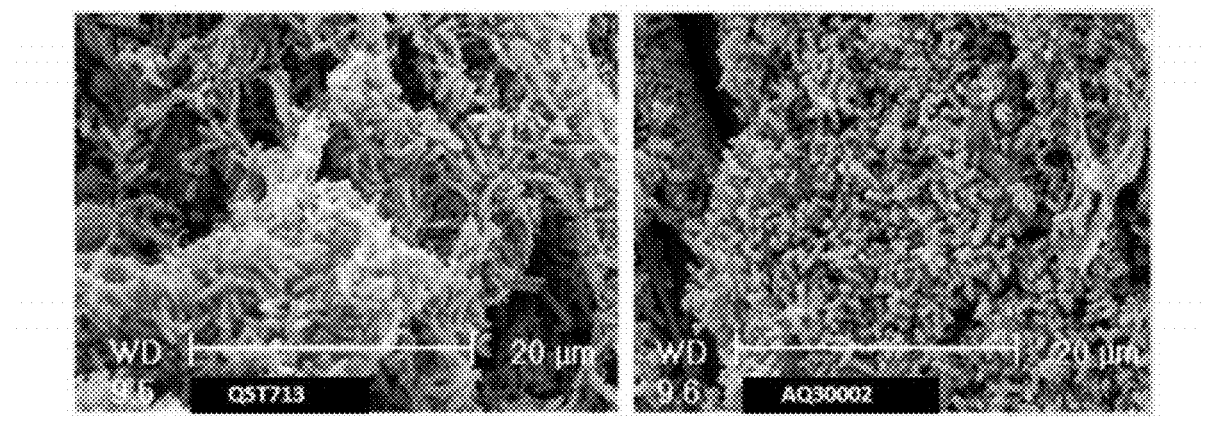
FIG. 13 shows scanning electron microscope (SEM) images of *Bacillus subtilis* QST713 wild type swrA+ ("QST713") and AQ30002 swrA− ("AQ30002") biofilms coating root surfaces.
Figure 14:
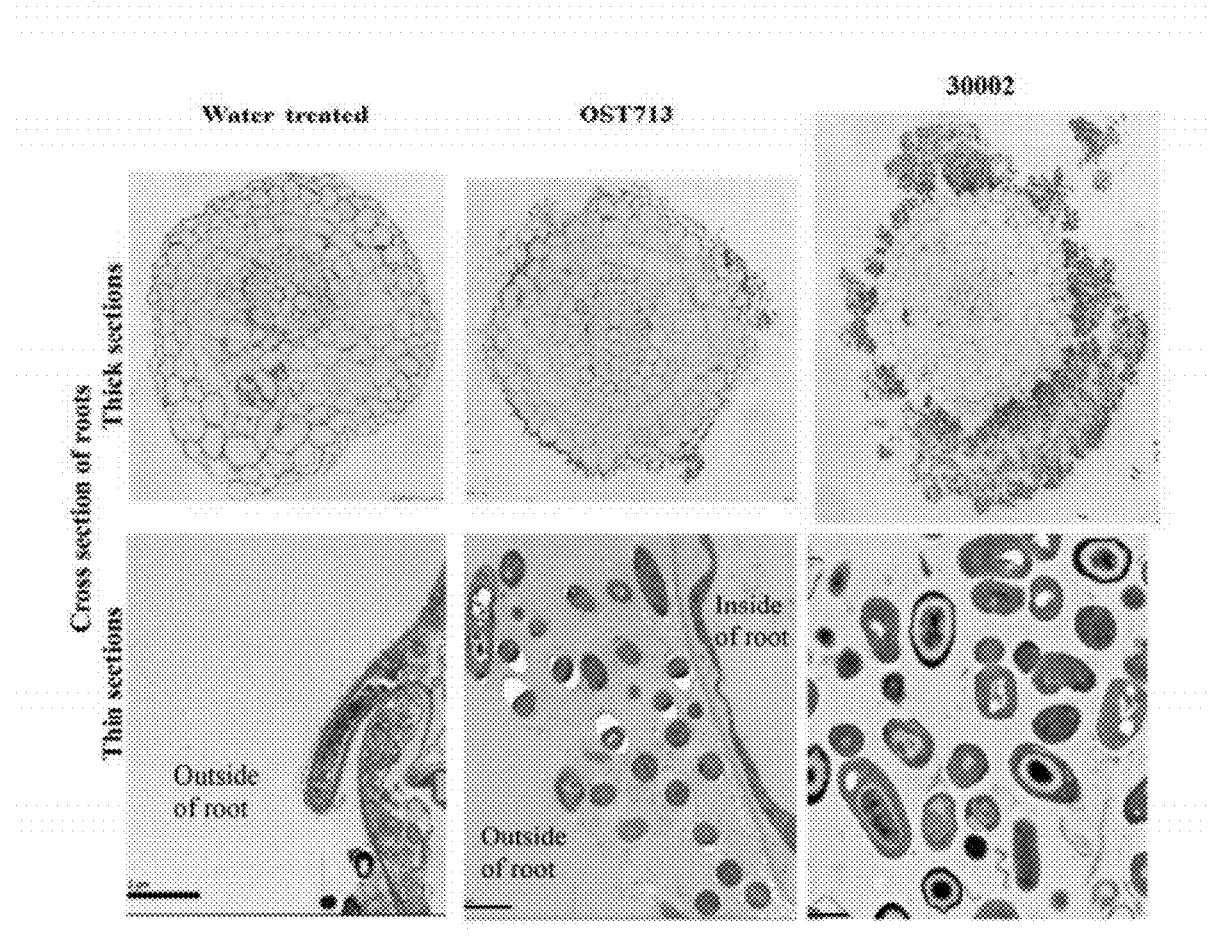
FIG. 14 shows light microscopy images of thin and thick sections of roots treated with water, *Bacillus subtilis* QST713 wild type swrA+ ("QST713") and AQ30002 swrA− ("30002").

As explained in greater detail herein, as a result of the instant invention, we now know that cultures of QST713 are actually a mixture of wild type cells and a relatively small percentage of variant cell types which we designated as "sandpaper cells." Thus, based on the instant invention, we now know QST713 as found in the SERENADE® products or as found in QST713 cells grown in a bioreactor consists of a mixed population of wild type cells and sandpaper cells at the same or similar ratios found in the SERENADE® product (see, e.g., FIG. 4). As described in detail herein, we refer to the variants as "sandpaper" cells based on the morphology of their colonies, as shown in FIG. 1. Sandpaper cells form colonies on nutrient agar that morphologically and physiologically appear highly compacted, hydrophobic, flat, dry, and very "crispy" and are very hard to remove from the agar. Cell adherence may be observed qualitatively or may be measured by the crystal violet staining described in Stanley, et al., supra. In addition to this distinct colony morphology on nutrient agar, sandpaper cells form dense, compact biofilms (or more robust biofilms) on surfaces such as roots, as shown in the images or 30002-treated roots in FIGS. 12, 13 and 14. In one embodiment the sandpaper cells have enhanced pellicle robustness, as may be tested as described in Example 8. In another embodiment, sandpaper cells form long chains of cells in addition to some single cells and shorter chains in liquid culture during early exponential phase, as shown in FIG. 2, but do not clump or form biofilms in liquid culture. In yet another embodiment, sandpaper cells show enhanced biofilm development, starting to form biofilms in response to shear forces even in liquid culture. In still another embodiment, sandpaper cells have an extra cell coat, as described in Example 9 and shown in the image of 30002-colonized roots in FIG. 14. In one embodiment, observations are based on comparisons to isogenic cells that are wildtype for the swrA gene. In another embodiment, observations on based on comparisons to cells of the same species that are wildtype for the genes or orthologs thereof required for biofilm formation; namely, sfp, swrA, epsC, and degQ. The term "isogenic" as used herein refers to any two cells or individuals (e.g., strains) having the same genotype. Based on the instant invention, we now know QST713 as found in the SERENADE® product (see, e.g., Example 1, FIG. 1 and FIG. 2) or as found in QST713 cells grown in a bioreactor consists of a mixed population of wild type cells and sandpaper cells at the same or similar ratios found in SERENADE® (see, e.g., Example 3 and FIG. 4).

Swarming motility is an active mechanism that enables bacteria to travel rapidly and en masse atop solid surfaces (J. Henrichsen, "Bacterial Surface Translocation: A Survey and a Classification," Bacteriol. Rev. (1972) 36:478-503). A number of different genes and operons have been associated with the ability to swarm in *Bacillus*. Kearns, et al. ("Genes Governing Swarming in *Bacillus subtilis* and Evidence for a Phase Variation Mechanism Controlling Surface Motility," Molecular Microbiology (2004) 52(2): 357-369) discovered that laboratory strain 168 and related laboratory strain PY79 of *B. subtilis* each have a frameshift mutation in a gene that they designated swrA that leads to impairment in swarming motility. Alternative names for swrA in the scientific literature include yvzd and swrAA. The swrA mutation (i.e., swrA⁻) in these two laboratory strains is an insertion of an A:T base pair in a homopolymeric stretch of eight A:T base pairs at nucleotide 34 (all numbering of swrA nucleotide sequences is with respect to our numbering in FIG. 5). This insertion is predicted to disrupt gene function by causing a frame shift mutation and truncated protein. The wild-type (functional; i.e., swrA⁺) sequence (i.e., without the insertion) was found in the undomesticated strain 3610 and in strains that had regained the capacity to swarm. Applicants established that the sandpaper cells of QST713 have a mutation in the swrA gene, as discussed in detail in Example 5. These swrA⁻ cells have impaired swarming ability. Surprisingly, when applied to plants or soil, they enhance plant health.

Other genes, sfp, epsC, swrA, degQ and a plasmid gene called rapP, are also involved in biofilm formation. See, McLoon, A., et al., "Tracing the Domestication of a Biofilm-Forming Bacterium" *Journal of Bacteriology*, April 2011 2027-2034. The domestic *Bacillus subtilis* strain designated as "168" forms an impaired biofilm with smooth, thin colonies and does not have the ability to swarm. The term "domestic," as used herein to describe bacterial strains, refers to derived, mutant strains selected for properties making them suitable for laboratory study, e.g., high competency to import and integrate genetic material, auxotrophy, lack of swarming or pellicle formation. In contrast, the term "wild," as used herein to describe bacterial strains, refers to strains that have been isolated from nature and that have not been actively selected for easy laboratory manipulation. The McLoon paper describes experiments conducted to repair the biofilm formation and swarming abilities of strain 168. First the sfp mutation was repaired, then the epsC mutation, then the swrA mutation and then the degQ mutation. At each step biofilm formation was progressively restored, becoming almost equivalent to biofilm formation in the wildtype *Bacillus subtilis* strain designated as 3610. Finally, the rapP gene on a plasmid was inserted into the otherwise fully repaired strain resulting in biofilm formation that was indistinguishable from that of 3610. McLoon, et al., state on page 2032, "We conclude that a strain carrying wild-type alleles of sfp, epsC and swrA is more robust in biofilm formation than a corresponding stain that is mutant for swrA and hence that swrA also contributes to robust biofilm formation." Surprisingly, according to the present invention, a strain that lacks swrA function forms a more robust biofilm than the parental strain having a wildtype swrA, in contrast to the finding in McLoon. McLoon, et al., do not describe a cell in which the only mutant biofilm forming gene is swrA, and, therefore, do not describe the enhanced biofilm phenotype described herein.

"Wild type" refers to the phenotype of the typical form of a species as it occurs in nature and/or as it occurs in a known isolated form which has been designated as the "wild type." Synonyms for "wild type" recognized herein include "wildtype," "wild-type," "+" and "wt". The wild type is generally conceptualized as a product of the standard, "normal" allele of a specific gene(s) at one or more loci, in contrast to that produced by a non-standard, "mutant" or "variant" allele. In general, and as used herein, the most prevalent allele (i.e., the one with the highest gene frequency) of a particular *Bacillus* strain or isolate is the one deemed as the wild type. As used herein, "QST713 wild type" or "QST713 wild type swrA⁺" and synonyms thereof (e.g., "QST713 swrA⁺, "QST wild-type," "QST713 wt," etc.) refer to *B. subtilis* QST713 with a functional swrA gene (i.e., swrA⁺) that is able to express the encoded swrA protein. Thus, these terms refer to clonal wild type QST713 cells which are 100% swrA⁺. Wildtype QST713 is also wildtype (i.e., bears functional copies) for other genes identified in the literature as related to biofilm formation: epsC, degQ, and sfp. SEQ ID NO. 11 is the nucleotide sequence for the sfp gene in wildtype QST713. SEQ ID NO. 12 is the nucleotide sequence for the epsC gene in wildtype QST713. SEQ ID NO. 13 is the nucleotide sequence for the degQ gene in wildtype QST713.

The microorganisms and particular strains described herein, unless specifically noted otherwise, are all separated from nature and grown under artificial conditions, such as in cultures or through scaled-up manufacturing processes, such as fermentation, described herein.

Figure 5A:
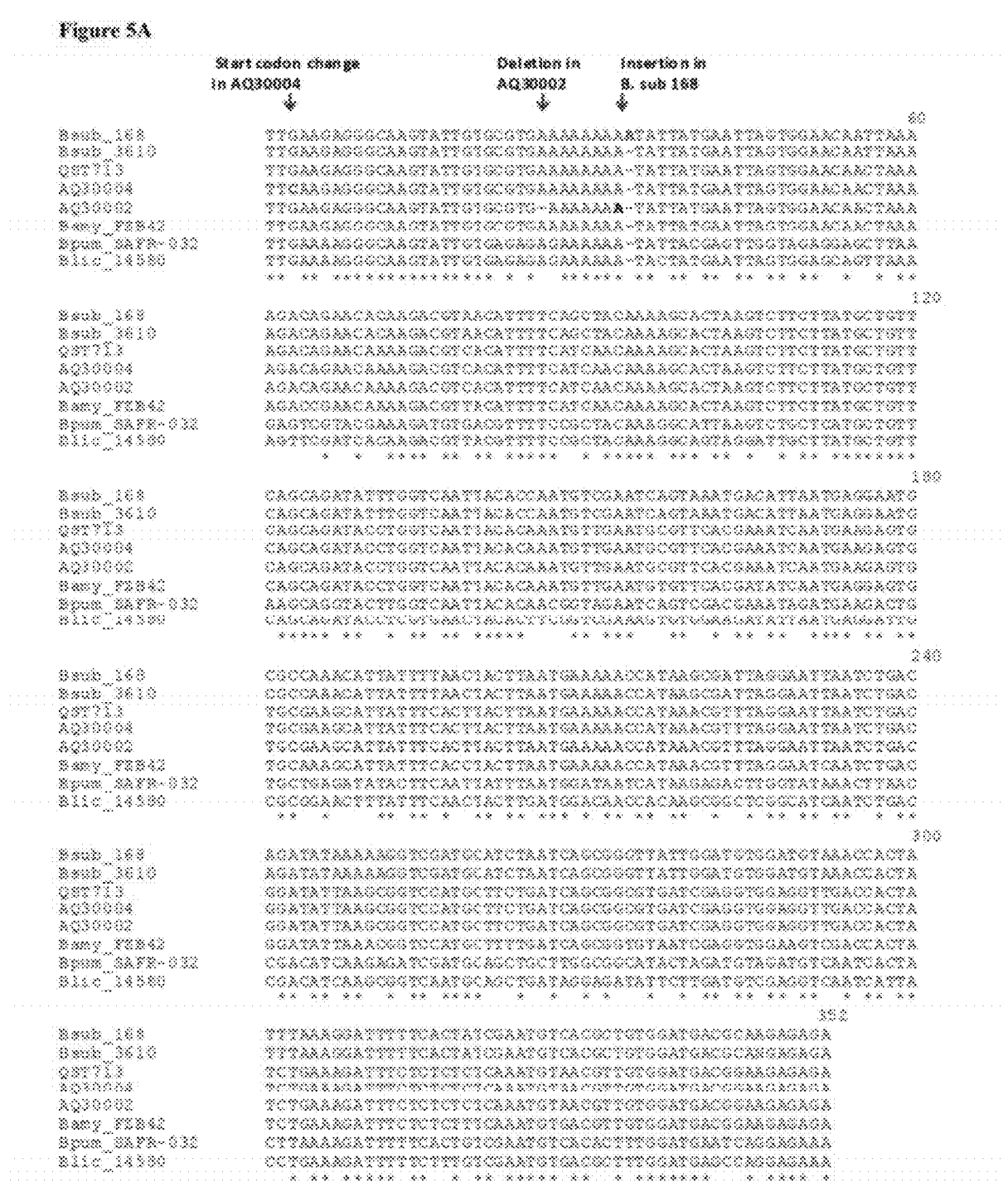

The sequence listing provided with this application provides sequences for various *Bacillus* species and strains, as also shown in FIGS. 5A, 5B and 5C. Table 1 below correlates SEQ ID NOS. with strains. All sequences are nucleotide sequences, except SEQ ID NO. 2, which is an amino acid sequence.

TABLE 1

| SEQUENCE ID NO. | STRAIN |
|---|---|
| 1, 11, 12 and 13 | *B. subtilis* QST713 |
| 2 | *B. subtilis* QST713 |
| 3 | *B. subtilis* AQ30002 |
| 4 | *B. subtilis* AQ30004 |
| 5 | *B. amyloliquefaciens* FZB42 |
| 6 | *B. pumilus* SAFR-032 |
| 7 | *B. subtilis* 3610 |
| 8 | *B. pumilus* 2808 |
| 9 | *B. atrophaeus* 1942 |
| 10 | *B. licheniformis* 14580 |

The present invention relates to spore-forming bacteria having a swrA gene and, more particularly, to variants of such bacteria having one or more mutations in the swrA gene that result in a non-functional swrA gene that is unable to express the encoded swrA protein and/or unable to encode a functional swrA protein, wherein such mutation and variants with such mutation are referred to herein as swrA⁻. The present invention also encompasses spore-forming bacteria wherein swrA activity has been reduced by means other than mutation of the swrA gene, such as inhibiting swrA activity at other points in the progression from activation of transcription of the swrA gene, transcription of the swrA gene, post transcriptional message processing, translation of swrA mRNA(s), post translational protein processing, to actual protein activity. Any agent or system capable of inhibiting swrA activity is contemplated by this disclosure, including small molecules, drugs, chemicals, compounds, siRNA, ribozymes, antisense oligonucleotides, swrA inhibitory antibodies, swrA inhibitory peptides, dominant negative mutants, aptamers or mirror image aptamers. Cells in which swrA activity has been reduced by means other than mutation of the swrA gene are also referred to as swrA$^-$. The swrA$^-$ cells of the present invention have impaired swarming ability and enhanced ability to improve plant health compared to cells with a wildtype swrA gene. In some embodiments, swrA$^-$ cells lose all or substantially all swarming ability. In some embodiments, swarming ability is reduced compared to swarming ability in isogenic bacterial cells not having a mutation in the swrA ortholog. In some embodiments, swarming ability is reduced by at least about 20%, by at least about 30%, by at least about 40%, by at least about 50%, by at least about 60%, by at least about 70%, by at least about 80%, or by at least about 90%. Swarming ability may be determined by the method described in Example 7 and compared quantitatively by measuring the diameter of bacterial growth on a centrally-inoculated "swarm agar" plate. See FIG. 7.

In other embodiments, in addition to having the above characteristics, swrA$^-$ cells have one or more of the following characteristics compared to cells with a wildtype swrA gene: sandpaper cell or colony morphology, as described above; formation of dense, compact, adherent biofilms on surfaces such as roots; and formation of some long chains of cell during early exponential phase in liquid culture with a lack of clumping or biofilm formation, which demonstrates an ability to respond to environmental signals (i.e., exposure to solid surfaces) in forming biofilms. swrA$^-$ cells form a dense, compact biofilm on surfaces such as roots and have enhanced adherence to non-liquid surfaces such as roots, which is referred to herein as a "more robust biofilm." In one aspect, the non-liquid surface is a solid surface; in others it is a semi-solid surface. Relative adherence to roots can be analyzed by a lack of biofilm disruption when roots are grown in agar, removed from the agar and visualized by light microscopy, as described in Example 9. In another embodiment, the more robust biofilm comprises cells having an extra cell coat and/or a large white (electron transparent) region when visualized with a transmission electron microscope. See images of 30002 in FIG. 14. In one aspect of this embodiment, the average diameter of cells in the more robust biofilm is at least about 1.5 times greater or at least about 2 times greater than the average diameter of cells not having the swrA mutation. See images of 30002 in FIG. 14. In some embodiments, cell morphology of biofilm formed on non-liquid surfaces, such as roots, is analyzed by the method described in Example 9. In yet another embodiment, swrA$^-$ cells may also have enhanced biofilm development when exposed to shear forces in liquid culture. Such shear forces are described in Example 1. The appropriate bacterial cells to use as control cells in comparison to the characteristics of the swrA$^-$ bacterial cells may vary. For example, in one embodiment the comparisons of the above properties are made between bacterial cells having the mutation and isogenic bacterial cells not having the mutation. In another embodiment, the comparison is made between bacterial cells having the mutation and bacterial cells of the same species not having the mutation that also comprise the wildtype alleles of the biofilm-forming genes sfp, epsC and degQ.

In some embodiments these swrA$^-$ spore-forming bacteria are of the family Bacillaceae. In still other embodiments, they are from the genus *Bacillus*. In such embodiment, spore-forming bacterial cells or the *Bacillus* with the swrA mutation may (i) be within the *Bacillus subtilis* clade, as defined below, (ii) have one or more mutations in a swrA ortholog and (iii) have impaired swarming ability and enhanced plant health improvement capability and, optionally, one or more of the other characteristics described in the foregoing paragraph. The term "*Bacillus subtilis* clade," as used herein, is partially described in FIG. 6 and includes the species that have been fully sequenced and determined as likely to have a swrA ortholog and those species for which genomic sequence data is not currently available but which are presumed to have a swrA ortholog based on their close phylogenetic relationships. In addition the term "*Bacillus subtilis* clade" encompasses those *Bacillus* species not identified herein that contain a swrA ortholog by analyses well known to those of skill in the art, including the reciprocal best BLAST hit method.

Homologous sequences are orthologous if they were separated by a speciation event: when a species diverges into two separate species, the divergent copies of a single gene in the resulting species are said to be orthologous. Orthologs are genes in different species that are similar to each other because they originated by vertical descent from a single gene of the last common ancestor. The strongest evidence that two similar genes are orthologous is the result of a phylogenetic analysis of the gene lineage. Genes that are found within one clade are orthologs, and comprise an orthologous group of genes descended from a common ancestor. Orthologs often, but not always, have the same function. The reciprocal best BLAST hit method is the most frequently used strategy to identify potential orthologous pairs. This method assumes that if two similar proteins from two species reciprocally produce the best BLAST hit in each other's proteome, then they are an orthologous pair. See Rivera, M. C., et al., "Genomic Evidence for Two Functionally Distinct Gene Classes," Proc. Natl. Acad. Sci. USA (95): 6239-44 (May 1998). For example, Applicants' cross-species swrA pair analysis revealed that swrA in *B. subtilis, B. amyloliquefaciens, B. licheniformis, B. atrophaeus* and *B. pumilus* produced the reciprocal best BLAST hit, even though the global percent identity of the swrA protein between two species, *B. amyloliquefaciens* and *B. pumilus*, was as low as 70%.

In one embodiment species in the *Bacillus subtilis* clade include but are not limited to *B. pumilus, B. atrophaeus, B. amyloliquefaciens, B. subtilis* and *B. licheniformis, B. aerophilus, B. stratosphericus, B. safensis, B. altitudinus, B. vallismortis, B. halotolerans, B. mojavensis, B. sonorensis, B. aerius* and (ii) variants and strains of *Bacillus subtilis* QST713 wild type swrA$^+$ with one or more mutations in the swrA gene.

The swrA mutations of the present invention include but are not limited to one or more nucleic acid base pair insertions, one or more nucleic acid base pair deletions, one or more nucleic acid changes, including start codon changes, one or more transposon insertions, knockdowns, and/or knock-outs of a wildtype swrA gene. Those of skill in the art will understand that the gene includes regulatory regions, such as the promoter, transcribed regions and other functional sequence regions.

Populations of spore-forming bacteria may be screened for naturally occurring cells having a mutation in the swrA ortholog, as described in Example 24. Alternatively, a number of genetics and molecular biology techniques can be utilized to decrease the expression of swrA at the transcriptional and translational levels to produce swrA$^-$ cells having reduced swarming ability and robust biofilm formation. In some embodiments, such swrA$^-$ cells may have one or more of the other properties (some chaining but no clumping or biofilm formation in liquid culture and altered cell morphology in root biofilms) described above. Antisense RNA, RNAi and ribozymes can be engineered and introduced into the cell to decrease the expression of swrA or other genes that act as positive regulators, such as sigmaD and sigmaA. These transcription factors are known to recognize and directly bind to the swrA promoters (Calvio, et al., "Autoregulation of swrAA and Motility in *Bacillus subtilis*," Journal of Bacteriology (2008) 190:5720-5728). Negative regulators of swrA can also be exploited to decrease swrA expression. For example, FlgM, the sigmaD-specific anti-sigma factor (Fredrick and Helmann, "FlgM is a primary regulator of sigmaD activity, and its absence restores motility to a sinR mutant," Journal of Bacteriology (1996) 178:7010-7013), can be overexpressed to decrease the expression of swrA. Another strategy is to use antimorphic mutation or dominant negative mutation. Because swrA might function as a dimer or a multimer (Dan Kearns, personal communication, 2011), a heteromeric swrA consisting of mutated and wildtype swrA units would no longer be functional. Examples of genetic engineering techniques used to decrease expression of swrA are set forth in Example 25.

The term "position" when used in accordance with the present invention means the position of a nucleotide within a nucleic acid sequence or an amino acid within an amino acid sequence depicted herein. The term "corresponding" is used herein to indicate that a position is not limited to being determined by the number of the preceding nucleotides or amino acids. For example, the position of a given nucleotide in accordance with the present invention which may be deleted may vary due to deletions or additional nucleotides elsewhere in a swrA gene such as in the 5'-untranslated region (UTR) including the promoter and/or any other regulatory sequences or gene. Accordingly, when used herein "corresponding position" or "a position corresponding to" a specific position of a nucleotide sequence or amino acid sequence refers to a position which, when a sequence in question is aligned with, for example, the nucleotide sequence of SEQ ID NO. 1 or the amino acid sequence of SEQ ID NO. 2 (e.g., the reference sequence) by standard methods, exhibits significant homology to the indicated position or, sometimes, to portions of the nucleotide sequence of SEQ ID NO. 1 or to the amino acid sequence of SEQ ID NO. 2. Different species of, for example, *Bacillus*, while being similar in the nucleotide sequence of the swrA gene and/or the swrA protein, are not identical to the reference sequence and, in particular, may contain different, fewer or more nucleotides or amino acids than the reference sequence. The stretches of a sequence in question which are similar to SEQ ID NOS. 1 or 2, for example, can be easily determined by standard in silico alignment techniques using established software, for example using ClustalW, with parameters set to "standard" or preset."

In some embodiments, the swrA mutation in a variant spore-forming bacteria occurs at a nucleotide position that causes an amino acid change corresponding to at least one of the following conserved positions of the protein set forth in SEQ ID NO. 2: positions 1-17, positions 19-20, position 22, positions 25-29, positions 31-33, positions 36-39, positions 41-48, positions 50-51, position 53, position 56, position 58, position 60, positions, 61, positions 64-65, positions 67-69, position 71-86, position 88, position 95, position 97, positions 99-113 and position 116. These conserved positions are designated with an asterisk in the alignment shown in FIG. 5C. In still other embodiments, the mutation occurs at a nucleotide position that causes an amino acid change corresponding to a change to at least one of the following conserved positions of the protein: positions 1-17, positions 71-86 and positions 99-113. In addition, such nucleotide change (to be a swrA mutation) should impair the cells' swarming ability and/or enhance its ability to promote plant health compared to cells with the wildtype swrA gene. In some embodiments, such mutation will also result in the following characteristics compared to wildtype cells: sandpaper cell morphology, more robust root colonization and/or formation of long chains with lack of clumping in liquid culture, as described above.

In other embodiments the swrA mutation occurs at a position corresponding to positions 1-100, 1-50, 1-40, or 7-40 of any one of SEQ ID NOS. 1 and 5-10.

In some embodiments, the swrA$^-$ cells have a swrA gene that has percent identity to the swrA gene of SEQ ID NO. 1 of at least about 60%, of at least about 70%, of at least about 80%, of at least about 90%, or of at least about 95%. In particular embodiments the wildtype version of such swrA$^-$ bacteria with at least about 60% to about 95% sequence identity to SEQ ID NO. 1 has a swrA protein that is orthologous to SEQ ID NO. 2.

In one embodiment, the microorganism has, at a position corresponding to one or more of positions 26-34 (a homopolymeric stretch of 8 A:T base pairs) or positions 1-3 (the start codon) of the swrA gene set forth as SEQ ID NO. 1, a mutation. In some instances, this mutation is an insertion or deletion. An example of a deletion to positions 26-34 is the mutated swrA gene set forth in SEQ ID NO. 3. An example of a mutation where the start codon is mutated to a non-start codon, which produces a non-functional swrA transcript for translation is set forth in SEQ ID NO. 4.

In another embodiment, the swrA$^-$ cells have a swrA$^-$ gene that has sequence identity to a swrA wildtype gene of the same *Bacillus* species and, in some embodiments, of the same strain, of at least about 85%, of at least about 90%, or of at least about 95%. In some embodiments, the swrA$^-$ cells have a swrA$^-$ gene that has sequence identity to a swrA wildtype gene of the same *Bacillus* species and such *Bacillus* species is within the *Bacillus subtilis* clade. In some embodiments the *Bacillus* species is *pumilus*, *atrophaeus*, *amyloliquefaciens*, *subtilis*, *licheniformis*, *aerophilus*, *stratosphericus*, *safensis*, *altitudinus*, *vallismortis*, *halotolerans*, *mojavensis*, *sonorensis*, or *aerius*. In still other embodiments, the swrA$^-$ cells have a mutant swrA gene that has sequence identity to one or more of the sequences set forth in SEQ ID NOS. 1 and 5-10 of at least about 85%, of at least about 90%, or of at least about 95%.

In one embodiment, spore-forming bacterial cells, including those in the *Bacillus subtilis* clade, having a mutation in the swrA ortholog comprise a wildtype sfp ortholog. In other embodiments, such spore-forming bacterial cells also comprise wildtype degQ and epsC orthologs. In still other embodiments, the spore-forming bacterial cells from either of the above embodiments are *Bacillus subtilis* or *Bacillus amyloliquefaciens*. The sfp, epsC and degQ genes from wildtype QST713 are provided herein as SEQ ID NOS. 11, 12, and 13, respectively. Orthologous sfp, epsC and degQ genes from other species, including the *Bacillus* species and strains for which swrA nucleotide sequences have been provided herein (in the sequence listing and/or in FIGS. 5A, B and C) are publicly available through GenBank and in various papers, including the McLoon paper cited above. In one embodiment, the wildtype degQ, epsC and sfp orthologs have at least about 90%, or at least about 95%, or at least about 96%, or at least about 97%, or at least about 98%, or at least about 99% sequence identity to one of the degQ, epsC and sfp genes, respectively, in *B. amyloliquefaciens* FZB42, *B. pumilus* SAFR-032, *B. subtilis* 3610, *B. atrophaeus* 1942, and *B. licheniformis* 14580. In one aspect in determining sequence identity, the spore-forming bacterial cells having the mutation in the swrA ortholog are of the same species as one of the above referenced strains.

The percentage of swrA$^-$ cells in a particular composition of the present invention will vary depending on the specific purposes and application methods used for the composition. The total cells in the compositions and methods of the present invention can include different cell types (e.g., a combination of bacterial and non-bacterial cells), or can include bacterial cells of two or more species, or can include *Bacillus* cells of two or more *Bacillus* species, or can be *B. subtilis* cells of two or more different genotypes or strains, or can be *B. amyloliquefaciens* cells of two or more different genotypes or strains, or be cells with one or more different swrA$^-$ mutations.

In some embodiments, the percentage of swrA$^-$ cells in the total cells in the compositions and methods of the present invention will be at least 3.5%, or at least 3.6%, or at least 3.7%, or at least 3.8%, or at least 3.9%, or at least 4%, or at least 5%, or at least 6%, or at least 7%, or at least 8%, or at least 9%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 98%, or at least 99%, or be 100%. In some embodiments of the present invention, all of the cells present in a particular composition or used in a particular method are all swrA$^-$ cells (i.e., 100% swrA$^-$ cells).

In some embodiments, the percentage of swrA$^-$ cells in the total cells in the composition and methods of the present invention will be about 3.5% to about 99.9%. In another embodiment, the percentage will be about 5% to about 99%. In another embodiment, the percentage will be about 10% to about 99%.

In some embodiments, the number of colony forming units ("cfu") per gram ("g") of swrA$^-$ cells in the compositions and methods of the present invention will be at least $1\times10^7$ cfu/g or at least $1\times10^8$ cfu/g or at least $1\times10^9$ cfu/g or at least $2\times10^9$ cfu/g, or at least $3\times10^9$ cfu/g or at least $4\times10^9$ cfu/g or at least $5\times10^9$ cfu/g or at least $6\times10^9$ cfu/g or at least $7\times10^9$ cfu/g, or at least $8\times10^{10}$ cfu/g, or at least $8.5\times10^{10}$ cfu/g, or at least $9\times10^{10}$ cfu/g, or at least $9.5\times10^{10}$ cfu/g, or at least $1\times10^{11}$ cfu/g, or at least $2\times10^{11}$ cfu/g, or at least $3\times10^{11}$ cfu/g, or at least $4\times10^{11}$ cfu/g, or at least $5\times10^{11}$ cfu/g, or at least $6\times10^{11}$ cfu/g, or at least $7\times10^{11}$ cfu/g, or at least $8\times10^{11}$ cfu/g, or at least $9\times10^{11}$ cfu/g, or at least $1\times10^{12}$ cfu/g, or at least $1\times10^{13}$ cfu/g, or at least $1\times10^{14}$ cfu/g.

In other embodiments the total amount of swrA$^-$ cells in the compositions and methods of the present invention is based on the relative or actual dry weight basis of the swrA$^-$ cells in the total compositions.

In some embodiments the total amount of swrA$^-$ cells in the compositions and methods of the present invention is based on the cfu/g of the swrA$^-$ cells in the compositions.

The present invention also encompasses methods for enhancing plant health, enhancing plant growth and/or controlling plant pests and diseases by administering to a plant or a plant part, such as a seed, root, rhizome, corm, bulb, or tuber, or by applying to a locus on which plant or plant parts grow, such as soil, one or more of the novel variants and strains of spore-forming bacteria, including *Bacillus* described above; or cell-free preparations thereof; or metabolites thereof.

"Plant health" as used herein means a condition of a plant which is determined by several aspects alone or in combination with each other. One important indicator for the condition of the plant is the crop yield. "Crop" and "fruit" are to be understood as any plant product which is further utilized after harvesting, e.g. fruits in the proper sense, vegetables, nuts, grains, seeds, wood (e.g., in the case of silviculture plants), flowers (e.g., in the case of gardening plants, ornamentals), etc.; that is, anything of economic value that is produced by the plant. Another indicator for the condition of the plant is the plant vigor. The plant vigor becomes manifest in several aspects, too, some of which are visual appearance, e.g., leaf color, fruit color and aspect, amount of dead basal leaves and/or extent of leaf blades, plant weight, plant height, extent of plant verse (lodging), number, strongness and productivity of tillers, panicles' length, extent of root system, strongness of roots, extent of nodulation, in particular of rhizobial nodulation, point of time of germination, emergence, flowering, grain maturity and/or senescence, protein content, sugar content and the like. Another indicator for the condition of the plant is the plant's tolerance or resistance to biotic and abiotic stress factors.

According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the composition of the invention. According to the present invention, it is preferred that the yield be increased by at least 0.5%, or by at least 1%, or by at least 2%, or by at least 4%, or by at least 5%, or by at least 10% when compared to appropriate controls.

In another preferred embodiment, the present invention provides the use of the composition of the invention for increasing the yield and/or improving the vigor of a plant, e.g., of an agricultural, silvicultural and/or ornamental plant.

The present invention further provides a method for increasing the yield and/or improving the vigor of a plant, which comprises treating the plant, the locus where the plant is growing or is expected to grow (i.e., the plant locus), and/or the propagules from which the plant grows with the compositions or spore-forming bacteria of the invention. In some embodiments, the treated plant or plants grown in a treated plant locus are grown in an environment that is physically stressful to the plants being grown. Such conditions may be cold temperatures (e.g., 15° C. or less), drought conditions, low soil nutrients (e.g., with reduced levels of nitrogen and/or potassium and/or phosphate or other inorganic micronutrients) and/or increased, non-optimal soil salinity. According to the present invention, "improved plant vigor" means that certain crop characteristics are increased or improved by a measurable or noticeable amount over the same factor of the plant produced under the same conditions, but without the application of the composition of the present invention. Improved plant vigor can be characterized, among others, by following improved properties of the plant: (a) improved vitality of the plant, (b) improved quality of the plant and/or of the plant products, e.g., enhanced protein content, (c) improved visual appearance, (d) delay of senescence, (e) enhanced root growth and/or more developed root system (e.g., determined by the dry mass of the root), (f) enhanced nodulation, in particular rhizobial nodulation, (g) longer panicles, (h) bigger leaf blade, (i) less dead basal leaves, (j) increased chlorophyll content, (k) prolonged photosynthetically active period, (l) increased or improved plant stand density, (m) less plant verse (lodging), (n) increased plant weight, (o) increased plant height, (p) tillering increase, (q) stronger and/or more productive tillers, (r) less non-productive tillers, (s) enhanced photosynthetic activity and/or enhanced pigment content and thus greener leaf color, (t) earlier and/or improved germination, (u) improved and/or more uniform and/or earlier emergence, (v) increased shoot growth, (w) earlier flowering, (x) earlier fruiting, (y) earlier grain maturity, (z) less fertilizers needed, (aa) less seeds needed.

Compositions of the present invention are also useful to control plant pathogens, such as plant pathogenic fungi, including, for example, various soil-borne and/or seed-borne pathogens, such as *Aphanomyces cochlioides, Cylindrocladium parasiticum, Fusarium avenaceum, Fusarium culmorum, Phytophthora capsici, Phytophthora cinnamomi, Pythium ultimum, Rhizoctonia solani, Sclerotinia sclerotiorum, Sclerotinia minor, Sclerotium rolfsii, Ustilago hordei, Stagonospora nodorum, Aspergillus fumigants, Verticillium dahliae, Tapesia yallunde, Alternaria alternate* and *Penicillium expansum*. In one embodiment, the soil-borne pathogens that are controlled are *P. capsici, S. rolfsii,* and *C. parasiticum.*

Compositions of the present invention are also useful to control plant pests, including plant parasitic nematodes, such as, for example, root-knot, cyst, lesion and ring nematodes, including *Meloidogyne* spp., *Heterodera* spp., *Globodera* spp., *Praylenchus* spp. and *Criconemella* sp. Compositions are also useful to control *Tylenchulus semipenetrans, Trichodorus* spp., *Longidorus* spp., *Rotylenchulus* spp., *Xiphinema* spp., *Belonolaimus* spp. (such as *B. longicaudatus*), *Criconemoides* spp., *Tylenchorhynchus* spp., *Hoplolaimus* spp., *Rotylenchus* spp., *Helicotylenchus* spp., *Radopholus* spp. (such as *R. citrophilis* and *R. similis*), *Ditylenchus* spp. and other plant parasitic nematodes. In some embodiments the targets are cyst nematodes, such as *Heterodera glycines* (soybean cyst nematodes), *Heterodera schachtii* (beet cyst nematode), *Heterodera avenae* (Cereal cyst nematode), *Meloidogyne incognita* (Cotton (or southern) root knot nematode), *Globodera rostochiensis* and *Globodera pallida* (potato cyst nematodes). In other embodiments, the targets are root knot nematodes, such as *M. incognita* (cotton root knot nematode), *M. javanica* (Javanese root knot nematode), *M. hapla* (Northern root knot nematode), and *M. arenaria* (peanut root knot nematode).

The term "control," as used herein, means killing or inhibiting the growth of microorganisms or, as to plant pests, such as nematodes, killing, reducing in numbers, and/or reducing growth, feeding or normal physiological development, including, for root knot nematodes, the ability to penetrate roots and to develop within roots. An effective amount is an amount able to measurably reduce (i) the growth of microorganisms or, (ii) as to plant pests, pest growth, feeding, mobility, reproductive capability or, (iii) as to plant parasitic nematode pests, specifically, root penetration, maturation in the root, and/or general normal physiological development and symptoms resulting from nematode infection. In some embodiments symptoms and/or plant pathogens or plant pests, such as nematodes, are reduced by at least about 5%, at least about 10%, at least about 20%, at least about, 30%, at least about 40%, at least about 50%, at least about 60%, at least about 70%, at least about 80%, or at least about 90%.

The novel variants and strains of *Bacillus* of the present invention may be present in the compositions of the present invention as spores (which are dormant), as vegetative cells (which are growing), as transition state cells (which are transitioning from growth phase to sporulation phase) or as a combination of all of these types of cells. In some embodiments, the composition comprises mainly spores. In some embodiments, the percentage of swrA$^-$ cells that are spores is at least about 70%; at least about 80%, at least about 81%, at least about 82%, at least about 83%, at least about 84%, at least about 85%, at least about 86%, at least about 87%, at least about 88%, at least about 89%, at least about 90%, at least about 95%.

Metabolites of the novel variants and strains of *Bacillus* of the present invention include lipopeptides, such as iturins, surfactins, plipastatins, fengycins and agrastatins and other compounds with antibacterial properties. Lipopeptide metabolites of QST713 are described in detail in U.S. Pat. Nos. 6,291,426, and 6,638,910. See, also, Marc Ongena and Philippe Jacques, "*Bacillus* Lipopeptides: Versatile Weapons for Plant Disease Biocontrol," Trends in Microbiology (Mar. 1, 2008) Volume 16, Issue 3, 115-125.

Compositions of the present invention can be obtained by culturing the novel variants and strains of *Bacillus* according to methods well known in the art, including by using the media and other methods described in U.S. Pat. No. 6,060, 051. Conventional large-scale microbial culture processes include submerged fermentation, solid state fermentation, or liquid surface culture. Towards the end of fermentation, as nutrients are depleted, *Bacillus* cells begin the transition from growth phase to sporulation phase, such that the final product of fermentation is largely spores, metabolites and residual fermentation medium. Sporulation is part of the natural life cycle of *Bacillus* cells, including *Bacillus subtilis*, and is generally initiated by the cell in response to nutrient limitation. Fermentation is configured to obtain high levels of colony forming units of *Bacillus* and to promote sporulation. The bacterial cells, spores and metabolites in culture media resulting from fermentation may be used directly or concentrated by conventional industrial methods, such as centrifugation, tangential-flow filtration, depth filtration, and evaporation. Fermentation broth and broth concentrate are both referred to herein as "fermentation products." Compositions of the present invention include fermentation products. In some embodiments, the concentrated fermentation broth is washed, for example, via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation.

The resulting dry products may be further processed, such as by milling or granulation, to achieve a specific particle size or physical format. Carriers, described below, may also be added post-drying.

Cell-free preparations of fermentation broth of the novel variants and strains of *Bacillus* of the present invention can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

Metabolites of *Bacillus subtilis* can be obtained according to the methods set forth in U.S. Pat. No. 6,060,051. The term "metabolites" as used herein may refer to semi-pure and pure or essentially pure metabolites, or to metabolites that have not been separated from *Bacillus subtilis*. In some embodiments, after a cell-free preparation is made by centrifugation of fermentation broth, the metabolites may be purified by size exclusion filtration such as the SEPHADEX® resins including LH-20, G10, and G15 and G25 that group metabolites into different fractions based on molecular weight cut-off, such as molecular weight of less than about 2000 daltons, less than about 1500 daltons, less than about 1000 daltons and so on, as the lipopeptides are between 800 daltons and 1600 daltons.

Concentration methods and drying techniques described above for formulation of fermentation broth are also applicable to metabolites.

Compositions of the present invention may include formulation inerts added to compositions comprising cells, cell-free preparations or metabolites to improve efficacy, stability, and usability and/or to facilitate processing, packaging and end-use application. Such formulation inerts and ingredients may include carriers, stabilization agents, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the carrier is a binder or adhesive that facilitates adherence of the composition to a plant part, such as a seed or root. See, for example, Taylor, A. G., et al., "Concepts and Technologies of Selected Seed Treatments" Annu. Rev. Phytopathol. 28: 321-339 (1990). The stabilization agents may include anti-caking agents, anti-oxidation agents, desiccants, protectants or preservatives. The nutrients may include carbon, nitrogen, and phosphors sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, antifreeze agents or colorants. In some embodiments, the composition comprising cells, cell-free preparation or metabolites produced by fermentation can be used directly with or without water as the diluent without any other formulation preparation. In some embodiments, the formulation inerts are added after concentrating fermentation broth and during and/or after drying.

In some embodiments the compositions of the present invention are used to treat a wide variety of agricultural and/or horticultural crops, including those grown for seed, produce, landscaping and those grown for seed production. Representative plants that can be treated using the compositions of the present invention include but are not limited to the following: *brassica*, bulb vegetables, cereal grains, citrus, cotton, curcurbits, fruiting vegetables, leafy vegetables, legumes, oil seed crops, peanut, pome fruit, root vegetables, tuber vegetables, corm vegetables, stone fruit, tobacco, strawberry and other berries, and various ornamentals.

The compositions of the present invention may be administered as a foliar spray, as a seed/root/tuber/rhizome/bulb/corm/slip treatment and/or as a soil treatment. The seeds/root/tubers/rhizomes/bulbs/corms/slips can be treated before planting, during planting or after planting. When used as a seed treatment, the compositions of the present invention are applied at a rate of about $1 \times 10^2$ to about $1 \times 10^7$ cfu/seed, depending on the size of the seed. In some embodiments, the application rate is about $1 \times 10^3$ to about $1 \times 10^6$ cfu per seed. When used as a soil treatment, the compositions of the present invention can be applied as a soil surface drench, shanked-in, injected and/or applied in-furrow or by mixture with irrigation water. The rate of application for drench soil treatments, which may be applied at planting, during or after seeding, or after transplanting and at any stage of plant growth, is about $4 \times 10^{11}$ to about $8 \times 10^{12}$ cfu per acre. In some embodiments, the rate of application is about $1 \times 10^{12}$ to about $6 \times 10^{12}$ cfu per acre. In some embodiments, the rate of application is about $6 \times 10^{12}$ to about $8 \times 10^{12}$ cfu per acre. The rate of application for in-furrow treatments, applied at planting, is about $2.5 \times 10^{10}$ to about $5 \times 10^{11}$ cfu per 1000 row feet. In some embodiments, the rate of application is about $6 \times 10^{10}$ to about $4 \times 10^{11}$ cfu per 1000 row feet. In other embodiments, the rate of application is about $3.5 \times 10^{11}$ cfu per 1000 row feet to about $5 \times 10^{11}$ cfu per 1000 row feet. Those of skill in the art will understand how to adjust rates for broadcast treatments (where applications are at a lower rate but made more often) and other less common soil treatments.

The compositions of the present invention may be mixed with other chemical and non-chemical additives, adjuvants and/or treatments, wherein such treatments include but are not limited to chemical and non-chemical fungicides, insecticides, miticides, nematicides, fertilizers, nutrients, minerals, auxins, growth stimulants and the like. In some embodiments, the compositions of the present invention further comprise insecticides, miticides, nematicides, fertilizers, nutrients, minerals, auxins, growth stimulants and the like. In other embodiments, the compositions of the present invention are applied in rotation with other treatments; e.g., as part of a spray program. In still other embodiments, the compositions of the present invention are applied to plants at the same time as the other treatments.

In some embodiments in which the compositions are used to control plant diseases and/or to enhance plant health, the compositions are mixed with, further comprise, or are applied at the same time as or as part of a treatment program with at least one fungicide. Commonly used fungicides include, but are not limited to, strobilurins, carboxamides, sulfananilides, phenylsulfamides, azoles, nitrogenous heterocycles, dicarboximides, phthalimides, carbamates, thiocarbamates, formaidines, antibiotics, aromatics, guanidines, organochlorine compounds, organometallics, organophosphorus compounds, nitrophenyl compounds, sulfur heterocyclyl compounds, ureas, inorganics, and others (e.g., benzamacril, carvone, essential oil extract from plants, cedar leaf oil, neem oil, chloropicrin, DBCP, drazoxolon, fenaminosulf, metzoxolon, oxolinic acid, spiroxamine, cymoxanil, metrafenone. Prohexadione calcium, thicyofen, dithane, chlorothalnil, dichlorophen, dicloran, nitrothal-isopropyl, bronopol, diphenylamine, mildiomycin, oxin-copper, cyflufenamide (e.g., N-(cyclopropylmethoxyimino-(6-difluoromethoxy-2,3-difluorophenyl)-methyl)-2-phenylacetamide), UK-2A (antibiotic isolated from *Streptomyces* sp. 517-02), RANMAN™ (Ishihara Sangyo Kaisha, Ltd), and microbe-based products, including but not limited to *Bacillus subtilis*-based products, *Bacillus pumilus*-based products, such as those based on *Bacillus pumilus* QST2808™, which are available from AgraQuest, Inc. as SONATA® or BALLAD® and *Streptomyces*-based products, such as products based on *Streptomyces* sp. AQ4800™. Detailed information of AQ4800™ (AgraQuest), SONATA® and BALLAD® (AgraQuest) can be found in U.S. Pat. Nos. 6,524,577; 6,852,317; 6,245,551; 6,586,231; and 6,635,245. Each of the patents, patent publications cited here is incorporated by reference in its entirety herein, including all drawings/photographs that are a part thereof.

Strobilurins include, but are not limited to, azoxystrobin, dimoxystrobin, enestroburin, fluoxastrobin, kresoxim-methyl, metominostrobin, picoxystrobin, pyraclostrobin, pyroxastrobin, trifloxystrobin, orysastrobin, methyl (2-chloro-5-[1-(3-methylbenzyloxyimino)-ethyl]benzyl)-carbamate, methyl (2-chloro-5-[1-(6-methylpyridin-2-ylmethoxyimino) ethyl]benzyl)carbamate, methyl 2-(ortho-(2,5-dimethylphenyloxymethylene)phenyl)-3-methoxyacrylate; 2-(2-(6-(3-chloro-2-methyl-phenoxy)-5-fluoro-pyrimidin-4-yloxy) phenyl)-2-methoxyimino-N-methyl-acetamide 3-methoxy-2-(2-(N-(4-methoxyphenyl)-cyclopropanecarboximidoylsulfanylmethyl)-phenyl)-acrylic acid methyl ester.

Carboxamides include, but are not limited to, carboxanilides (e.g., bixafen, boscalid, carboxin, fenhexamid, furametpyr, isopyrazam, isotianil, metsulfovax, oxycarboxin, pyracarbolid, penthiopyrad, sedaxane (racemic cis and trans isomers), thifluzamide, tiadinil, N-(4'-bromobiphenyl-2-yl)-4-difluoromethyl-2-methylthiazole-5-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoro-methyl-2-methylthiazole-5-carboxamide, N-(3',4'-dichloro-4-fluorobiphenyl-2-yl)-3-difluoromethyl-1-methylpyrazole-4-carboxamide, N-(2-(1,3-dimethylbutyl)-phenyl)-1,3-dimethyl-5-fluoro-1H-pyrazole-4-carboxamide, N-(4'-chloro-3',5-difluorobiphenyl-2-yl)-3-difluoromethyl-1-methyl-1H-pyrazole,-4-carboxamide, N-(4'-chloro-3',5-difluorobiphenyl-2-yl)-3-trifluoromethyl-1-methyl-1H-pyrazole-4-carboxamide, N-(3',4'-dichloro-4-fluorobiphenyl-2-yl)-3-difluoromethyl-1-methylpyrazole-4-carboxamide, N-(4'-(3,3-dimethylbutyn-1-yl)-1,1'-biphenyl-2-yl)-3-difluoromethyl-1-methylpyrazole-4-carboxamide, N-(4'-(3,3-dimethylbutyn-1-yl)-1,1'-biphenyl-2-yl)-3-trifluoromethyl-1-methylpyrazole-4-carboxamide, N-(4'-(3,3-difluorobutyn-1-yl)-1,1'-biphenyl-2-yl)-3-difluoromethyl-1-methylpyrazole-4-carboxamide, N-(4'-(3,3-difluorobutyn-1-yl)-1,1'-biphenyl-2-yl)-3-trifluoromethyl-1-methylpyrazole-4-carboxamide, 2-chloro-N-(4'-(3,3-dimethylbutyn-1-yl)-1,1'-biphenyl-2-yl)-3-pyridine carboxamid, N-(2-cyanophenyl)-3,4-dichloroisothiazole-5-carboxamide, N-(cis-2-bicyclopropyl-2-yl-phenyl)-3-difluoromethyl-1-methyl-1H-pyrazole-4-carboxamide, N-(trans-2-bicyclopropyl-2-ylphenyl)-3-difluoromethyl-1-methyl-1H-pyrazole-4-carboxamide, benalaxyl, metalaxyl, mefenoxam, ofurace, and oxadixyl), carboxylic acid morpholides (e.g., dimethomorph and flumorph), benzamides (e.g., benzohydroxamic acid, flumetover, fluopicolide, fluopyram, tioxymid, trichlamide, zarilamide, N-acetonylbenzamides, including zoxamide and other related compounds, described and/or claimed in U.S. Pat. No. 5,304,572, and N-(3-ethyl-3,5-5-trimethyl-cyclohexyl)-3-formyl-amino-2-hydroxybenzamide), benzanilides (e.g., benodanil, flutolanil, mebenil, mepronil, salicylanilide, and tecloftalam), furanilides (e.g., fenfuram, furalaxyl, furcarbanil, and methfuroxam), furamides (e.g., cyclafuramid, and furmecyclox), nicotinamides (e.g., 2-chloro-N-(1,1,3-trimethyl-indan-4-yl)-nicotinamide, N-(1-(5-bromo-3-chloro-pyridin-2-yl)ethyl)-2,4-dichloronicotinamide, 2-amnio-4nethyl-thiazole-5-carboxamide, and N-((5-bromo-3-chloropyridin-2-yl)-methyl)-2,4-dichloronicotinamide), sulfonamides (e.g., N-(4-chloro-2-nitrophenyl)-N-ethyl-4-methyl-benzenesulfonamide), penthiopyrad, isopyrazam, 1-methyl-pyrazol-4-ylcarboxamide, and other carboxamides (e.g., chloraniformethan, carpropamid, cyflufenamid diclocymet, ethaboxam, fenoxanil, mandipropamid, silthiofam, N-(2-(4-[3-(4-chlorophenyl)prop-2-ynyloxy]-3-methoxyphenyl)ethyl)-2-methanesulfonylamino-3-methyl-butyramide, oxytetracylin, N-(2-(4-[3-(4-chlorophenyl)prop-2-ynyloxy]-3-methoxyphenyl)ethyl)-2-ethane-sulfonylamino-3-methylbutyramide, N-(6-methoxypyridin-3-yl)cyclopropanecarboxylic acid amide).

Sulfananilides include, but are not limited to, flusulfamides.

Phenylsulfamides include, but are not limited to, dichlofuanid and tolyfluanid.

Azoles include, but are not limited to, triazoles (e.g., azaconazole, bitertanol, bromuconazole, cyproconazole, difenoconazole, diniconazole, diniliconazole-M, enilconazole, epoxiconazole, etaconazole, fenbuconazole, flusilazole, fluotrimazole, fluquinconazole, flutriafol, furconazole, furconazole-cis, hexaconazole, imibenconazole, ipconazole, metconazole, myclobutanil, palcobutrazol, penconazole, propiconazole, prothioconazole, quinconazole, simeconazole, tebuconazole, tetraconazole, triadimenol, triadimefon, triazbutil, triticonazole; uniconazole, 1-(4-chlorophenyl)-2-([1,2,4]triazol-1-yl)-cycloheptanol, and amisulbrom), imidazoles (e.g., climbazole, clotrimazole, cyazofamid, fenapanil, glyodin, imazalil, oxpoconazole, pefurazoate, prochloraz, triazoxide, triflumizole, and 2-chloro-5-((4-chloro-2-methyl-5-(2,4,6-trifluorophenyl))imidazol-1-yl)pyridine), benzimidazoles (e.g., benomyl, carbendazim, chlofenazole, cypendazole, debacarb, fuberidazole, mercarbinizid, rabenazole, and thiabendazole), azolopyrimidines (e.g., 5-chloro-7-(4-methyl-piperidin-1-yl)-6-(2,4,6-trifluorophenyl)-[1,2,4]-triazolo-[1,5a]-pyrimidine, 6-(3,4-dichlorophenyl)-5-methyl[1,2,4]triazolo[1,5-a]pyrimidin-7-ylamine, 6-(4-tert-butylphenyl)-5-methyl[1,2,4]triazolo[1,5-a]pyrimidin-7-ylamine, 5-methyl-6-(3,5,5-trimethylhexyl)[1,2,4]triazolo[1,5-a]pyrimidin-7-ylamine, 5-methyl-6-octyl-[1,2,4]triazolo[1,5-a]pyrimidin-7-ylamine, 5-ethyl-6-octyl-[1,2,4]triazolo[1,5-a]pyrimidin-2,7-diamine, 6-ethyl-5-octyl-1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]-triazolo[1,5-a]-pyrimidin-7-ylamine, 5-trifluoromethyl-6-(3,5,5-trimethylhexyl)-[1,2,4]triazolo[1,5-a]pyrimidin-7-ylamine, and 2-butoxy-6-iodo-3-propylchromen-4-one), and other azoles (e.g., bentaluron, etridiazole, and hymexazole).

Nitrogenous heterocycles include, but are not limited to, pyridines (e.g., buthiobate, dipyrithone, fluazinam, pyridinitril, pyrifenox, pyroxychlor, pyroxyfur, 2,3,5,6-tetrachloro-4-methanesulfonlypyridine, 3,4,5-trichloro-pyridine-2,6-dicarbonitrile, and 3-[5-(4-chlorophenyl)-2,3-dimethyl isoxazolidin-3-yl]pyridine), pyrimidines (e.g., bupirimate, cyprodinil, diflumetorim, dimethirimol, ethirimol, ferimzone, fenarimol, mepanipyrim, nuarimol, triarimol, and pyrimethanil), piperazine (e.g., triforine), piperidines (e.g., fenpropidin and piperalin), pyrroles (e.g., fludioxonil and fenpiclonil), morpholines (e.g., aldimorph, benzamorph, dodemorph, fenpropimorph, and tridemorph), nitrapyrin, quinolines (e.g., ethoxyqquin, halacrinate, 8-hydroxyquinoline sulfate, quinacetol, and quinoxyfen), quinones (e.g., benquinox, chloranil, dichlone, and dithianon), quinoxalines (e.g., chinomethionat, chlorquinox, and thioquinox), and other nitrogenous heterocycles (e.g., acibenzolar-S-methyl, anilazine, diclomezine fenamidone, flutianil, octhilinone, probenazole, proquinazid, pyroquilon, thiadifluor, tricyclazole, N,N-dimethyl-3-(3-bromo-6-fluoro-2-methylindole-1-sulfonyl)-[1,2,4]triazolesulfonamide, 3-(4-chlorophenyl)-1-(2,2,2-trifluorethyl)-1,2,4-triazin-6(1H)-one, 3-(4-chlorophenyl)-1-(2,2,2-trifluorethyl)-4,5-dihydro-1,2,4-triazin-6(1H)-one, 6-(4-chlorophenyl)-2-(2,2,2-trifluorethyl)-1,2,4-triazin-3(1H)-one, 6-(4-chlorophenyl)-2-(2,2,2-trifluorethyl)-4,5-dihydro-1,2,4-triazin-3(1H)-one.

Dicarboximides include, but are not limited to, chlozolinate, dichlozoline, iprodione, isovaledione, myclozolin, procymidone, vinclozolin, famoxadone, and fluoroimide.

Phthalimides include, but are not limited to, captafol, captan, ditalimfos, folpet, and trichlorfenphim.

Carbamates include, but are not limited to, diethofencarb, flubenthiavalicarb, iprovalicarb, propamocarb, furophanate, thiophanate methyl 3-(4-chlorophenyl)-3-(2-isopropoxycarbonylamino-3-methylbutyrylamino)-propionate, 4-fluorophenyl N-(1-(1-(4-cyanophenyl)ethanesulfonyl)-but-2-yl) carbamate, and 3-iodo-2-propynylbutylcarbamate (iodocarb).

Thiocarbamates include, but are not limited to, methasulfocarb and prothiocarb.

Dithiocarbamates include, but are not limited to, azthiram, carbamorph, cufraneb, cuprobam, dazomet, disulfuram, ferbam, mancozeb, maneb, milneb, metiram, metam, nabam, propineb, tecoram, thiram, zineb, and ziram.

Formamidines include, but are not limited to, N'-(4-(4-chloro-3-trifluoromethyl-phenoxy)-2,5-dimethylphenyl)-N-ethyl-N-methyl formamidine, N'-(4-(4-fluoro-3-trifluoromethylphenoxy)-2,5-dimethyl-phenyl)-N-ethyl-N-methyl formamidine, N'-(2-methyl-5-trifluormethyl-4-(3-trimethylsilanyl-propoxy)phenyl)-N-ethyl-N-methyl formamidine, and N'-(5-difluormethyl-2-methyl-4-(3-trimethyl-silanyl-propoxy)phenyl)-N-ethyl-N-methyl formamidine.

Antibiotics include, but are not limited to, aureofungin, blasticidin-S, griseofulvin, kasugamycin, natamycin, polyoxin, polyoxorim, streptomycin, and validamycin A.

Aromatics include, but are not limited to, biphenyl, chloroneb, and cresol.

Guanidines include, but are not limited to, dodine, iminoctadine triacetate, iminoctadine tris(albesilate), and guazatine acetate.

Organochlorine compounds include, but are not limited to, bithionol, chlorothalonil, phthalide, hexachlorobenzene, pencycuron, pentachlorophenol, perchlorocyclohex-2-en-1-one, and quintozene(PCNB).

Organometallics include, but are not limited to, fentin salts, decafentin, and tributyltin oxide.

Organophosphorus compounds include, but are not limited to, ampropylfos, edifenphos, fenitropan, fosetyl, fosetyl-aluminum, hexylthiofos, iprobenfos, phosdiphen, triamphos, pyrazophos, tolclofos-methyl, phosphorous acid and its salts.

Nitrophenyl compounds include, but are not limited to, binapacryl, chlorodinitronapthalene, dichloran, dinocap, dinobuton, meptyldinocap, dinocton, dinopenton, dinosulfon, dinoterbon, DNOC, sultropen, and tecnazene (TCNB).

Sulfur heterocyclyl compounds include, but are not limited to, isoprothiolane and dithianon.

Ureas include, but are not limited to, pencycuron and quinazimid.

Inorganics fungicides include, but are not limited to, Bordeaux mixture, copper acetate, copper hydroxide, copper oxide, copper oxychloride, basic copper sulfate, sulfur, sodium bicarbonate, and potassium bicarbonate.

In some embodiments wherein the compositions are used to enhance plant health, the compositions are mixed with or further comprise at least one fertilizer, nutrient, mineral, auxin, growth stimulant and the like, referred to below as plant health compositions.

A plant health composition/compound is a composition/compound comprising one or more natural or synthetic chemical substances, or biological organisms, capable of maintaining and/or promoting plant health. Such a composition/compound can improve plant health, vigor, productivity, quality of flowers and fruits, and/or stimulate, maintain, or enhance plant resistance to biotic and/or abiotic stressors/pressures.

Traditional plant health compositions and/or compounds include, but are not limited to, plant growth regulators (aka plant growth stimulators, plant growth regulating compositions, plant growth regulating agents, plant growth regulants) and plant activating agents (aka plant activators, plant potentiators, pest-combating agents). The plant health composition in the present invention can be either natural or synthetic.

Plant growth regulators include, but are not limited to, fertilizers, herbicides, plant hormones, bacterial inoculants and derivatives thereof.

Fertilizer is a composition that typically provides, in varying proportions, the three major plant nutrients: nitrogen, phosphorus, potassium known shorthand as N—P—K); or the secondary plant nutrients (calcium, sulfur, magnesium), or trace elements (or micronutrients) with a role in plant or animal nutrition: boron, chlorine, manganese, iron, zinc, copper, molybdenum and (in some countries) selenium. Fertilizers can be either organic or non-organic. Naturally occurring organic fertilizers include, but are not limited to, manure, worm castings, peat moss, seaweed, sewage and guano. Cover crops are also grown to enrich soil as a green manure through nitrogen fixation from the atmosphere by bacterial nodules on roots; as well as phosphorus (through nutrient mobilization) content of soils. Processed organic fertilizers from natural sources include compost (from green waste), bloodmeal and bone meal (from organic meat production facilities), and seaweed extracts (alginates and others). Fertilizers also can be divided into macronutrients and micronutrients based on their concentrations in plant dry matter. The macronutrients are consumed in larger quantities and normally present as a whole number or tenths of percentages in plant tissues (on a dry matter weight basis), including the three primary ingredients of nitrogen (N), phosphorus (P), and potassium (K), (known as N—P—K fertilizers or compound fertilizers when elements are mixed intentionally). There are many micronutrients, required in concentrations ranging from 5 to 100 parts per million (ppm) by mass. Plant micronutrients include iron (Fe), manganese (Mn), boron (B), copper (Cu), molybdenum (Mo), nickel (Ni), chlorine (Cl), and zinc (Zn).

Plant hormones a (aka phytohormones) and derivatives thereof include, but are not limited to, abscisic acid, auxins, cytokinins, gibberellins, brassinolides, salicylic acid, jasmonates, plant peptide hormones, polyamines, nitric oxide and strigolactones.

Plant activating agents are natural or synthetic substances that can stimulate, maintain, or enhance plant resistance to biotic and/or abiotic stressors/pressures, which include, but are not limited to, acibenzolar, probenazole, isotianil, salicyclic acid, azelaic acid, hymexazol, brassinolide, forchlorfenuron, benzothiadiazole (e.g., ACTIGARD® 50WG), microbes or elicitors derived from microbes, More plant activating agents are described in U.S. Pat. Nos. 6,849,576; 5,950,361; 6,884,759; 5,554,576; 6,100,092; 6,207,882; 6,355,860; 5,241,296; 6,369,296; 5,527,783; and 6,987,130.

Microbes, or chemical compounds and peptides/proteins (e.g., elicitors) derived from microbes, can also be used as plant activating agents. Non-limiting exemplary elicitors are: branched-β-glucans, chitin oligomers, pectolytic enzymes, elicitor activity independent from enzyme activity (e.g. endoxylanase, elicitins, PaNie), avr gene products (e.g., AVR4, AVR9), viral proteins (e.g., vial coat protein, Harpins), flagellin, protein or peptide toxin (e.g., victorin), glycoproteins, glycopeptide fragments of invertase, syringolids, Nod factors (lipochitooligo-saccharides), FACs (fatty acid amino acid conjugates), ergosterol, bacterial toxins (e.g., coronatine), and sphinganine analogue mycotoxins (e.g., fumonisin B1). More elicitors are described in Howe et al., *Plant Immunity to Insect Herbivores*, Annual Review of Plant Biology, 2008, vol. 59, pp. 41-66; Stergiopoulos, *Fungal Effector Proteins* Annual Review of Phytopathology, 2009, vol. 47, pp. 233-263; and Bent et al., *Elicitors, Effectors, and R Genes: The New Paragigm and a Lifetime Supply of Questions*, Annual Review of Plant Biology, 2007, vol. 45, pp. 399-436.

More non-limiting exemplary plant health compositions/compounds are described in U.S. Pat. Nos. 4,751,226; 4,889,551; 4,456,467; 5,763,366; 4,219,351; 4,394,151; 4,913,725; RE33976; 4,959,093; 6,645,916; 4,152,429; 4,462,821; 4,704,160; 3,979,201; 4,505,736; 4,422,865; 5,919,448; 4,431,442; 4,824,473; 4,185,990; 5,837,653; 4,701,207; 4,717,732; 4,716,174; 4,720,502; 4,717,734; 6,261,996; 4,701,463; 4,728,657; 4,636,514; 4,717,733; 4,731,372; 5,168,059; 4,261,730; 5,861,360; 4,066,435; 4,210,439; 5,006,148; 4,906,280; 4,160,660; 4,439,224; 5,123,951; 4094,664; 4,902,815; 4,036,629; 4,534,785; 4,212,664; 4,880,622; 4,144,047; 4,336,060; 4,308,054; 4,515,618; 4,525,200; 4,579,582; 5,554,580; 4,840,660; 4,268,299; 4,534,786; 5,589,438; 4,596,595; 5,468,720; 6,083,882; 6,306,797; 4,226,615; 4,509,973; RE29439; 4,025,331; 6,242,381; 4,326,878; 4,259,104; 5,518,994; 5,446,013; 3,713,805; 4,75,5213; 4,397,678; 4,762,549; 6,984,609; 4,808,207; 4,943,310; 4,481,026; 7,270,823; 4,592,772; 5,346,879; 5,627,134; 4,439,225; 4,931,082; 4,554,010; 4,057,413; 4,072,495; 4,364,768; 7,544,821; 5,523,275; 5,525,576; 7,404,959; 4,619,685; 4,157,255; 5,688,745; 6,569,809; 4,606,756; 4,537,623; 5,965,488; 4,243,405; 4,978,386; 5,654,255; 5,849,666; 7,078,369; 6,884,758; 5,076,833; 6,649,568; 4,954,157; 4,519,163; 4,154,596; 4,246,020; 4,356,022; 4,093,664; 4,808,209; 4,726,835; 4,879,291; 4,776,874; 4,892,576; 4,859,231; 4,130,409; 4,530,715; 4,936,907; 4,964,894; 4,921,529; 4,494,982; 5,228,899; 4,992,093; 4,059,431; 4,765,823; 4,059,432; 4,969,948; 6,750,222; 4,171,213; 5,668,082; 4,672,112; 4,067,722; 4,732,605; 5,481,034; 5,015,283; 4,812,159; 3,905,799; 4,371,388; 4,427,436; 4,293,331; 3,979,204; 5,436,225; 6,727,205; 4,148,624; 4,737,498; 3,938,983; 5,656,571; 4,863,505; 4,227,918; 4,595,406; 4,976,771; 4,857,545; 4,999,043; 3,960,539; 5,617,671; 3,912,492; 4,217,129; 4,170,462; 4,486,219; 5,801,123; 5,211,738; 4,067,721; 5,854,179; 4,285,722; 5,510,321; 6,114,284; 4,588,435; 7,005,298; 4,504,304; 4,451,281; 3,940,414; 5,925,596; 6,331,506; 4,391,629; 5,006,153; 4,857,649; 5,922,646; 5,922,599; 5,709,871; 4,741,768; 4,723,984; 4,752,321; 5,741,521; 5,700,760; 4,888,048; 4,113,463; 5,086,187; 4,711,658; 4,960,453; 4,846,883; 4,959,097; 5,371,065; 4,620,867; 5,154,751; 4,090,862; 6,906,006; 4,292,072; 4,349,377; 4,586,947; 4,239,528; 6,284,711; 4,043,792; 6,939,831; 5,030,270; 4,844,730; 6,410,483; 5,922,648; 6,069,114; 6,861,389; 4,806,143; 4,886,544; 4,923,502; 6,071,860; 5,131,940; 4,193,788; RE31550; 4,127,402; 4,799,950; 4,963,180; 4,337,080; 4,637,828; 4,525,203; 4,391,628; 4,908,353; 4,560,738; 4,685,957; 5,637,554; 5,312,740; 3,985,541; 4,770,692; 4,787,930; 4,240,823; 5,428,002; 6,458,746; 3,989,525; 5,902,772; 4,588,821; 4,681,900; 5,679,621; 6,995,015; 5,110,345; 5,332,717; 5,222,595; 5,351,831; 4,904,296; 4,104,052; 4,622,064; 4,902,332; 4,747,869; 5,053,072; 5,186,736; 4,349,378; 5,223,017; 4,889,946; 5,323,906; 5,529,976; 4,946,493; 4,961,775; 5,253,759; 4,311,514; 4,380,626; 5,635,451; 4,975,112; 5,658,854; 6,410,482; 7,479,471; 5,015,284; 4,925,480; 4,638,004; 4,124,369; 5,039,334; 5,090,992; 5,710,104; 4,909,832; 4,744,817; 4,764,202; 4,668,274; 4,547,214; 4,808,213; 4,507,140; 4,904,298; 6,316,388; 6,265,217; 5,869,424; 5,110,344; 4,330,322; 5,292,533; 4,047,923; 4,764,624; 4,560,403; 4,557,754; 5,346,068; 4,770,688; 5,073,185; 4,973,690; 4,772,309; 4,911,746; 4,594,094; 4,518,415; 4,786,312; 7,198,811; 6,376,425; 4,895,589; 4,960,456; 4,897,107; 4,891,057; 4,102,667; 5,763,495; 4,606,753; 4,602,929 4,740,231; 4,812,165; 5,324,710; 5,701,699; 6,465,394; 5,783,516; 4,334,909; 5,466,460; 5,559,218; 4,678,496; 5,679,620; 5,977,023; 7,326,826; 4,729,783; 4,377,407; 4,602,938; 5,211,736; 5,106,409; 4,802,909; 4,871,387; 4,846,873; 4,936,892; 5,714,436; 6,239,071; 4,507,141; 4,936,901; 5,026,418; 4,734,126; 4,999,046; 4,554,017; 4,554,007; 4,943,311; 4,401,458; 5,419,079; 4,789,394; 4,871,389; 5,198,254; 5,747,421; 5,073,187; 5,258,360; 4,153,442; 4,808,722; 4,565,875; 5,298,480; 4,233,056; 4,849,007; 5,112,386; 5,221,316; 5,470,819; 4,614,534; 4,615,725; 5,496,794; 4,772,310; 4,640,706; 4,894,083; 6,767,865; 5,022,916; 4,797,152; 4,957,535; 4,880,457; 4,735,651; 5,160,364; 4,647,302; 4,818,271; 5,710,103; 6,508,869; 5,858,921; 4,599,448; 4,938,791; 4,491,466; 4,812,162; 7,427,650; 4,684,396; 4,201,565; 4,636,247; 4,925,482; 4,486,218; 6,570,068; 5,045,108; 4,336,059; 4,983,208; 4,954,162; 4,921,528; 4,826,531; 4,661,145; 4,935,049; 4,515,619; 4,810,283; 4,988,382; 4,584,008; 4,227,915; 4,875,922; 4,988,383; 4,886,545; 5,602,076; 4,229,442; 4,525,201; 5,034,052; 5,104,443; 3,620,919; 4,164,405; 5,703,016; 5,102,443; 4,618,360; 6,569,808; 4,919,704; 4,584,013; 4,775,406; 5,631,208; 4,909,835; 4,178,166; 4,183,742; 6,225,260; 5,318,945; 4,623,382; 5,053,073; 4,693,745; 4,875,930; 5,696,053; 4,221,584; 4,975,459; 4,601,746; 4,185,991; 4,871,390; 4,863,503; 5,073,184; 5,262,389; 5,061,311; 4,966,622; 6,228,808; 5,057,146; 4,849,009; 4,939,278; 4,481,365; 4,333,758; 4,741,754; 4,411,685; 4,455,162; 7,291,199; 5,252,542; 4,470,840; 4,227,911; 4,959,093; and 5,123,951. Each of the patents, patent publications cited here is incorporated by reference in its entirety herein, including all drawings/photographs that are a part thereof.

Bacterial inoculants are compositions comprising beneficial bacteria that are used to inoculate soil, often at the time of planting. Such bacterial inoculants include nitrogen-fixing bacteria or *rhizobia* bacteria. *Bradyrhizobia japonicum* is commonly used for soybean inoculation and *Bradyrhizobia* sp. (Vigna) or (Arachis) for peanuts. Other *rhizobia* are used with other crops: *Rhizobium leguminosarum* for peas, lentils and beans and alfalfa and clover and *Rhizobium loti, Rhizobium leguminosarum* and *Bradyryizobium* spp. for various legumes. In one embodiment, the compositions of the present invention are mixed with or further comprise at least one bacterial inoculant and then applied to soil or to seed. In another embodiment, the compositions and bacterial inoculant are applied to a plant, a plant part or the locus of the plant or plant part at the same time or sequentially.

In some embodiments, the compositions of the present invention are mixed with, further comprise, or are applied at the same time as or as part of a spray program with insecticides. Suitable insecticides include neonicotinoid insecticides such as 1-(6-chloro-3-pyridylmethyl)-N-nitroimidazolidin-2-ylideneamine(imidacloprid), 3-(6-chloro-3-pyridylmethyl)-1,3-thiazolidin-2-ylidenecyanamide (thiacloprid), 1-(2-chloro-1,3-thiazol-5-ylmethyl)-3-methyl-2-nitroguanidine (clothianidin), nitempyran, N.sup.1-[(6-chloro-3-pyridy)methyl]-N.sup.2-cyano-N.sup.1-methylacetamid-ine(acetamiprid), 3-(2-chloro-1,3-thiazol-5-ylmethyl)-5-methyl-1,3,5-oxadiazinan-4-ylidene(-nitro) amine(thiamethoxam) and 1-methyl-2-nitro-3-(tetrahydro-3-furylmethyl)guanidine (dinotefuran).

In some embodiments in which the compositions are used to control nematodes, the compositions further comprise or are mixed with or are applied at the same time as or as part of a treatment program with at least one other nematicide. The term "nematicide," as used herein, includes nematode control agents, such as those that kill nematodes and those that inhibit nematode growth and/or development. The second nematicide may be a chemical or a biological nematicide. The term "chemical nematicide," as used herein, excludes fumigants, and the term "fumigants" encompasses broad spectrum pesticidal chemicals that are applied to soil pre-planting and that diffuse through the soil (in soil air and/or soil water) and may be applied as gases, such as methyl bromide, volatile liquids, such as chloropicrin, or volatile solids, such as dazomet.

In some embodiments, the chemical or biological nematicide is a commercially available formulated product and is tank mixed with the compositions of the present invention. In other embodiments, the chemical or biological nematicide is mixed with the *Bacillus*-based compositions of the present invention prior to formulation so that the active components ultimately form one formulated product.

Chemical nematicides used in such mixtures are carbamates, oxime carbamates, and organophosphorous nematicides. Carbamate nematicides include benomyl, carbofuran, (FURADAN®), carbosulfan and cloethocarb. Oxime carbamates include alanycarb, aldicarb (TEMIK® or as part of the AVICTA® Complete Pak seed treatment from Syngenta), aldoxycarb (STANDAK®), oxamyl (VYDATE®), thiodicarb (part of the AERIS® seed-applied system from Bayer CropScience), and tirpate. Organophosphorous nematicides include fensulfothion (DANSANIT®), ethoprop. (MOCAP®), diamidafos, fenamiphos, fosthietan, phosphamidon, cadusafos, chlorpyrifos, dichiofenthion, dimethoate, fosthiazate, heterophos, isamidofos, isazofos, phorate, phosphocarb, terbufos, thionazin, triazophos, imicyafos, and mecarphon. Parenthetical names following each compound are representative commercial formulations of each of the above chemicals. Other chemical nematicides useful for such mixtures include spirotetramat (MOVENTO®), MON37400 nematicide and fipronil.

Biological nematicides include chitin and urea mixtures; compost extracts and teas (both aerated and nonaerated); compositions comprising the fungus *Myrothecium verrucaria* and/or metabolites therefrom (commercially available as DITERA®); compositions comprising the fungus *Paecilomyces*, including *P. lilacinus* (commercially available as, for example, MELOCON® or BIOACT®); the bacterium *Pasteuria*, including *P. usgae*, compositions comprising such bacterium (commercially available as, for example, ECONEM®); bacteria from the *Bacillus* sp., including *Bacillus firmus* (including CNMC I-1582, deposited with the Collection Nationale de Cultures de Microorganismes, Institute Pasteur, France on May 29, 1995 and commercially available as, for example, VOTIVO), *Bacillus subtilis*, *Bacillus amyloliquefaciens*, *Bacillus pumilus* (including the strain deposited with NRRL as No. B-30087 on Jan. 14, 1999, and its mutants) and *Bacillus cereus* and compositions comprising one or more of the above bacteria; nematicidal *Streptomycete* sp., such as *Streptomyces lydicus* and compositions comprising such bacteria (commercially available as ACTINOVATE®) and nematophagous fungi, including *Duddingtonia flagrans*, such as strain T-89, deposited in the collection of microorganisms of GNC VB "Vector" (Koltsovo settlement, Novosibisrsk region) under No. F-882, *Paecilmyces lilacinus*, and *Arthrobotrys oligospora*. Biological nematicides also include botanically-based nematicides such as products based on neem plants (including seeds or oil from the plants) or azidirachtin, a secondary metabolite of neem seeds, sesame oil-based products (such as DRAGONFIRE®), carvacrol, and products based on plant extracts (such as NEMA-Q®, obtained from the *Quillaja saponaria* tree of Chile). Biological nematicides also include isolated compounds produced by bacteria, such as the mectins, a family of chemical compounds which are produced by *Streptomyces avermentilis*, including abamectin (consisting of a combination of abamectin $B_{1a}$ and $B_{1b}$) and avermectin $B_{2a}$, and the harpin proteins, originally identified in *Erwinia amylovora*, including harpin$_{EA}$ and harpin$_{\alpha\beta}$.

*Bacillus*-based compositions of the present invention may be applied independently or in combination with one more other chemical and non-chemical fungicides, insecticides, miticides, nematicides, fertilizers, nutrients, minerals, auxins, growth stimulants and/or plant health products. In some embodiments, the swrA⁻ cells are co-formulated with at least one fungicide, insecticide, miticide, nematicide, fertilizer, nutrient, mineral, auxin, growth stimulant and/or other plant health product and the co-formulated product is applied to the plant, plant part, or plant locus. In some other embodiments, the compositions of the present invention are tank mixed with commercially available formulations of the fungicide, insecticide, miticide, nematicide, fertilizer, nutrient, mineral, auxin, growth stimulant and/or other plant health product and applied to plant, plant parts and/or plant loci. In other embodiments, the compositions of the present invention are applied to plants, plant parts, and/or plant loci immediately before or after application of commercially available formulations of the fungicide, insecticide, miticide, nematicide, fertilizer, nutrient, mineral, auxin, growth stimulant and/or other plant health product. In other embodiments, the compositions of the present invention are applied to plants, plant parts and/or plant loci in rotation with the commercially available formulations of the fungicide, insecticide, miticide, nematicide, fertilizer, nutrient, mineral, auxin, growth stimulant and/or other plant health product. In one instance, the *Bacillus subtilis*-based compositions are applied as a seed treatment or as an in-furrow or drench treatment, as discussed in more detail herein. In some instances of the above embodiments, the commercially available formulations of the fungicide, insecticide, miticide, or nematicide are applied at a rate that is less than the rate recommended on the product label for use of such fungicide, insecticide, miticide, or nematicide as a stand-alone treatment. In one aspect of this embodiment, the fungicide, insecticide, miticide and/or nematicide is a chemical. In yet another aspect, the chemical is one that has toxicity issues and may also be undergoing a "phase out" by relevant governmental agencies in one or more countries.

In other embodiments, the compositions of the present invention are applied to plants, plant parts and/or plant loci following application of a fumigant. Fumigants can be applied by shank injection, generally a minimum of 8 inches below the soil surface. Liquid formulations of fumigants can also be applied through surface drip chemigation to move the fumigant to a depth of 8 inches or more below the soil surface. Treated soil beds are covered with a plastic tarp to retain the fumigant in the soil for several days. This is done before planting and allowed to air out prior to planting. The *Bacillus*-based compositions described herein would be applied after such air-out period either prior to, at the time of, or post-planting. In some instances, the fumigants are applied at a rate that is less than the rate recommended on the product label.

Fumigants, including fumigant nematicides, include halogenated hydrocarbons, such as chloropicrin (CHLOR-O-PIC®), methyl bromide (METH-O-GAS®) and combinations thereof (such as BROM-O-GAS® and TERR-O-GAS®), 1,3-dichloropropene (TELONE® II, TELONE® EC, CURFEW®) and combinations of 1,3-dichloropropene with chloropicrin (TELONE® C-17, TELONE® C-35, and INLINE®), methyl iodide (MIDAS®); methyl isocyanate liberators, such as sodium methyl dithiocarbamate (VA-PAM®, SOILPREP®, METAM-SODIUM®); combinations of 1,3 dichloropropoene and methyl isothiocyanate (VORLEX®); and carbon disulfide liberators, such as sodium tetrathiocarbonate (ENZONE®) and dimethyl disulphide or DMDS (PALADINO®). Commercial formulations of each of the above fumigants are provided in parentheses after the chemical name(s).

Compositions of the present invention may also be applied as part of an integrated pest management ("IPM") program. Such programs are described in various publications, especially by university cooperative extensions. As to nematodes, such programs include crop rotation with crops that cannot host the target nematode, cultural and tillage practices, and use of transplants. For example, the *Bacillus*-based compositions described herein could be applied after a season of growth with mustard or other nematode suppressive crop.

In some embodiments, application of the compositions of the present invention to plants, plant parts or plant loci is preceded by identification of a locus in need of treatment. For nematode control, such identification may occur through visual identification of plants that appear chlorotic, stunted, necrotic, or wilted (i.e., that appear to have nutrient deficiencies) typically coupled with knowledge of a history of nematode problems; plant sampling; and/or soil sampling. Plant sampling may occur during the growing season or immediately after final harvest. Plants are removed from soil and their roots examined to determine the nature and extent of the nematode problem within a field. For root knot nematodes, root gall severity is determined by measuring the proportion of the root system which is galled. Galls caused by root knot nematodes may be distinguished from nodules of nitrogen-fixing soil bacteria because galls are not easily separated from the root. Root knot nematode soil population levels increase with root gall severity. In some instances, the detection of any level of root galling suggests a root knot nematode problem for planting any susceptible crop, especially in or near the area of sampling. Cyst nematodes may also be identified by plant sampling and scrutiny of roots for cysts.

Soil sampling offers a means to determine the number of nematodes and/or nematode eggs infesting a certain volume of soil or roots. Soil sampling may be conducted when a problem is first suspected, at final harvest, or any time prior to planting a new crop, including prior to crop destruction of the previous crop. University cooperative extension programs offer soil sampling services, including the University of Florida, Oregon State University and the University of Nebraska-Lincoln. In addition, such programs provide guidance for how to collect samples. For example, in one method of post-harvest predictive sampling, samples are collected at a soil depth of 6 to 10 inches from 10 to 20 field locations over 5 or 10 acres (depending on value of the crop, with fewer acres sampled for higher value crops) in a regular zigzag pattern. In a method of testing established plants, root and soil samples are removed at a soil depth of 6 to 10 inches from suspect plants that are symptomatic but that are not dead or dying; i.e., decomposing.

In some embodiments, identification involves determining whether an economic threshold of a pest, such as a nematode, has been reached; i.e., a point at which expected economic losses without treatment exceed treatment costs. The economic threshold varies depending on the crop, geography, climate, time of planting, soil type, and/or soil temperature. Numerous papers have been published on this topic and guidelines are available from university cooperative extension programs in different areas. See, for example, Robb, J. G., et al., "Factors Affecting the Economic Threshold for *Heterodera schachtii* Control in Sugar Beet," Economics of Nematode Control January-June 1992; Hafez, Saad L. "Management of Sugar Beet Nematode," University of Idaho Current Information Series (CIS) 1071 (1998); and *UC IPM Pest Management Guidelines: Tomato* UC ANR Publication 3470 Nematodes A. Ploeg, Nematology, UC Riverside (January 2008). Determining the economic threshold for a particular crop at a particular time of year is well within the skill set of one of ordinary skill in the art.

In some embodiments, the soil sampling reveals that the nematode infestation will cause yield that is about 80%, about 90%, or about 95% of normal for uninfested soil.

In some embodiments, the economic threshold of root knot juveniles per kilogram of soil sample is at least about 250, at least about 300, at least about 500, at least about 750, at least about 1000, at least about 2000, at least about 3000, at least about 4000, at least about 5000, or at least about 6000.

In some embodiments, the economic threshold of cyst nematode eggs and larvae per 1 $cm^3$ soil is at least about 0.5, at least about 1, at least about 2, at least about 3, at least about 4. According to Hafez (1998), supra, a cyst may be estimated as 500 viable eggs and larvae.

The present invention also encompasses a method for identifying and/or producing a plant growth enhancing bacterial product by screening cells of a *Bacillus* species within the *Bacillus subtilis* clade, selecting cells with a mutation in the swrA gene; and producing a fermentation product with cells with the swrA⁻ mutation. In some embodiments screening entails plating a *Bacillus* species, choosing individual bacterial colonies, isolating DNA from each colony, and sequencing the swrA gene using primers based on the swrA sequences provided in FIG. 5. Appropriate PCR conditions will be known by those of ordinary skill in the art. Exemplary primers and PCR conditions are set forth in Example 24.

In some embodiments, the screening is preceded by growing the cells and selecting the cells with one of more of the following characteristics: the sandpaper morphology or impaired swarming ability compared to wildtype cells. Swarming ability may be assessed in the same way as described in Example 7.

In other embodiments, the selecting step also involves selecting those cells with a mutation in the swrA gene that have enhanced capability to improve plant health compared to wildtype cells. In one aspect, this involves applying the fermentation product to a plant, to a part of the plant and/or to a plant locus and comparing the growth of the plant with a reference plant to which no such fermentation product is applied and/or to a reference plant to which fermentation product from isogenic cells not having the mutation is applied.

In still other embodiments, the screening involves screening for a mutation in the swrA gene that corresponds to positions 1-3 or to positions 26-34 of SEQ ID NO. 1.

The selected swrA⁻ cells may have any of the mutations described herein in the description of various swrA mutations.

The present invention also encompasses a method for screening for a plant growth enhancing bacterial product comprising (i) mutating a wildtype swrA gene of bacterial cells from a *Bacillus* species in the *Bacillus subtilis* clade to create a mutant bacterial cell; (ii) growing the mutant bacterial cell and characterizing its specific cell morphology; (iii) growing a population of the bacterial cells from the *Bacillus* species in the *Bacillus subtilis* clade having a wildtype swrA gene on a solid surface, such as agar; and (iv) selecting the bacterial cells with the cell morphology identified in step (ii), above. In some embodiments, the swrA mutant is created by antisense or transposon technology. Specific examples are provided in Example 25.

In another embodiment, the present invention encompasses a method for producing a plant growth promoting product comprising:

a. culturing a bacterial cell comprising a mutation in a swrA gene or an ortholog thereof wherein the mutation reduces swarming ability of the cell when grown on a solid or non-liquid surface compared to a bacterial cell not having the mutation and b. growing the bacterial cells having the mutation to sporulation.

In another aspect, the method further comprises drying the bacterial cells from step (b). In yet another aspect, the method further comprises adding a carrier or formulation inert. In still another embodiment, the growing step occurs in a biofermentor. In some embodiments, the biofermentor has at least a 2 L capacity.

DEPOSIT INFORMATION

A sample of QST713 wild type swrA⁺, QST30002 (aka AQ30002) and QST30004 (aka AQ30004) have been deposited with the Agricultural Research Service Culture Collection located at the National Center for Agricultural Utilization Research, Agricultural Research Service, U.S. Department of Agriculture, 1815 North University Street, Peoria, Ill. 61604. QST713 wild type swrA⁺ (deposited on Oct. 5, 2010) has been assigned the following depository designation: NRRL B-50420. QST30002 (deposited on Oct. 5, 2010) has been assigned the following depository designation: NRRL B-50421. QST30004 (deposited on Dec. 6, 2010) has been assigned the following depository designation: NRRL B-50455.

To satisfy the enablement requirements of 35 U.S.C. §112, and to certify that the deposit of the bacterial strains of the present invention meets the criteria set forth in 37 C.F.R. §§1.801-1.809, Applicants hereby make the following statements regarding the deposited *Bacillus subtilis* strains QST713 wild type swrA⁺, QST30002 and QST30004 (deposited as NRRL Accession Nos. B-50420, B-50421 and B-50455):

1. During the pendency of this application, access to the invention will be afforded to the Commissioner upon request;
2. Upon granting of the patent the bacterial strains will be available to the public under conditions specified in 37 CFR 1.808;
3. The deposit will be maintained in a public repository for a period of 30 years or 5 years after the last request or for the enforceable life of the patent, whichever is longer;
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, subject to paragraph (b) of 37 CFR 1.808 all restrictions on the availability to the public of the bacterial strains will be irrevocably removed.

The following examples are given for purely illustrative and non-limiting purposes of the present invention.

EXAMPLES

Example 1

Identification of Sandpaper Mutant Morphology

The first *Bacillus subtilis* cells with sandpaper morphology were unexpectedly identified and isolated during a routine quality control (QC) assay of commercial batches of SERENADE®.

The sandpaper variants presented a different colony morphology on nutrient agar culture plates than did the QST713 wild type cells. The sandpaper cells formed highly compacted and hydrophobic colonies on the solid medium (see images of QST713 wild type and sandpaper colonies taken with a Keyence Digital Microscope in FIG. 1). The "sandpaper" name was given to these variants because their phenotype presents flat dry colonies that are compact, very "crispy" and very hard to remove from the agar on which they are grown (i.e., very adherent colonies). From this initial discovery a single strain with the sandpaper morphology was initially isolated and selected for further characterization. This strain was designated AQ30002.

In addition to having a distinct colony morphology on solid medium, AQ30002 was also observed to form long chains of cells in liquid culture during early exponential phase. In contrast, QST713 wild type cells formed short chains or remained as single cells during this same stage of growth (compare microscopic images in FIG. 2).

Figure 3:
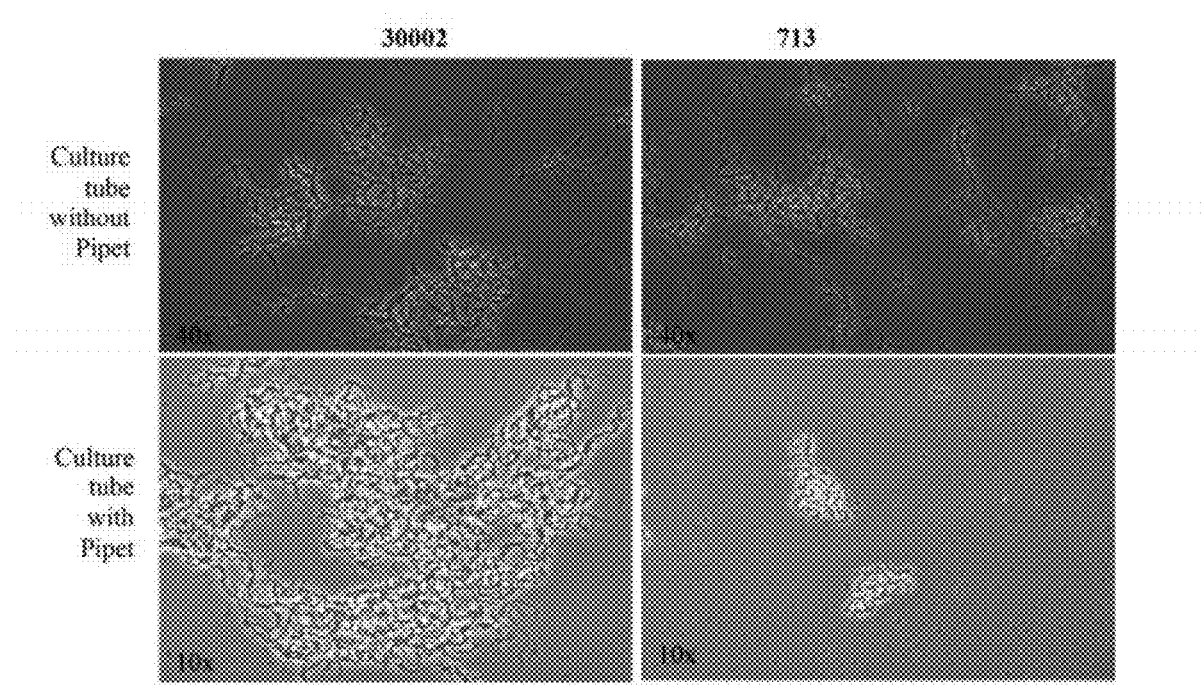
FIG. 3 shows images of AQ30002 swrA⁻ ("30002") and QST713 wild type swrA⁺ cells ("713") in liquid culture subject to shear forces. The top images show cell growth without a pipet tip inserted into the culture medium at 40× magnification, while the bottom images show cell growth with a pipet tip inserted into the culture medium at 10× magnification.

AQ30002 also exhibits a distinct morphological response to growth in high shear liquid culture. AQ30002 and QST713 show very similar morphology and growth habits when grown in liquid culture with shaking; however, if an object (e.g., plastic pipette tip) is placed in the tube, the increased turbulence produced by the movement of this object within the culture appears to trigger a morphological shift in AQ30002 only, preventing the separation of vegetative cells after division (chaining) and producing large clumps of filaments. This phenotype can be observed both microscopically and by direct observation of the culture tubes after 8-9 hours of growth. Compare images provided in FIG. 3, which were obtained as follows. Glycerol culture stocks of AQ30002 and QST713 wild type were grown over night on nutrient agar plates. One colony from each plate was placed individually into 3 mL of Luria Broth in an 8 mL snip cap tube and a 1 mL DNAse-free pipet tip was placed in the inoculated tube. One colony from each plate was also grown under the same conditions in a tube without a pipet tip. The tube was shaken at 37° C. at 260 rpm and growth compared after 8-9H using light microscopy.

A number of *Bacillus* genes (e.g., sinR) have been previously identified as activators of biofilm production or (when mutated) as constitutive biofilm producers. Based on personal communication from Dan Kearns (Indiana University), sinR mutants are "clumpy" when grown in liquid culture, consistent with the idea that this mutant is producing biofilm at all times independent of environmental signals. This property would not be desirable for commercial development and in general suggests that downstream, effector genes in biofilm production, such as SinR, would not be good commercial candidates.

In contrast, swrA appears to be part of a natural cellular switch that allows Bacillus cells to adjust to their environment. Although swrA has not been previously described as a biofilm regulator, it has been recognized for its role in shifting cells between two distinct morphological states in liquid culture: single planktonic cells or chains of connected cells (Kearns and Losick, "Cell Population Heterogeneity During Growth of *Bacillus subtilis*", Genes and Development (2005): 19, pp 3083-3094.) Consistent with this report, swrA mutant cells are still responsive to environmental signals. When grown in liquid culture, these cells grow as single cells or chains, but do not appear to clump or form biofilm. Unexpectedly, when grown on roots or solid culture medium, these cells turn on the production of dense compact biofilm. This is consistent with the idea that swrA is a normal genetic switch that shifts cells to the ability to produce a distinct type of biofilm and (because it acts early in the pathway) still allows cells to respond to environmental signals (e.g., non-adherent growth in liquid culture and biofilm formation when grown on solid media).

Example 2

Preparation of *Bacillus subtilis* QST713 Whole Broth in Bioreactors

It was observed that cultures of *Bacillus subtilis* QST713 grown in bioreactors contain some small proportion of sandpaper variant cells. Culture stocks of *Bacillus subtilis* QST713 are maintained frozen in small vials of glycerol solution. To produce whole broth in a bioreactor, a vial of stock culture is thawed and the contents are transferred to a sterilized flask of appropriate culture medium such as Difco Nutrient Broth. The flask culture is incubated on a rotary shaker under conditions which promote the growth of the organism typically at temperatures between 25° C. and 37° C. with a rotation speed of 100 to 250 rpm. When the cell density in the flask is sufficiently high, the contents are transferred to fresh sterilized growth medium in a bioreactor.

The bioreactor is controlled with specific temperature, agitation, pH, and aeration to promote the growth of the organism and the expression of active metabolites. Typical bioreactor settings include a temperature setting between 25° C. and 37° C., an agitation setting of 200 to 1000 rpm, a pH buffered to stay somewhere between 6 and 8, and aeration set between 0.2 and 1.0 VVM. When cell growth and metabolite production has ceased, typically within 24 to 72 hours of incubation, the culture broth is harvested and then assayed for cell count and purity. After these tests are complete and accepted, the broth may be used in laboratory experiments.

Alternatively, preservatives and other additives (such as thickeners and dispersants) may be mixed into the bioreactor broth to simulate commercial product for field trial experiments.

Example 3

Quantification of Sandpaper Mutation Frequency in *Bacillus subtilis* QST713

Various commercial lots of SERENADE® ASO produced by AgraQuest, Inc. (Davis, Calif.) were diluted (1/10E+6) and plated on Nutrient Agar (NA) to resolve individual colonies. The sandpaper-like colonies were confirmed as being mutants of QST713 wild type by 16S rDNA sequencing.

The number of sandpaper colonies was quantified as a percentage of the total number of colonies produced. Sandpaper colonies with the characteristic colony morphology were obtained at frequencies varying from 0.0% to 1.3% from the commercial lots of SERENADE® ASO analyzed (see FIG. 4) and from 0.0% to 3.2% from the commercial lots of SERENADE® MAX analyzed.

As discussed above, the EPA Master Label for SERENADE® MAX specifies that the commercial product contains 14.6% of dried QST713. If a commercial sample of SERENADE® MAX contains at most 14.6% of dried QST713 wild type/sandpaper and if at most only 3.2% of that is the swrA variant, then the commercial samples of SERENADE® MAX contain at most (0.146×0.032)=0.004672=0.4672% or less than 0.5% of the dried sandpaper variants (i.e., swrA⁻).

QST713 cells deriving from a single colony with wild type morphology were also grown in flasks overnight in Luria Broth, diluted and plated on nutrient agar in order to obtain individual colonies. Sandpaper colonies were identified and the frequency of mutation calculated to be 1/16,000. This is orders of magnitude higher than the spontaneous loss of function frequency for other genes and is consistent with the idea that swrA is a hypermutable phase variation locus (D. B. Kearns et al., "Genes Governing Swarming in *Bacillus subtilis* and Evidence for a Phase Variation Mechanism Controlling Surface Motility", Molecular Microbiology (2004), 52:357-369). The nucleotide sequence of the swrA gene from 6 individual sandpaper colonies was sequenced. All six colonies were found to be swrA negative. We therefore infer that, in QST713, all sandpaper colonies are swrA negative.

Example 4

Quantification of Sandpaper-Like Mutant Frequency in Commercial *Bacillus* Strains Various additional commercial biopesticide products containing *Bacillus* strains were also analyzed to determine whether cells with sandpaper-like morphology could be identified. As used herein, "sandpaper-like" or "sp-like" refers to a cell having a colony morphology similar to the colony morphology of QST713 sandpaper cells (see, e.g., FIG. 1) when grown on agar nutrient.

The commercial strains were grown in liquid culture, diluted, and plated on Nutrient Agar (NA) to resolve individual colonies as set forth in Example 2. The frequencies of sandpaper-like colonies in these commercial products varied between 0% and 0.7% (see Table 2).

TABLE 2

Frequency of Sandpaper-like Cells in Representative *Bacillus*-Based Commercial Biopesticides

| Commercial Product | Species | Number of Colonies | Number of Sandpaper-like Colonies | % of Sandpaper-like Colonies |
|---|---|---|---|---|
| Kodiak | GB03; *B. subtilis* | 8,096 | 4 | 0.0494 |
| Companion | GB03; *B. subtilis* | 2,957 | 0 | NA |
| Taegro | FZB24; *B. amyloliquefaciens* | 19,272 | 5 | 0.0259 |
| Rhizovital | FZB42; *B. amyloliquefaciens* | 3,784 | 8 | 0.2114 |

TABLE 2-continued

Frequency of Sandpaper-like Cells in Representative
Bacillus-Based Commercial Biopesticides

| Commercial Product | Species | Number of Colonies | Number of Sandpaper-like Colonies | % of Sandpaper-like Colonies |
|---|---|---|---|---|
| FolioActive | KTSB; *B. subtilis* | 27,984 | 2 | 0.0071 |
| Yield Shield | GB34; *B. pumilus* | 818 | 6 | 0.7335 |

The colony morphology most observed for the non-sandpaper-like colonies are as follows:
Kodiak ®—shiny, raised center with ruffled edges.
Companion ®—raised, 3D translucent center, crinkly edges; alternative phenotype (i.e., morphology) other than this wild-type were observed as a big mass.
Taegro ®—round, raised center with rough uneven edges; also observed 3 QST713 wild type-like colonies.
Rhizovital ®—plateau-like; dense, raised center, not shiny.
FolioActive ®—shiny, raised center with ruffled edges; not as much variability as Kodiak ®; also observed 2 QST713 wild type-like colonies.
Yield Shield ®—raised center with flat surrounding edges, small ring of bubbles within surrounding edge; also observed 4 QST713 wild type-like colonies.

We analyzed the swrA gene in all sandpaper-like variants of these commercial products, and, unexpectedly, all were wild type (swrA$^+$). In cells other than QST713, the sandpaper morphology, by itself, is not sufficient to predict the swrA$^-$ mutation and enhanced plant health improvement capabilities.

Example 5

Identification of Genetic Mutation Responsible for Sandpaper Morphology

Whole genome shotgun sequencing of multiple isolates of QST713 variants with the sandpaper morphology was used to identify the genetic mutation(s) responsible for the sandpaper phenotype. In addition to the original AQ30002 isolate derived from QST713, four additional QST713 mutants exhibiting the sandpaper phenotype (i.e., AQ30003, AQ30004, AQ30005, and AQ30006) were sequenced.

Using next-generation sequencing technology provided by Illumina (San Diego, Calif.), sequence reads totaling approximately 70× coverage of each isolate's genome were generated and aligned to the reference QST713 wild type genome.

Published tools for mutation detection, such as MAQ (Li, H., et al., "Mapping Short DNA Sequencing Reads and Calling Variants Using Mapping Quality Scores," Genome Res. (2008) 18, 1851-1858) and BWA (Li, H. and Durbin R., "Fast and Accurate Short Read Alignment with Burrows-Wheeler Transform," Bioinformatics (2009) 25, 1754-1760) were leveraged to identify potential sites of mutation. The following statistical and biological based assumptions were used to filter out false positives:

1. It is highly unlikely for all five sandpaper isolates (i.e., AQ30002-AQ30006) to exhibit the same mutation exactly in the same location.
2. If all five isolates exhibited the exact same mutation, it is most likely due to a sequencing error in the reference genome.
3. Sandpaper phenotype is most likely caused by a single mutation in one gene.
4. Mutation is likely to be in a coding region.
5. Mutation is likely to cause a drastic change to protein. A single base change was considered if it changed the affected codon to a stop codon or if it changed the start codon to a non-start codon. Insertions and deletions were considered if they caused a frameshift mutation
6. Mutation is not likely to be in an essential gene.

By incorporating the above assumptions into an analysis pipeline, swrA was identified as the only candidate gene for the mutation in the QST713 cells with the sandpaper morphology.

The swrA mutant alleles identified in the sandpaper variants sequenced above were subsequently confirmed by Sanger sequencing (Sanger, F., et al., "DNA Sequencing with Chain-Terminating Inhibitors," Proc. Natl. Acad. Sci. USA (1977) 74, 5463-5467) of this region from the individual isolates. A sequence alignment comparing the predicted swrA transcripts from representative sandpaper isolates AQ30002 and AQ30004 and from various wild-type *Bacillus* strains including QST713 is shown in FIG. 5.

Sanger resequencing confirmed that the swrA sequence in QST713 matched the reference sequence generated by next generation sequencing. FIG. 5 compares the predicted coding sequences of interest to the predicted coding sequence of swrA for Bsub_3610, which is a standard known to those skilled in the art of *Bacillus* genetics.

This analysis also verified that AQ30002, AQ30003, and AQ3006 all contain a 1 bp deletion in swrA resulting in a frame shift and a premature stop codon (see AQ30002 in FIG. 5) and that in AQ30004 and AQ30005 the swrA start codon is mutated to another (non-start) codon (see AQ30004 in FIG. 5).

Figure 6:
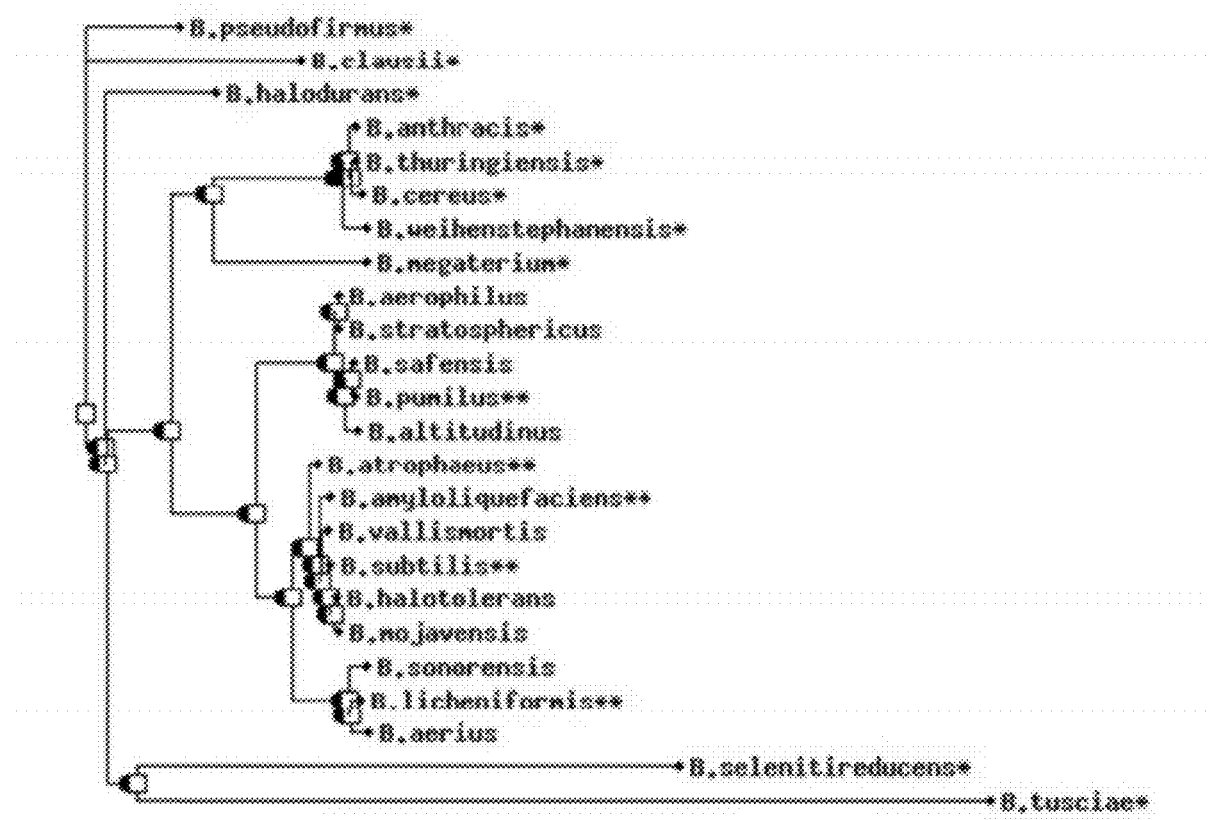
FIG. 6 shows a phylogenetic tree of species within the *Bacillus subtilis* clade (i.e., *B. subtilis* and all near relatives as assessed by 16S rDNA comparison) with more distantly related species included to root the tree. Species for which the complete genome sequence is available are marked with asterisks. A single asterisk ("*") further indicates that the species lacks an ortholog of swrA, while species marked with a double asterisk ("**") contain a swrA ortholog. The other unmarked species within the *B. subtilis* clade are presumed to have swrA orthologs based on their close phylogenetic relationship, but genomic sequence data for these species is currently not publicly available.

Orthologs of swrA are only present in a handful of species within the *Bacillus* genus. To identify members within the *Bacillus subtilis* clade likely to have a swrA gene, full length 16S rRNA genes from each of the closely related *Bacillus* species were aligned using ClustalW, a multiple sequence alignment program. The ClustalW alignment was then converted to PHYLIP format to generate a phylogenetic tree (see FIG. 6). Public genomic databases were then queried to identify which species had confirmed swrA ortholog sequences, and these species (i.e., *B. pumilus, B. atrophaeus, B. amyloliquefaciens, B. subtilis* and *B. licheniformis*) are indicated with a double asterisk in FIG. 6. SwrA is an unusually distinct protein with no related proteins identifiable outside this group, nor any predicted function. Because this group of *Bacillus* species (*B. subtilis* clade) is monophyletic by 16S rDNA comparison and the swrA gene is present in all 4 branches of the clade, we conclude that this gene arose early in this lineage and most likely is present in all species within the group.

Kearns, et al. ("Genes Governing Swarming in *Bacillus subtilis* and Evidence for a Phase Variation Mechanism Controlling Surface Motility," Molecular Microbiology (2004) 52(2):357-369) identified two potential start codons, TTG and GTG. GTG is 35 bases upstream of TTG. After independently mutating each codon, they observed that only the mutated TTG abolished expression from the downstream reporter and concluded that this was the true start codon. We note that there is a disagreement in the literature regarding predictions for the translation start codon for swrA (for example, swrA translation start is predicted herein to be 75 bp upstream (FIG. 5) for *Bacillus subtilis* subsp. *subtilis* strain NCIB 3610 swrA gene at GenBank ID ABV89964.1; also see cited therein, Zeigler, et al., 2008, "The Origins of 168, W23, and Other *Bacillus subtilis* Legacy Strains," J. Bacteriol. 190 (21):6983-6995). Furthermore, the predicted start codon in Kearns, et al. (2004, ibid) is non-canonical. We therefore performed a comparative sequence analysis across multiple species of the *B. subtilis* clade. Because gene structure is known to be well conserved among closely related species such as the *B. subtilis* clade, this method provides strong confirmation of gene features such as translation start site or location of key gene regulatory sequences.

We compared up to 100 bases upstream of the TTG start codon reported herein in the strains QST713 wild type, FZB42 (*B. amyloliquefaciens*), AQ2808 (*B. pumilus*) and *B. subtilis* subsp. *Spizizenii* (Genbank ID NC_014479). We found that there were no other start codons, ATG or alternatives that produced a reading frame generating a swrA polypeptide other than with the TTG start codon reported herein. As is known by those skilled in the art of bacterial genetics, many contingency loci, of which swrA appears to be one, use alternative start codons. See, for example, Annu. Rev. Genet. (2006) 40:307-33. Therefore, we conclude that the true translation start is at the TTG codon as predicted by Kearns, et al.

Example 6

Successive Passages of QST713 Sandpaper Cells

The QST713 sandpaper mutants with a deletion in the swrA genetic sequence (e.g., AQ30002) were stable after 15 passages in flasks in Trypticase Soy Broth (TSB) Medium (17 g/L pancreatic digest of casein, 3 g/L papaic digest of soybean meal, 5 g/L sodium chloride, 2.5 g/L dipotassium phosphate, 2.5 g/L dextrose). No QST713 wild type revertant cells were found when sandpaper cells were plated on NA after being transferred 15 times in flasks. These results demonstrate that the sandpaper mutant is stable and breeds true-to-form.

Example 7

Complementation Analysis of swrA in AQ30002

Methods

Studies were conducted to confirm that the swrA− mutation is responsible for the enhanced plant growth phenotype. Two constructs containing the swrA gene and the swrA gene plus 300 nucleotides upstream of the coding region and designated pPen_swrA (i.e., the swrA gene under the transcriptional control of a constitutive promoter) and endoPro_swrA (i.e., the swrA gene under the transcriptional control of its own promoter), respectively, were generated from QST713 swrA+ genomic DNA, using primers that contain restriction enzyme sites for subcloning the DNA fragments into a plasmid vector designed to be compatible with the Integrative and Conjugative Element (ICE) element present in *Bacillus subtilis* MMB869 (Wiep Klaas Smits and Alan D. Grossman, "The Transcriptional Regulator Rok Binds A+T-Rich DNA and Is Involved in Repression of a Mobile Genetic Element in *Bacillus subtilis*," PLoS Genetics (2010) 6(11): e1001207; Catherine A. Lee, et al., "Identification and Characterization of int (integrase), xis (excisionase) and Chromosomal Attachment Sites of the Integrative and Conjugative Element ICEBs1 of *Bacillus subtilis*," Molecular Microbiology (2007) 66(6): 1356-1369). Concentrated circular plasmid DNA containing either i) the swrA gene under a constitutive promoter for the pPen_swrA construct or ii) the swrA gene under its own promoter for the endoPro_swrA construct was transformed into the donor strain, *Bacillus subtilis* MMB869 bp natural competence. MMB869 contains an Integrative and Conjugative Element for *B. subtilis* (ICE Bs1) transposon (see Smits and Grossman, above) which facilitates the movement of DNA cloned in the plasmid vector into *Bacillus* species. This occurs by natural competence with the desired DNA construct inserted between two domains which are homologous to locations in the *Bacillus* genome.

To allow natural competence to occur, MMB869 cells were grown in SPC media (SPC media: 10 ml 10× Spizizen, 1 ml 50% glucose, 4 ml 5% yeast extract, 2.5 ml 1% casamino acids, 1.6 ml 2.5 mg/ml tryptophan, 0.5 ml 1 M MgSO$_4$; 10× Spizizen Salts: 2% (NH$_4$)2SO$_4$, 14% anhydrous K$_2$HPO$_4$, 6% K$_2$HPO$_4$, 1% trisodium citrate.2H$_2$O, 0.2% Mg$_2$SO$_4$.7H$_2$O), transferred to SPII media (10 ml 10× Spizezen, 1 ml 50% glucose, 2 ml 5% yeast extract, 1 ml 1% casamino acids, 1.6 ml 2.5 mg/ml tryptophan, 1 ml 50 mM CaCl$_2$, 0.5 ml 1 M MgSO$_4$), pelleted, and resuspended in SPII media. The MMB869 cells were then added to a small volume of ME solution (0.200 ml 10× Spizizen Salts, 0.020 ml 200 mM EGTA, 1.780 ml sterile, deionized water) containing the purified plasmid DNA. The cell and DNA mixture incubated at 37° C. for 1 hour with shaking.

Cells were plated on LB-Kanamycin agar plates and grown overnight at 37° C. Several colonies from the LB-Kanamycin plates were patched onto LB-Chloramphenicol plates to confirm that the plasmid had been inserted via a double crossover event. Newly transformed donor MMB869 strains were used to transfer the pPen_swrA and endoPro_swrA constructs, respectively, into the AQ30002 swrA− strain by conjugation. MMB869 donor strains containing pPen_swrA and endoPro_swrA ICE constructs were grown on LB-Kanamycin plates overnight. AQ30002_strepR (AQ30002 containing a streptomycin resistance gene) was grown on LB-Agar overnight. Single colonies of the pPen_swrA and endoPro_swrA MMB869 strains were transferred into LB+Kanamycin. A single colony of AQ30002_strepR was also transferred into LB+Streptomycin. These three cultures were grown to an OD600 of ~1.0, diluted to OD600 of 0.02 in fresh LB, grown for ~1 hour at 37° C., and xylose was added to induce the ICE construct excision and transfer to AQ30002_strepR via conjugation.

Cells were grown for an additional 1 hour at 37° C., at which time the OD600 for these cultures was approximately 0.9. 2.5 ml of the donor cells were combined with 2.5 ml of AQ30002_strepR cells and vacuum-filtered onto a sterile membrane filter. The filter was removed from the filter assembly, transferred using sterile techniques onto SMS-Agar plates (25 mls of 10× Spizizen Salts and 3.75 g agar in a total of 250 ml deionized water) and incubated overnight at 30° C. The cells were recovered by washing them off the filter plate with 5 mls of 1× Spizizen salts (1:10 dilution of 10× Spizizen Salts in sterile, deionized water). 100 μl of cells were plated onto LB-kanamycin/streptomycin plates and incubated overnight at 37° C. to identify AQ30002_strepR transconjugates. The remaining cell solution was pelleted by centrifugation, resuspended in LB, and plated onto LB-kanamycin/streptomycin.

We hypothesized that the complementation of AQ30002 with either the pPen_swrA construct or the endoPro_swrA construct would result in the loss of the sandpaper phenotype and reversion back to a mucoidal wild-type QST713 swrA+ phenotype. In addition to colony morphology, we confirmed complementation by assessing whether or not the addition of the swrA gene rescued the ability of AQ30002 to swarm in a swarming assay as described in Joyce E. Patrick and Daniel B. Kearns, "Laboratory Strains of *Bacillus subtilis* Do Not Exhibit Swarming Motility," Journal of Bacteriology (2009) 191(22): 7129-7133). See FIG. 7.

We also measured root colonization with AQ30002 cells containing either the pPen_swrA construct or the endoPro_swrA construct. Tomato seeds were surface-sterilized first with 70% ethanol and then with 10% bleach. The seeds were then rinsed with sterile deionized water and placed in separate wells of 48-well plates containing a small volume of sterile water. The seeds were left to germinate under light (high-intensity, set to an 8 hr light schedule) at room temperature and were used 5-7 days later.

The roots of these germinated seeds were dipped in a cell suspension in Phosphate Buffered Saline (PBS) solution. To normalize the concentration of the cell suspensions, an OD600 nm of 0.01 was used as this is the approximate OD600 nm of QST713 that yields 10E6 CFU/ml. After dipping, each germinated seed was then placed in a test tube containing 12 ml of sterile MS medium (2.215 g/L Murashige and Skoog (MS) salts, 1.5% Sucrose, 1% agar, pH 5.7) and allowed to grow for about 1 week under light at room temperature. Root colonization (biofilm formation on the root) was visually observed with a Keyence digital microscope and was rated from zero (indicating no root colonization) to three (indicating aggressive root colonization). In each experiment, a root dipped in sterile water served as the negative control.

Results

Insertion of the pPen_swrA gene ICE construct into AQ30002_strepR (designated AQ30002_pPen_swrA_ICE cells) created bacterial cells with partial mucoidal morphology at a very low frequency. Individual transconjugates were collected and re-streaked onto individual LB-Kanamycin/Streptomycin plates for confirmation and future experiments.

Figure 7:
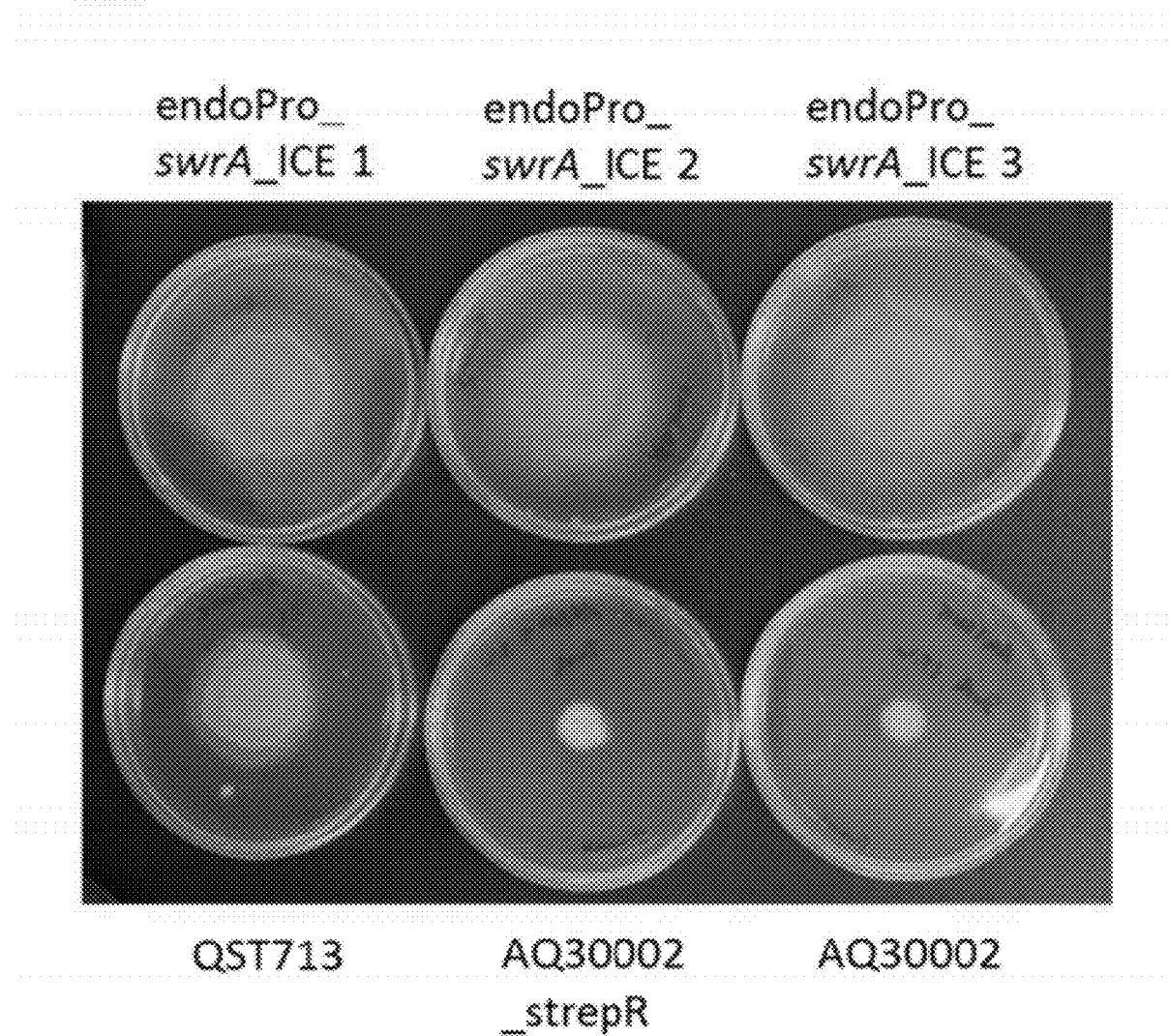
FIG. 7 shows images of 0.7% LB-agar swarming assay plates of QST713 swrA⁺ ("QST713"), AQ30002 swrA⁻ ("AQ30002") and various constructs based on these strains.

QST713 and quite different from AQ30002 cells. AQ30002_endoPro_swrA⁻_ICE cells are swarming positive unlike the AQ30002 strain (FIG. 7). AQ30002_endoPro_swrA⁻_ICE cells swarm at a rate similar to QST713 in a quantitative swarming assay (data not shown). AQ30015_endoPro_swrA⁻_ICE cells behaved similarly in all assays (data not shown).

Figure 8:
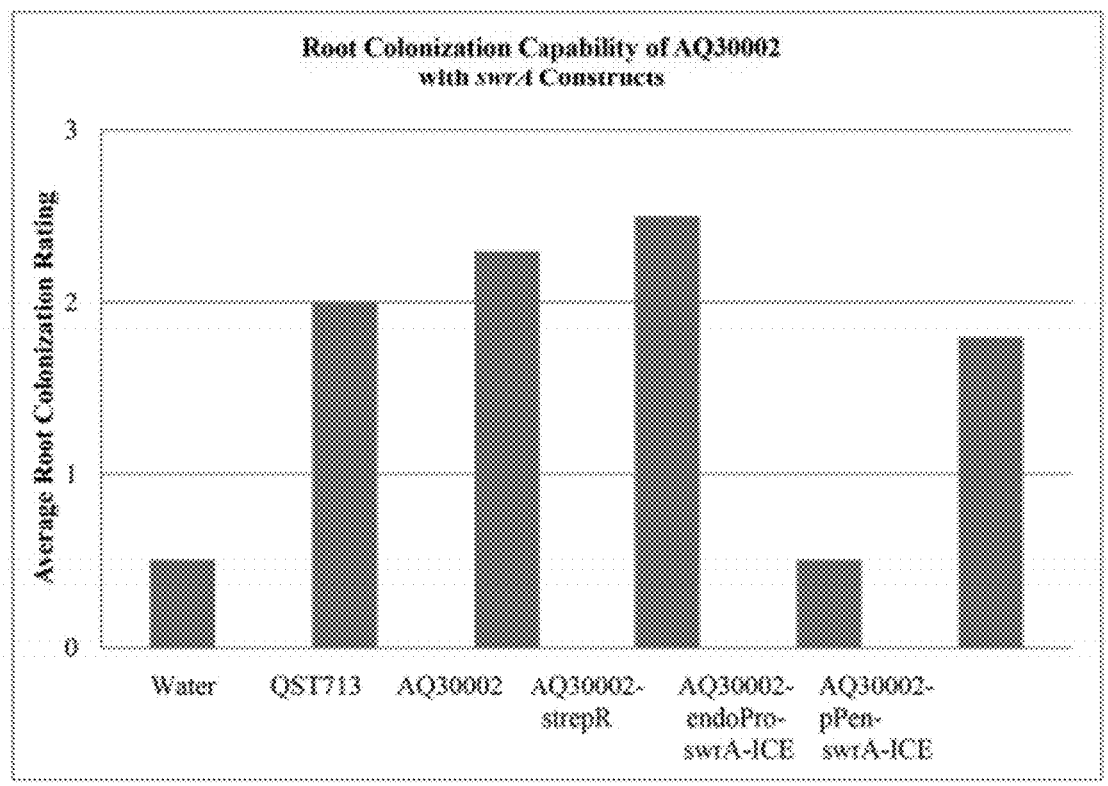
FIG. 8 shows average root colonization ratings for QST713 swrA⁺ ("QST713"), AQ30002 swrA⁻ ("AQ30002") and various constructs based on these strains and demonstrates that complementation with wild-type swrA in AQ30002 swrA⁻ cells reduces root colonization capability.
Figure 9:
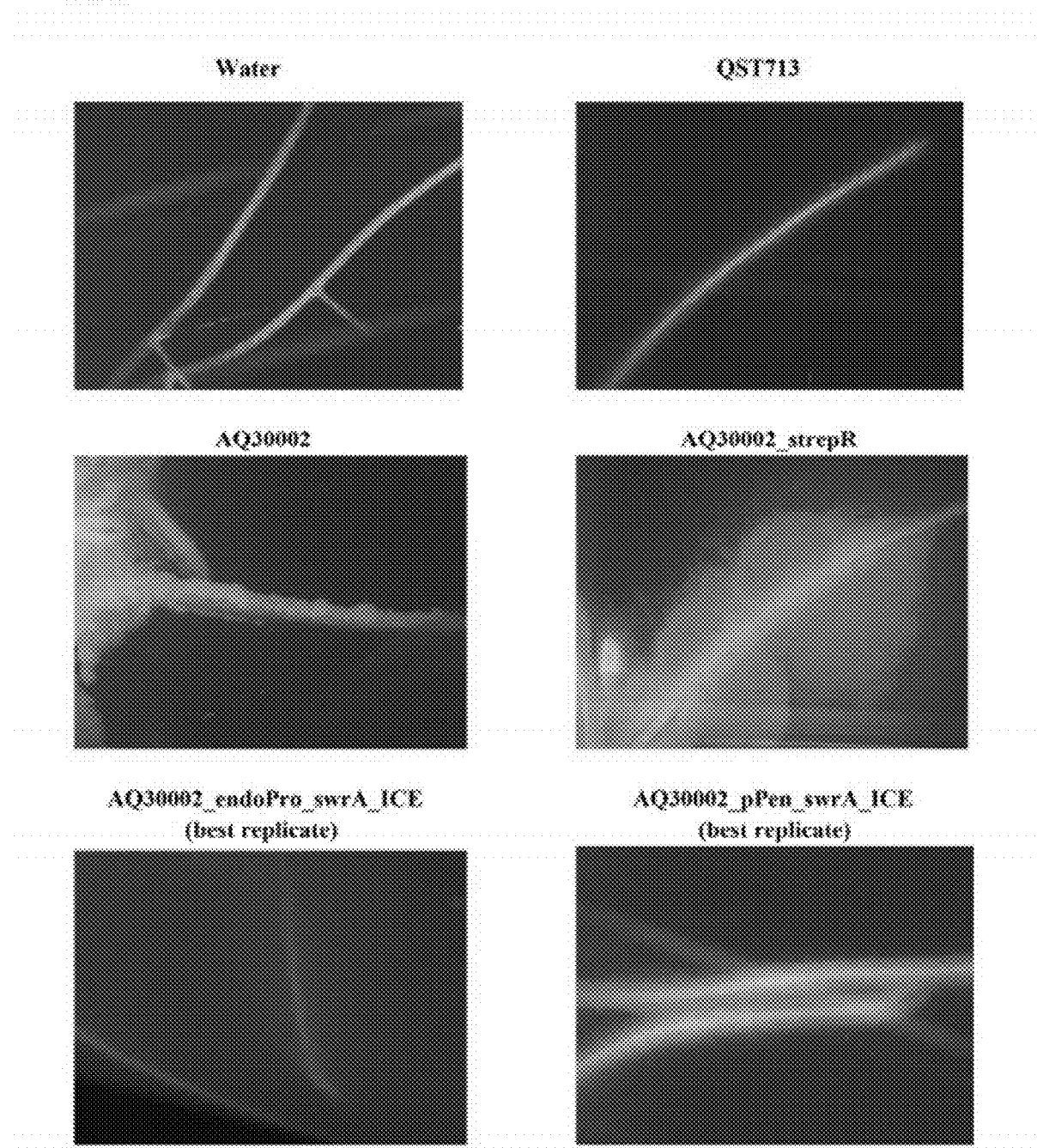
FIG. 9 shows root biofilm images captured with digital light microscopy showing the similarity of biofilms between AQ30002_endoPro_swrA_ICE (complemented strain) and QST713 swrA⁺ ("QST713") and the similarity between AQ30002_pPen_swrA_ICE (partial complementation) and AQ30002 swrA⁻ ("AQ30002").

The results in the root colonization assay agreed with those in the cell chaining/clumping and swarming assays. In the root colonization assay, the AQ30002_endoPro_swrA⁻_ICE cells did not colonize the tomato roots as well as the AQ30002 or AQ30002_strepR treatments (see Table 3 and FIG. 8). In addition, when looking at the biofilm of the best colonized root sample from each set of replicates, the biofilm of the AQ30002_pPen_swrA_ICE treatment seemed to match the biofilm of AQ30002 and AQ30002_strepR more closely than the AQ30002_endoPro_swrA⁻_ICE treatment, which seemed to resemble the QST713 biofilm (as shown in FIG. 9).

TABLE 3

Results of root colonization assay with four replicates for each treatment.

| Plant Root Treatment | Replicate #1 | Replicate #2 | Replicate #3 | Replicate #4 | Average |
|---|---|---|---|---|---|
| Water | 0 | 2 | 0 | 0 | 0.5 |
| QST713 | 2 | 2 | 2 | 2 | 2.0 |
| AQ30002 | 2 | 2 | no root | 3 | 2.3 |
| AQ30002_strepR | 3 | no root | no root | 2 | 2.5 |
| AQ30002_endoPro_swrA_ICE | 2 | 0 | 0 | 0 | 0.5 |
| AQ30002_pPen_swrA_ICE | 3 | 0 | 2 | 2 | 1.8 |

The majority of the transconjugants retained a sandpaper-like morphology or appeared to be a mixture of sandpaper and mucoidal. The endoPro_swrA ICE construct insertion into AQ30002_strepR (designated AQ30002_endoPro_swrA⁻_ICE cells) created bacterial cells with 100% mucoidal morphology. No sandpaper-like colonies were observed. Individual isolates were collected and re-streaked onto individual LB-Kanamycin/Streptomycin plates for confirmation and future experiments. These results were identical for ICE insertion into AQ30015_strepR, a second streptomycin-resistant strain independently derived from QST 713 with the same genetic mutation in swrA as AQ30002 (data not shown).

In order to confirm that AQ30002_strepR and AQ30015_strepR retained the original swrA mutation and that the pPen_swrA⁻_ICE and endoPro_swrA_ICE constructs contained wild type versions of swrA, genomic DNA was purified from two separate isolates of each transconjugation experiment, and PCR amplification of the endogenous swrA locus and the swrA_ICE constructs was performed. Sequencing of these PCR products confirmed that the endogenous swrA locus was mutant and the swrA_ICE constructs were wild type.

Further characterization of the AQ30002_endoPro_swrA⁻_ICE cells included growth in liquid culture to compare the extent of chaining/clumping versus AQ30002 as well as comparing the swarming ability of these strains to AQ30002 using a qualitative assay and a quantitative assay. AQ30002_endoPro_swrA⁻_ICE cells appear cloudy and translucent compared to the highly chained/clumpy nature of AQ30002 when grown in a 14 ml snap cap tube in LB liquid media overnight at 30° C. with 250 rpm shaking.

To test swarming a 0.7% LB-Agar plate was inoculated with an inoculation loop of overnight liquid culture, dried, and allowed to incubate for approximately 10 hours at 37° C. Following incubation, AQ30002_endoPro_swrA⁻_ICE cells swarmed across much of the plate similar to wild type Example 8

Pellicle Robustness of AQ30002 Liquid Cultures

Cultures of bacteria growing on the surface of liquid media may form a more or less continuous film called a pellicle. This film consists of microbial cells and a secreted extracellular matrix. Pellicles, therefore, represent liquid/air interface biofilms. As described further herein, pellicle robustness can be ascertained experimentally by poking the pellicles to see if they rupture.

Figure 10:
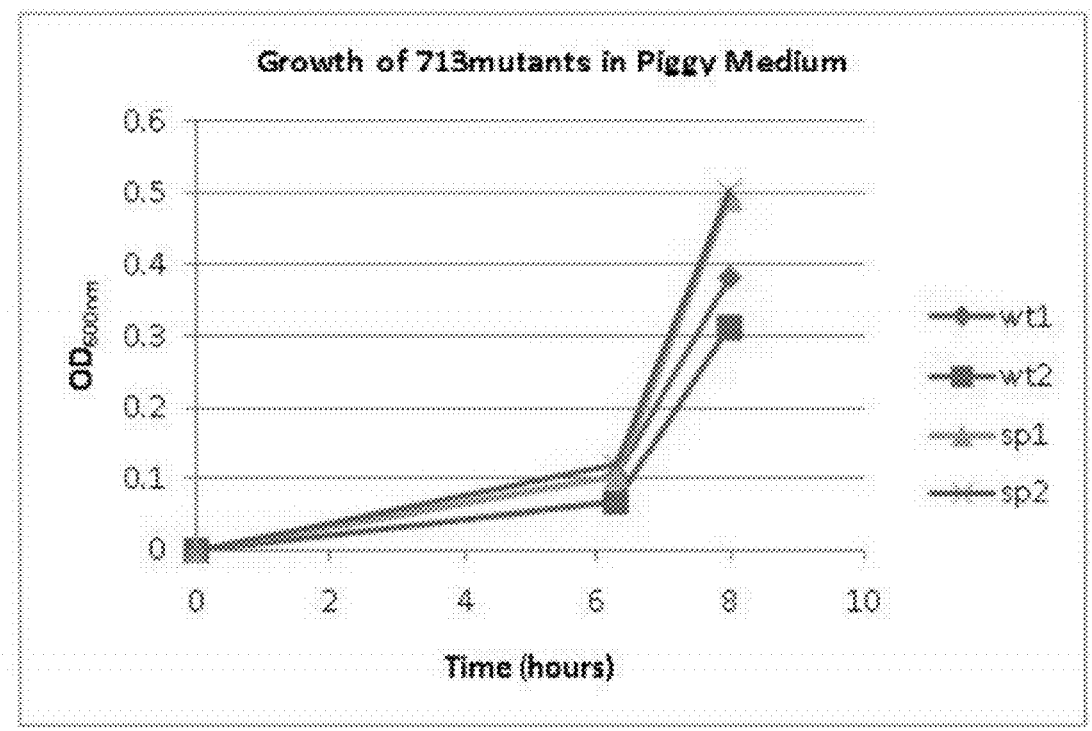
FIG. 10 represents results of growth of two replicates each of QST713 wild type swrA⁺ and AQ30002 swrA⁻ sandpaper types in pork-stock medium at 30° C.

Two replicate tubes, designated as wt1 and wt2, from a colony of B. subtilis strain QST713 wild type swrA⁺ (i.e., 100% swrA⁺ cells, grown from a single colony) and two replicates, designated as sp1 and sp2, from a colony of B. subtilis strain AQ30002 swrA⁻ were grown to mid-log phase in Pork-Stock Medium or Piggy Medium (10 g/L glucose, 8 g/L yeast extract, 8 g/L Pork Stock, pH 8.5). QST713 wild type swrA⁺ and AQ30002 swrA⁻ had similar growth rates in Pork-Stock Medium (see growth curves in FIG. 10).

QST713 wild type swrA⁺ and AQ30002 swrA⁻ also had similar susceptibility to antibiotics, similar growth patterns at temperatures ranging from 15° C. to 65° C., similar growth on blood agar, and similar metabolic profiles as determined with the BioLog Phenotype Microarray technology (Hayward, Calif.) (data not provided).

The two strains were grown in 20 ml of Pork-Stock Medium at 200 rpm at 30° C. Aliquots were diluted into Trypticase Soy Broth (TSB) Medium (17 g/L pancreatic digest of casein, 3 g/L papaic digest of soybean meal, 5 g/L sodium chloride, 2.5 g/L dipotassium phosphate, 2.5 g/L dextrose) in 24-well plates and allowed to grow at room temperature on the lab bench for 3 days.

Figure 11:
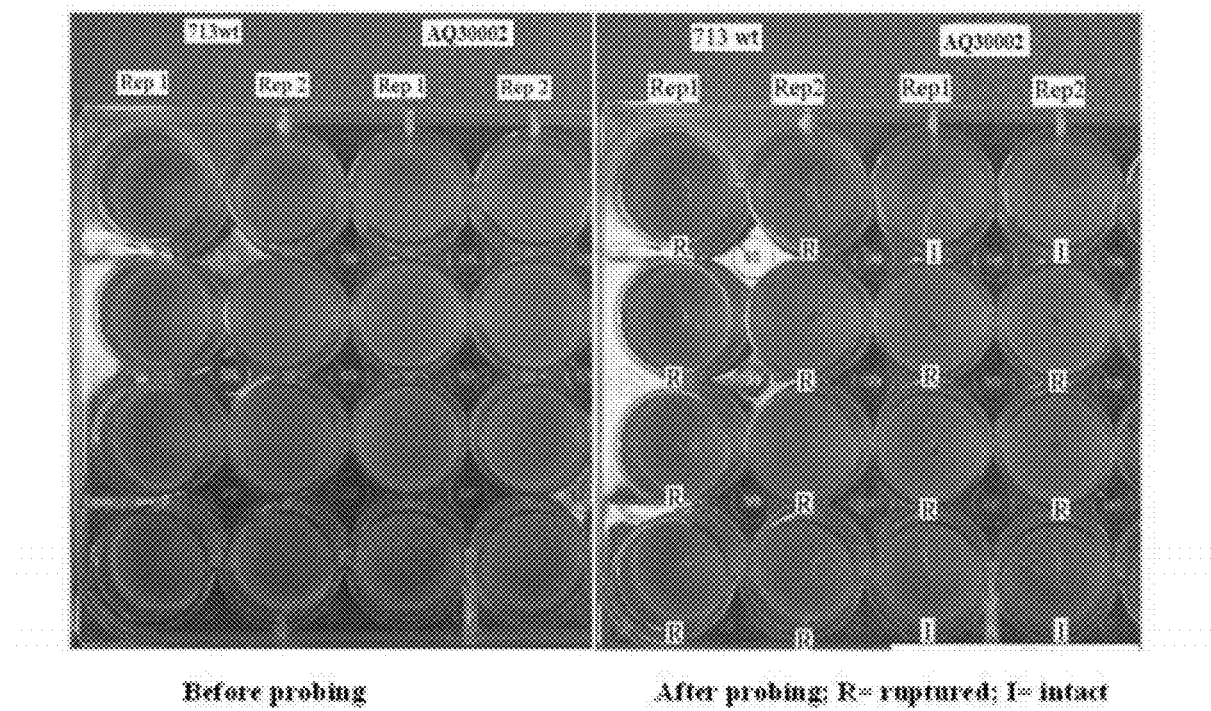
FIG. 11 represents results of pellicle robustness assay of two replicates each of QST713 wild type swrA⁺ ("713 wt") and AQ30002 swrA⁻ ("AQ30002") cultures.

Both samples of each strain had 4 replicate wells so that each strain had a total of 8 pellicles to examine. Each pellicle was poked three times until the pipette tip hit the bottom of the plate lightly. The number of pellicles that remained intact after poking was compared to those that were ruptured. Both strains formed pellicles after 3 days growth in TSB Medium. While all 8 pellicles formed by QST713 wild type swrA+ ruptured after poking only 4 of the 8 pellicles formed by AQ30002 swrA− ruptured (see FIG. 11).

Example 9

Characterization of AQ30002 Biofilm after Root Colonization

Tomato seeds were surface-sterilized with 70% Ethanol and 10% bleach and were then rinsed with sterile deionized water.

For sterile germination, seeds were placed between two sheets of sterile filter paper and sterile deionized water was added. Plates were sealed with Parafilm and placed under light (on a 12 hr dark/light schedule) for 7 days at room temperature after which germinated seeds were present.

The roots of these germinated seeds were dipped in a suspension of AQ30002 swrA− or QST713 wild type swrA+ cells in Phosphate Buffered Saline (PBS) solution. To normalize the concentration of the cell suspensions, an $OD_{600\,nm}$ of 0.01 was used as this is the approximate $OD_{600\,nm}$ of QST713 that yields 10E6 CFU/ml.

In order to allow for sterile growth and root colonization, after dipping, each germinated seed was then placed in a test tube containing 12 ml of sterile MS medium (2.215 g/L Murashige and Skoog (MS) salts, 1.5% Sucrose, 1% agar, pH 5.7) and allowed to grow for 10 days under light at room temperature. Root colonization was visually observed with a Keyence digital microscope.

The water control had no colonization. QST713 wild type swrA+ colonized the whole root including the tip, and the biofilm was very cloudy. AQ30002 swrA− also colonized the whole root including the tip, and the biofilm appeared more compact and seemed to bind more closely to the root than QST713 wild type swrA+ (see FIG. 12).

To verify the dense, compact nature of the AQ30002 swrA− biofilm on the root surface as compared to the QST713 wild type swrA+ biofilm additional samples were prepared as described above. After 1 week of growth under light at room temperature roots coated with either QST713 wild type swrA+ or AQ30002 swrA− cells were dehydrated in ethanol, dried, coated with gold, and visualized with a Scanning Electron Microscope (SEM). The AQ30002 swrA− biofilm on the root surface again appeared significantly more compact than that formed by QST713 wild type swrA+ (see FIG. 13). Note that this method underestimates the diffuse nature of the wild type biofilm since this structure would have had significantly more shrinkage and collapse during the ethanol dehydration.

To further characterize the AQ30002 swrA− biofilm on the root surface as compared to the QST713 wild type swrA+ biofilm additional root samples were inoculated and grown as described above and analyzed by light microscopy, as follows. Roots were gently removed from agar, fixed for 15 minutes in Karnovsky's fixative and dehydrated in increasing levels of ethanol up to 100%. They were then critical point dried, treated with osmium tetroxide and embedded in resin. Some resin blocks were thick-sectioned, dyed with methyl blue, mounted and visualized with a microscope at 10-40× magnification. The water control had no colonization of the roots. QST713 wild type swrA+ cells surrounded the root in thin, sparse, diffuse layers. The lack of evident biofilm is likely an artifact of the weak, diffuse nature of the wild type biofilm and its loss upon removal from the agar or during the washing and dehydration steps. In contrast, AQ30002 cells surrounded the root in thick, dense film. See FIG. 14. The adherence of the mutant biofilm to the root surface under the same preparative conditions demonstrates that it is physically much tougher and more adherent than the wildtype structure.

In parallel, other fixed and embedded root samples were thin-sectioned, mounted and visualized with a transmission electron microscope. While the water control showed no colonization, the QST713 wild type swrA+ cells looked like textbook *Bacillus* vegetative cells. The AQ30002 cells showed a completely different morphology. The diameter of the AQ30002 cells were significantly bigger (0.83 µm+/−0.066; p<0.05; n=14; Fisher test) than the diameter of the QST713 cells (0.52 µm+/−0.027; n=11). In addition, the AQ30002 cells showed a much more complex morphology with a large electron transparent (white) region in the center of the cells and what appeared to be an additional coat or cell wall. See FIG. 14.

Example 10

Activity of AQ30002 in Tomato, Corn, and Wheat Plant Growth Promotion

Whole broth from each of *Bacillus subtilis* QST713 (i.e., a mixture of wild type and sandpaper cells as found in SERENADE®, see FIG. 4), AQ30002 (swrA−), an independent genetic variant of QST713 (713var) and *Bacillus pumilus* QST2808 (synonymous with AQ2808) was prepared as a seed drench. Seed flasks containing Luria Broth (LB) were inoculated with each strain, and these flasks were grown overnight at 30° C. The next day, aliquots from each seed flask were inoculated into a soy-based medium and grown until sporulation.

Prior to seed drench the final concentrations of the whole broths were diluted to a 64 oz/acre rate of the commercial SERENADE® product based on CFU/ml. 64 oz/acre refers to the number of colony forming unit per seed, or $2.2 \times 10^8$ CFU/plant. The amounts used herein were calculated based on the cfus/ml of the whole broths.

Plug trays (Hummert, catalog number 14-3128) were filled with seed germination mix, and each cell was seeded with one seed. 'Spring Treat Hybrid' corn seeds, 'Derkwin' wheat seeds, and 'QualiT 21' tomato seeds were used. Thus, the tests included both monocotyledonous species (i.e., corn and wheat) and dicotyledonous species (i.e., tomato). Each plug tray was then treated with 2 ml of whole broth sample with the untreated controls receiving 2 ml of water. These trays were placed under high-intensity lights (~300 Einsteins, set to a 16-hour light/8-hour dark schedule) at room temperature. Watering was done as needed. No fertilizer was used.

Figure 15:
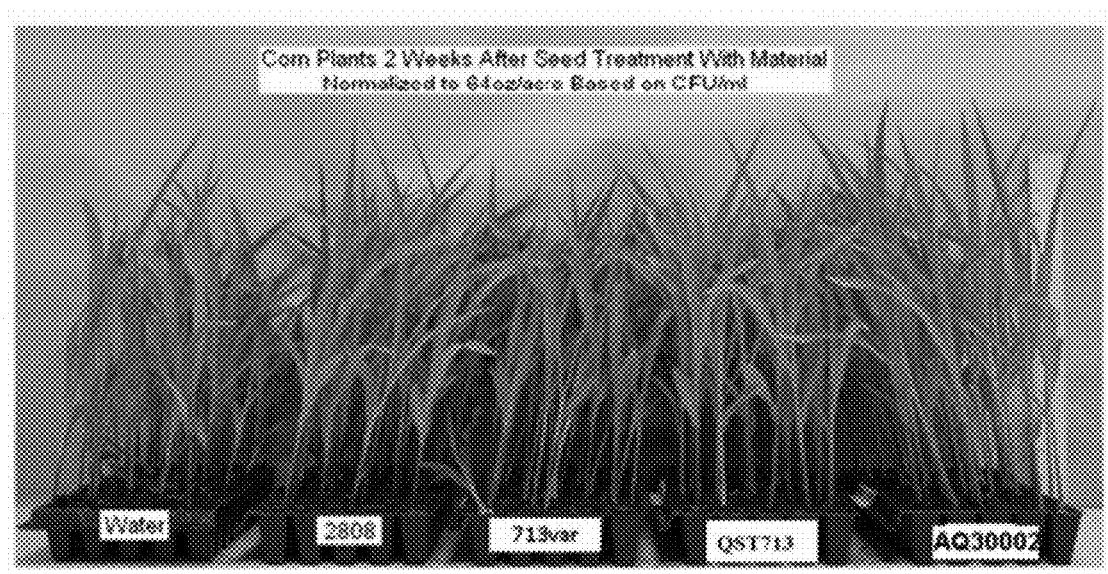
FIG. 15 represents results of a greenhouse study to measure plant growth promotion in corn treated with either AQ30002 swrA− ("AQ30002"), QST713 ("QST713", which is a mixture of wild type swrA+ and sandpaper swrA− cells in ratios as found in the SERENADE® product, see, e.g., Example 3 and FIG. 4) or other *Bacillus* strains. Shown are corn plants 2 weeks after seed treatment with application rates normalized to 64 oz/acre with equivalent CFU rates used for experimental products.
Figure 16:
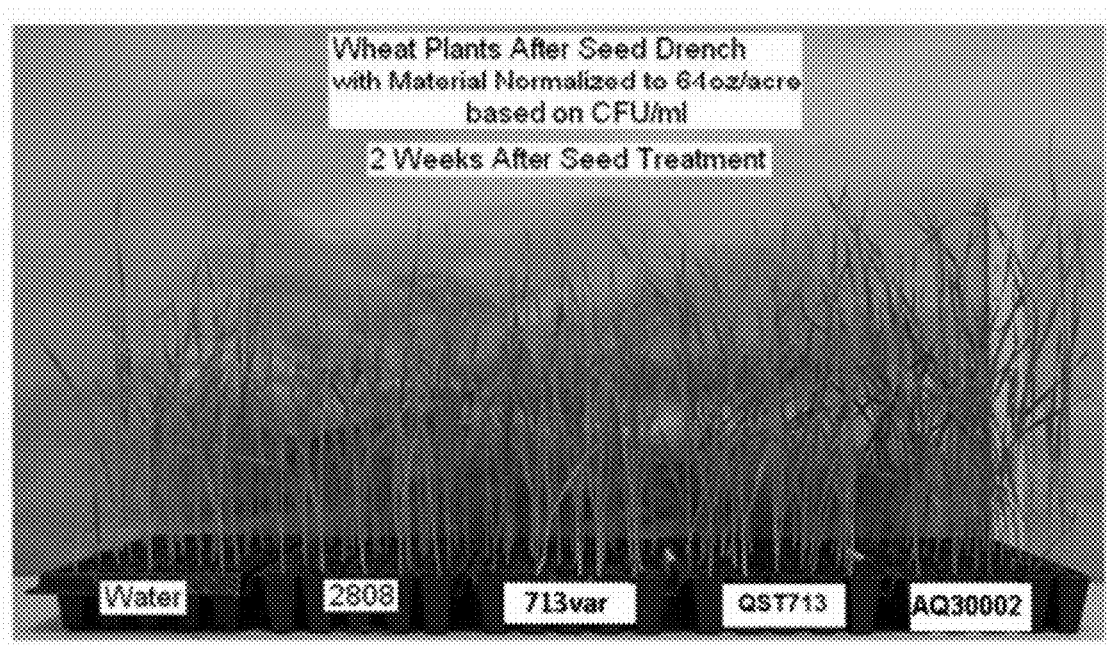
FIG. 16 represents results of greenhouse study to measure plant growth promotion in wheat treated with either AQ30002 swrA− ("AQ30002"), QST713 ("QST713", which is a mixture of wild type swrA+ and sandpaper swrA− cells in ratios as found in the SERENADE® product, see, e.g., Example 3 and FIG. 4) or other *Bacillus* strains. Shown are wheat plants 2 weeks after seed treatment which consisted of a seed drench with application rates normalized to 64 oz/acre with equivalent CFU rates used for experimental products.
Figure 17:
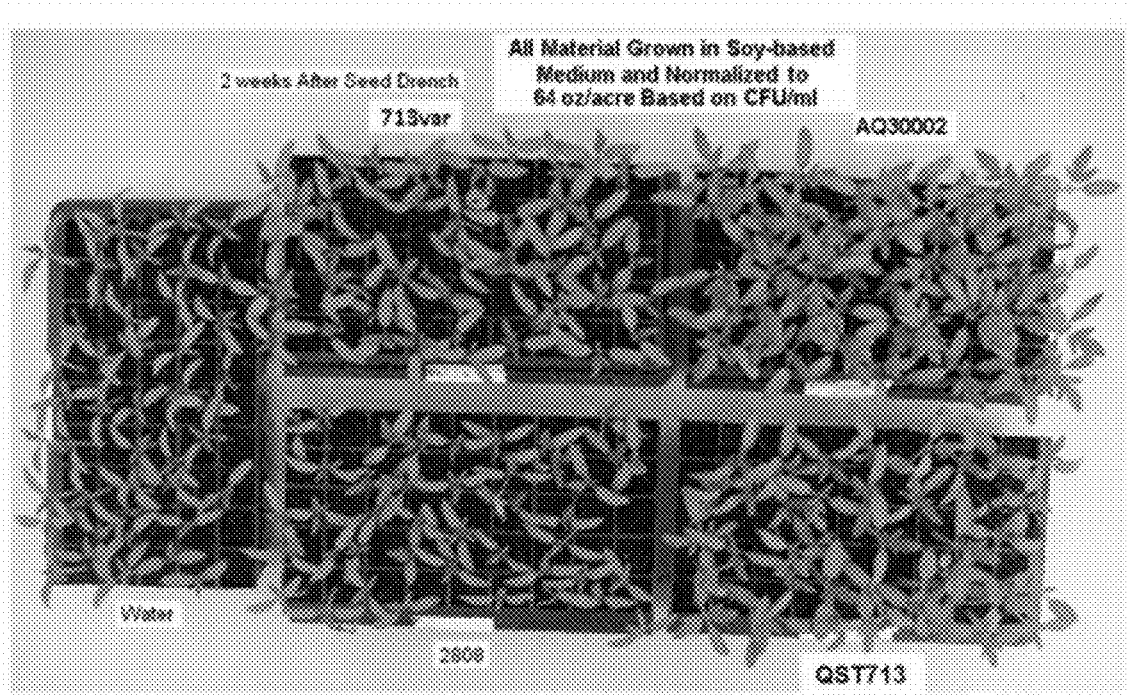
FIG. 17 represents results of greenhouse study to measure plant growth promotion in tomatoes treated with either AQ30002 swrA− ("AQ30002"), QST713 ("QST713", which is a mixture of wild type swrA+ and sandpaper swrA− cells in ratios as found in the SERENADE® product, see, e.g., Example 3 and FIG. 4) or other *Bacillus* strains produced using a soy-based medium. Shown are tomato plants 2 weeks after seed treatment which consisted of a seed drench with application rates normalized to 64 oz/acre with equivalent CFU rates used for experimental products.
Figure 18:
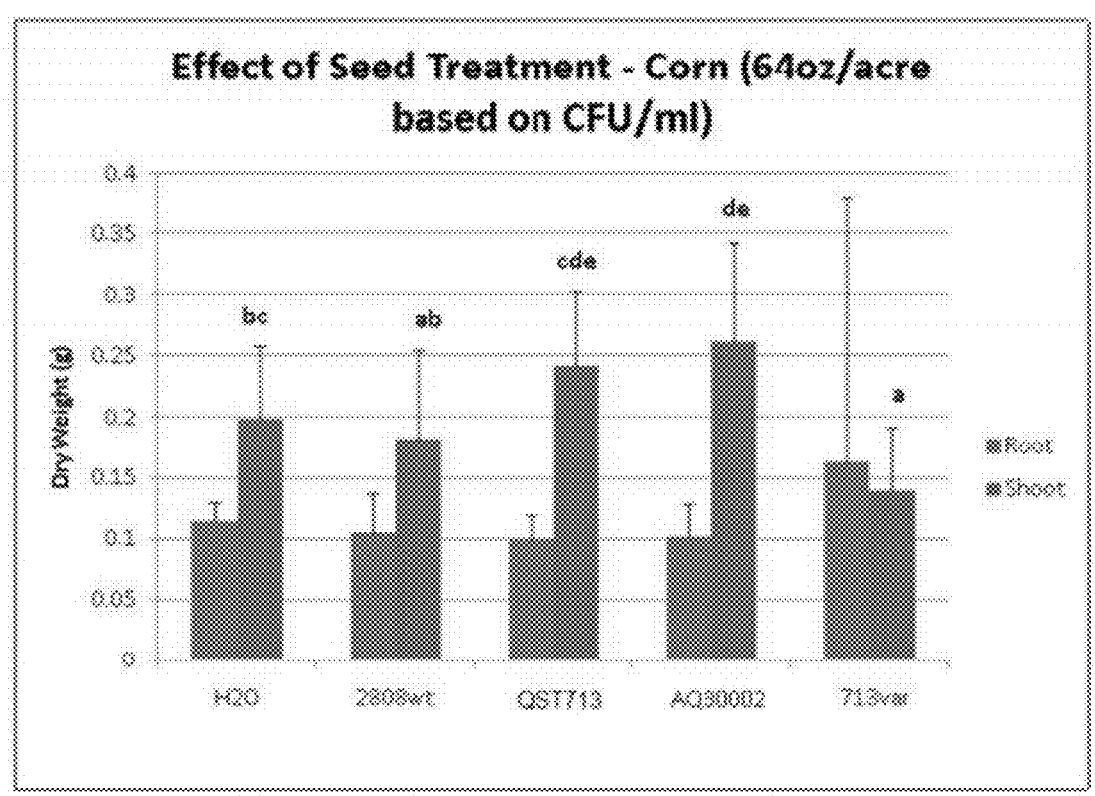
FIG. 18 represents results of a greenhouse study to measure dry weights of roots and shoots of corn treated with either AQ30002 ("AQ30002"), QST713 ("QST713", which is a mixture of wild type swrA+ and sandpaper swrA− cells in ratios as found in the SERENADE® product, see, e.g., Example 3 and FIG. 4) or other *Bacillus* strains produced using a soy-based medium.
Figure 19:
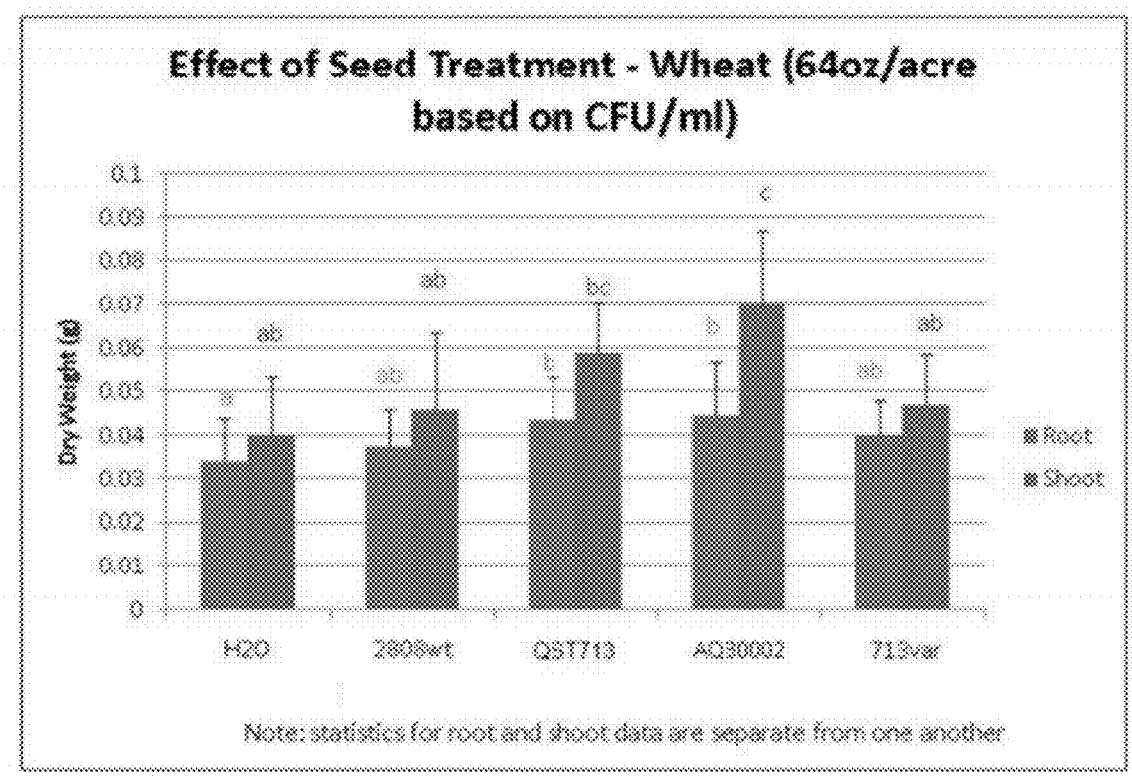
FIG. 19 represents results of a greenhouse study to measure dry weights of roots and shoots of wheat treated with either AQ30002 ("AQ30002"), QST713 ("QST713", which is a mixture of wild type swrA+ and sandpaper swrA− cells in ratios as found in the SERENADE® product, see, e.g., Example 3 and FIG. 4) or other *Bacillus* strains produced using a soy-based medium.
Figure 20:
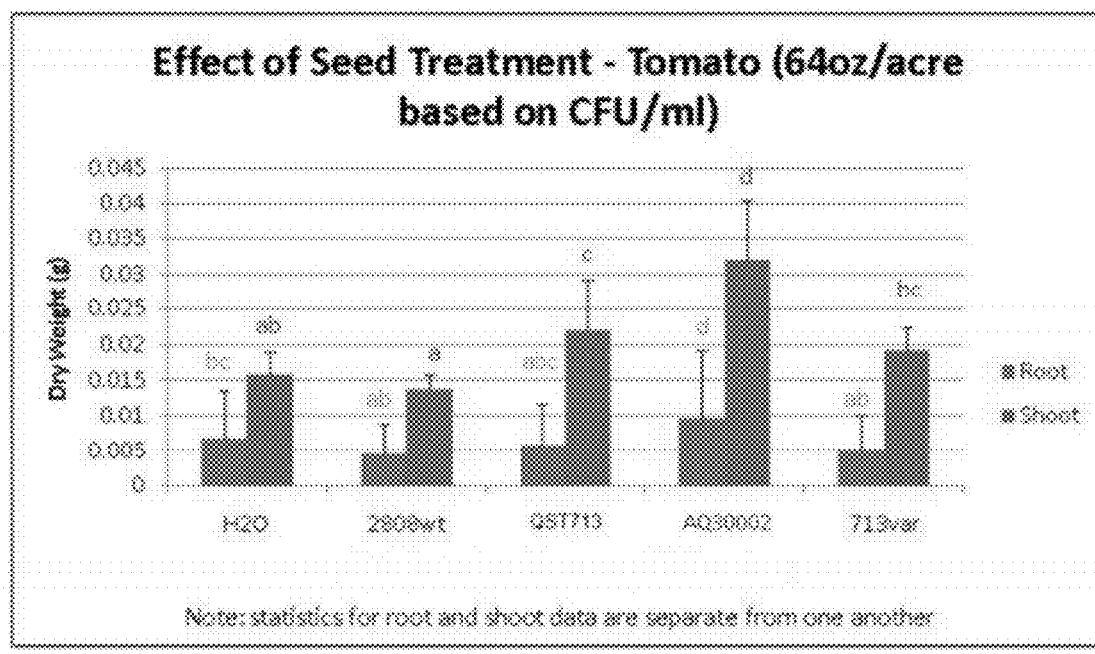
FIG. 20 represents results of a greenhouse study to measure dry weights of roots and shoots of tomato treated with either AQ30002 ("AQ30002"), QST713 ("QST713", which is a mixture of wild type swrA+ and sandpaper swrA− cells in ratios as found in the SERENADE® product, see, e.g., Example 3 and FIG. 4) or other *Bacillus* strains produced using a soy-based medium.

Tomato, corn and wheat plants were observed for plant growth promotion traits two weeks after drenching the seeds. Then the leaf and root tissues were harvested, dried in paper bags, and weighed. Plants treated with AQ30002 all appeared greener, taller and generally healthier than plants treated with water (see FIGS. 15, 16, and 17). The dry weights of all plant tissues treated with AQ30002 were significantly higher than those of corresponding tissues from untreated plants with the one exception of corn roots where dry weights were the same (see FIGS. 18, 19, and 20).

Example 11

Yield Enhancement of Processing Tomatoes Treated with AQ30002 in the Field

Two independent field trials were conducted near Escalon, Calif. and near San Luis Obispo, Calif. with processing tomato plants. The materials were applied to the plants as a drench at transplanting. *Bacillus subtilis* strains QST713 (i.e., a mixture of wild type and sandpaper-like cells as found in SERENADE®, see FIG. 4) and AQ30002 swrA⁻ were grown in a soy-based medium in bioreactors, formulated to mimic the commercial SERENADE® ASO product, and applied at concentrations equivalent to 3.4 qt/acre of commercial product. Plant growth stimulator (PGS) was applied at 625 ml/acre, and RIDOMIL GOLD® SL (Syngenta) containing the active ingredient mefenoxam was applied at a rate of 1 pint/acre. A Randomized Complete Block (RCB) Design was used with four replicates per treatment. Each replicate represented approximately 2 rows×25 feet.

Figure 21:
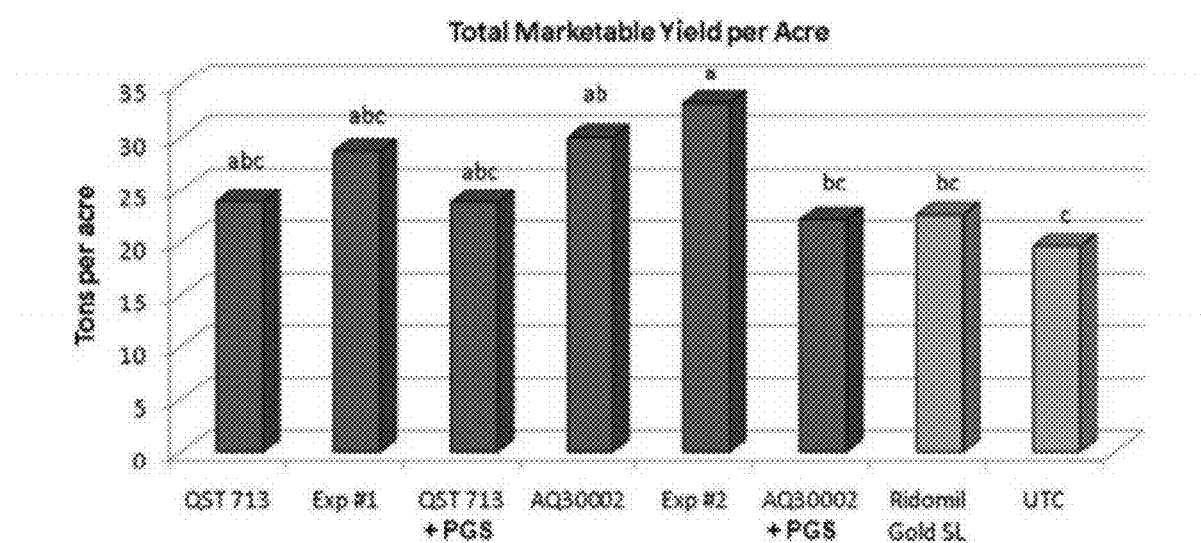
FIG. 21 represents results of a field study to measure yield of processing tomatoes from plants treated with *Bacillus subtilis* strains QST713 (a mixture of wild type swrA+ and sandpaper swrA− cells in ratios as found in the SERENADE® product, see, e.g., Example 3 and FIG. 4) ("QST713") or AQ30002 swrA− ("AQ30002") alone or in combination with plant growth stimulator (PGS). Strains were produced using a soy-based medium. Trials were conducted in Escalon, Calif. Treatments labeled "Exp" represent alternative experimental conditions. Measurements with the same letter are not statistically different at P=0.05 using analysis of variance (ANOVA).

In the trial conducted near Escalon the total marketable yield of plants treated with AQ30002 was significantly greater than that of the untreated control (UTC) (see FIG. 21).

While none of the treatments in the trial conducted near San Luis Obispo produced a greater total marketable yield than the untreated control (data not shown), this trial is not considered indicative of the typical yield enhancement possible with AQ30002 treatment of plants. Tomatoes are not generally grown in the San Luis Obispo area where the soil type and climate differ considerably from the California regions where tomatoes are more commonly cultivated. Also, the geographic displacement of the trial from traditional tomato growing areas and the inordinate time to harvest contributed to questionable results.

Example 12

Figure 22:
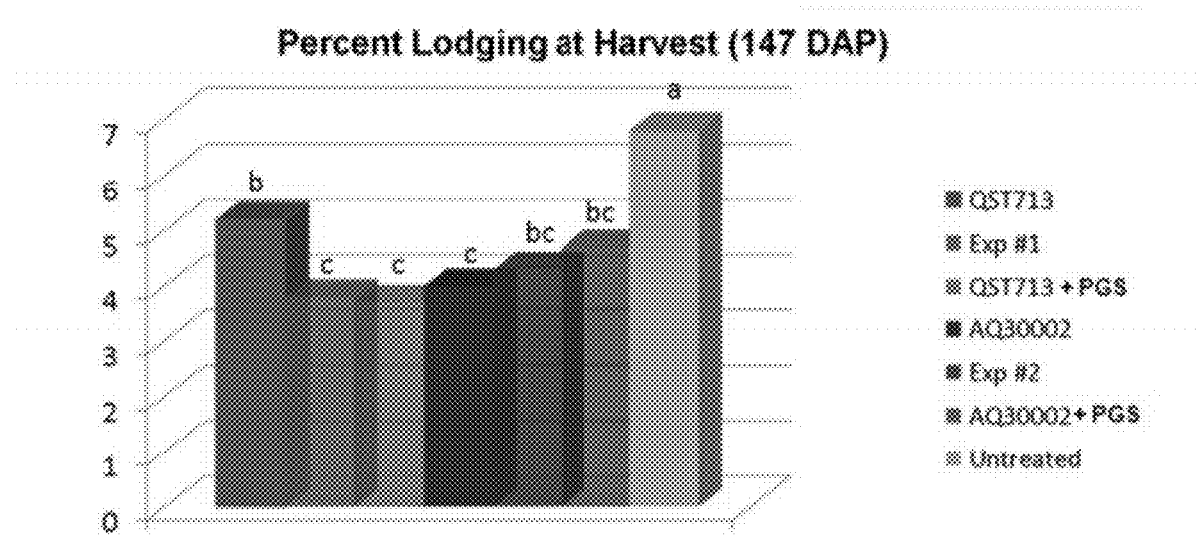
FIG. 22 represents percent lodging (breakage of the stalk below the ear) of a field study to measure corn plants treated with *Bacillus subtilis* strains QST713 (a mixture of wild type swrA+ and sandpaper swrA− cells in ratios as found in the SERENADE® product, see, e.g., Example 3 and FIG. 4) ("QST713") or AQ30002 swrA− ("AQ30002") alone or in combination with plant growth stimulator (PGS). Strains were produced using a soy-based medium. Trials were conducted in Paynesville, Minn. Treatments labeled "Exp" represent alternative experimental conditions. Measurements with the same letter are not statistically different at P=0.10 using analysis of variance (ANOVA).
Figure 25:
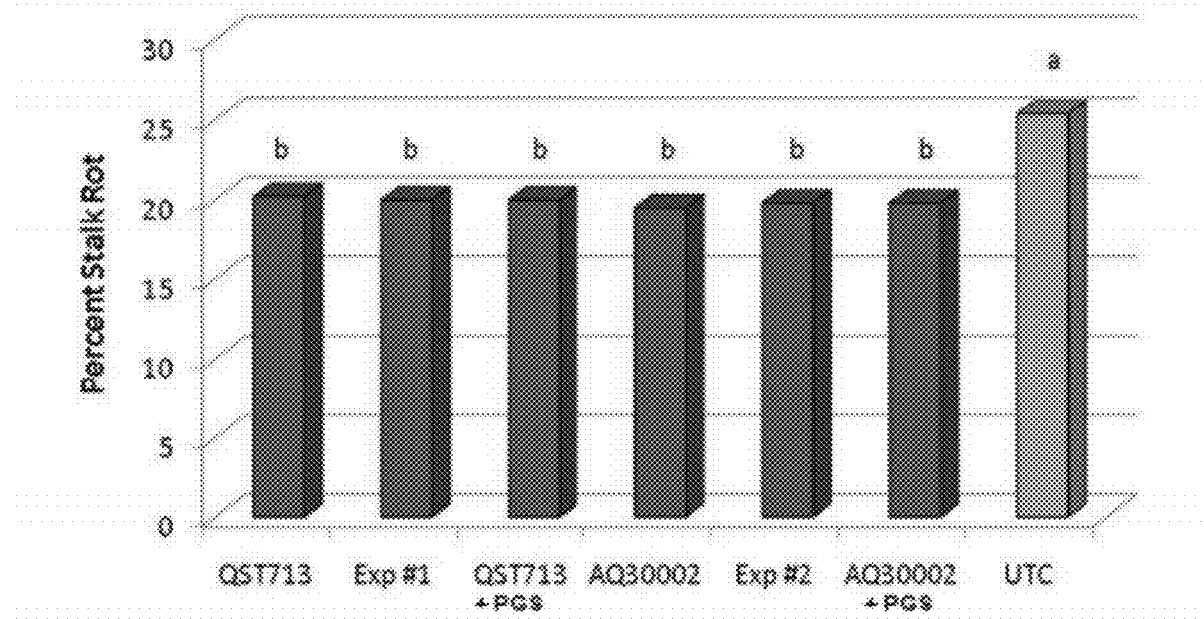
FIG. 25 represents results of field study to measure control of corn *Pythium* stalk rot by *Bacillus subtilis* strains QST713 (a mixture of wild type swrA+ and sandpaper swrA− cells in ratios as found in the SERENADE® product, see, e.g., Example 3 and FIG. 4) ("QST713") or AQ30002 swrA− ("AQ30002") alone or in combination with plant growth stimulator (PGS). Trials were conducted in Paynesville, Minn. Treatments labeled "Exp" represent alternative experimental conditions. Measurements with the same letter are not statistically different at P=0.05 using analysis of variance (ANOVA).

Decrease in Percent Lodging and Lower Incidence of Stalk Rot (*Pythium*) in Corn Plants Treated with AQ30002 in the Field A field trial was conducted near Paynesville, Minn. with *Zea mays indentata* (dent corn) variety Dekalb 'DK2C26' plants. The materials were applied to the plants as an in-furrow or T-band treatment diluted in water. No fertilizer or any other product was included in the tank mix besides the specified whole broth with or without a plant growth stimulator (PGS). *Bacillus subtilis* strains QST713 (i.e., a mixture of wild type and sandpaper-like cells as found in SERENADE®, see FIG. 4) and AQ30002 swrA⁻ were grown in a soy-based medium in a bioreactor, formulated to mimic the commercial SERENADE® ASO product, and applied at concentrations equivalent to 3.4 qt/acre of commercial product. Plant Growth Stimulator (PGS) was applied at 625 ml/acre. A Randomized Complete Block (RCB) Design was used with four replicates per treatment. Each replicate represented 4 rows×30 feet. None of the treated corn plants had significantly different yields than the untreated control (data not provided). However, corn plants treated with AQ30002 swrA⁻ had significantly less lodging than those treated with QST713 or than the untreated controls (see FIG. 22). In addition, all of the treatments including AQ30002 swrA⁻ significantly reduced the incidence of stalk rot caused by *Pythium* as compared to the untreated control (UTC) (see FIG. 25).

Figure 23:
FIG. 23 shows an image of soybean roots from plants treated with AQ30002 swrA− ("QRD154") and bacterial inoculant in furrow at planting.
Figure 24:
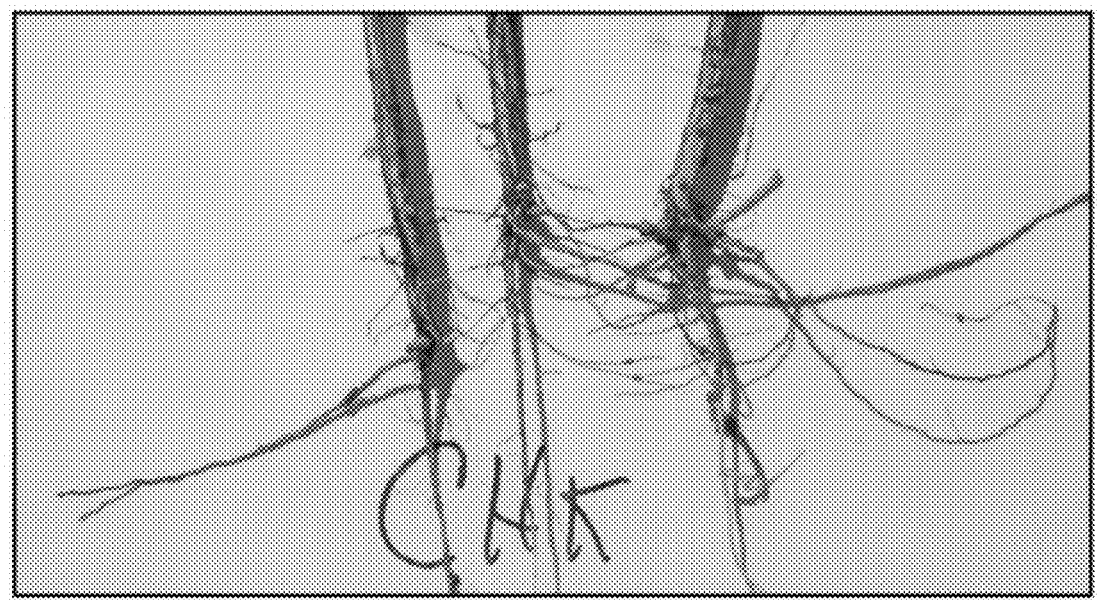
FIG. 24 shows an image of soybean roots from an untreated plant.

In another field trial, AQ30002 swrA⁻ grown in a soy-based medium in a bioreactor and formulated to mimic the commercial SERENADE® ASO product was applied in furrow at the time of planting soybeans at a rate of 2 quarts per acre along with a bacterial inoculant of nodule-forming bacteria, specifically, *Bradyrhizobium japonicum*. Plants, including roots, were harvested after four months and root nodulation for the untreated and treated samples compared. See results in FIGS. 23 and 24.

Example 13

Activity of AQ30002 Against Foliar Diseases

While not envisioned as a treatment for foliar diseases, AQ30002 swrA⁻ was observed to have activity against the following plant pathogens: *Xanthomonas campestris* pv. *campestris*, *Colletotrichum orbiculare* (cucumber anthracnose), *Botrytis cinerea* (botrytis blight of pepper), *Sphaerotheca fuliginea* (cucumber powdery mildew), *Pseudoperonospora cubensis* (cucumber downey mildew), *Puccinia recondita* (wheat leaf rust), *Pseudomonas syringae* pv. *tomato* (bacterial speck of tomato), and *Blumeria graminis* f. sp. *hordei* (barley powdery mildew) (data not provided).

Example 14

Activity of AQ30002 Against Soil Diseases

The QST713 (i.e., a mixture of wild type and sandpaper-like cells as found in SERENADE®, see FIG. 4) and AQ30002 swrA⁻ strains were grown in bioreactors in a soy-based medium and the whole broths were tested against *Pythium ultimum* and *Rhizoctonia solani* at 20% concentration. The plant pathogens were prepared in a "spawn bag" from Fungi Perfecti containing 200 g of vermiculite and 600 ml of potato dextrose (PD) broth. The bag was inoculated with a whole plate of about one week-old *Pythium ultimum* or *Rhizoctonia solani* and allowed to grow for one week before use.

The seed germination mix was moistened with 100 ml of deionized water per liter of mix and then infested at a rate of 8 g inoculum per liter mix for *Rhizoctonia solani* and 64 g/L mix for *Pythium ultimum*. The inoculated mix was then placed into 2.5 inch pots. Non-infested mix was also used as an uninfested control (UIC). After infestation and placing the mix into the pots, each pot in each treatment was drenched with 10 ml of its respective treatment. After drenching, each pot was planted with about 65 *Brassica* seedlings (variety: 'Johnny's Broccoli for Sprouting,' catalog number 2108) using a calibrated scoop). The pots were saturated with water, placed under high-intensity lights, and allowed to grow for one week before rating.

Figure 26:
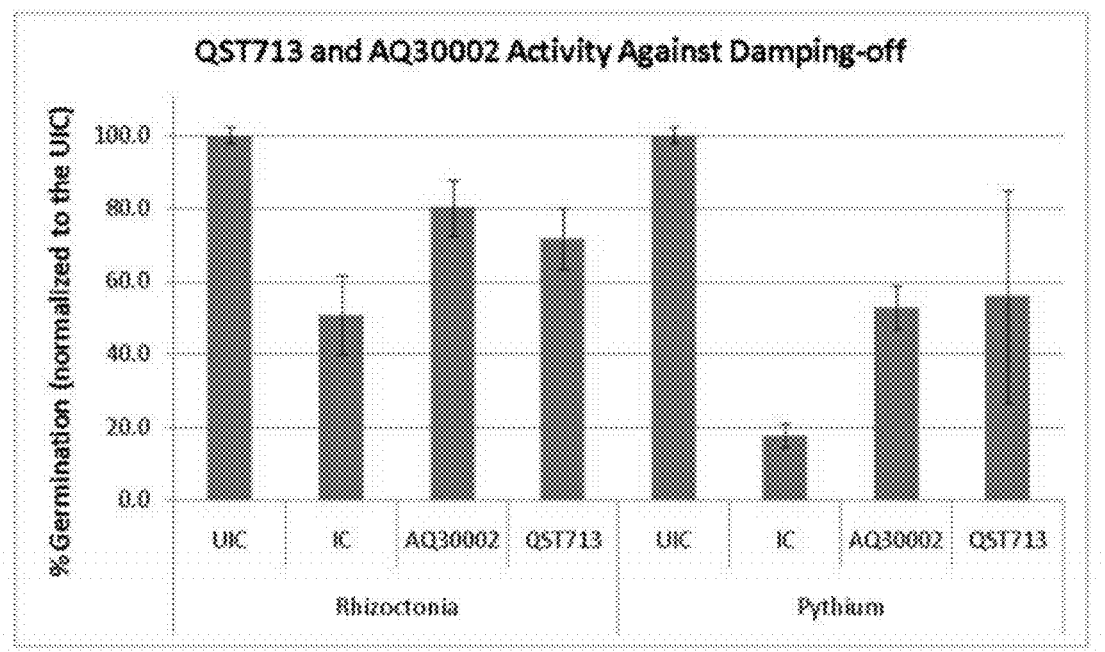
FIG. 26 represents results of a greenhouse study to compare the activity of QST713 (a mixture of wild type swrA+ and sandpaper swrA− cells in ratios as found in the SERENADE® product, see, e.g., Example 3 and FIG. 4) ("QST713") and AQ30002 swrA− ("AQ30002") against damping-off caused by *Pythium ultimum* and *Rhizoctonia solani*. Each bar represents the average of four measurements with the error bars indicating the standard deviations.

Individual seedlings in each replicate were counted for each treatment and each disease so that a quantitative number for seedling germination could be obtained. The results were compared with uninfested controls (UIC) and infested controls (IC) to determine activity (see FIG. 26). Disease control was determined by the number of seedlings that emerged and survived in the soil inoculated with the specific pathogen.

Field trials using AQ30002 and QST713 (i.e., a mixture of wild type and sandpaper-like cells at a ratio of roughly 200:1, as found in SERENADE®) prepared as described in Examples 11 and 12 were conducted to compare their efficacy against various soil plant pathogens. It appeared AQ30002 out-performed QST713, in terms of disease control, in trials for *Rhizoctonia* in peanuts and cauliflower and *Verticillium* wilt in lettuce. (Specific results not provided.) AQ30002 did not out-perform QST713 in all trials, in terms of disease control.

An in vitro experiment was conducted to test ability of AQ30002 to control another soil disease, *Sclerotium rolfsii*. Preliminary results showed that AQ30002 was more active than QST713 (i.e., a mixture of wild type and sandpaper-like cells as found in SERENADE®) against this disease. (Results not provided.)

Example 15

In Planta Activity of AQ30002 Against *Phytophthora capsici*

The QST713 (i.e., a mixture of wild type and sandpaper-like cells as found in SERENADE®, see FIG. 4) and AQ30002 swrA⁻ strains were grown in bioreactors in a soy-based medium and the whole broths were tested against *Phytophthora capsici* at 20% concentration. The *Phytophthora capsici* was grown on V-8 agar and allowed to release the zoospores in the sporangia into sterile deionized water. The zoospore concentration was then diluted to 2×10E4 zoospores/ml for inoculation (10 ml/plant).

Figure 27:
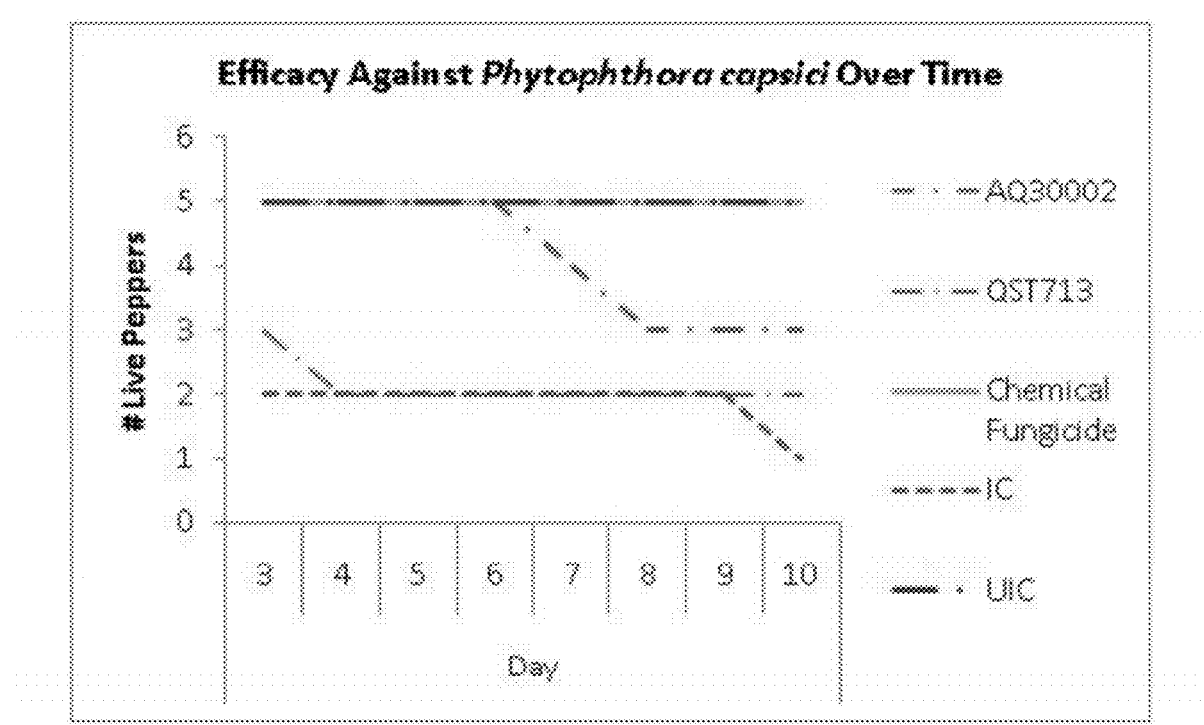
FIG. 27 provides a time course showing activity of QST713 (a mixture of wild type swrA+ and sandpaper swrA− cells in ratios as found in the SERENADE® product, see, e.g., Example 3 and FIG. 4) ("QST713") and AQ30002 swrA− ("AQ30002") against pepper wilt caused by *Phytophthora capsici* over an 8-day period in a greenhouse assay. Note that the uninfested control ("UIC") and chemical fungicide curves overlap.

Two-week-old peppers (variety 'California Wonder') planted in potting mix were each drenched with 10 ml of whole broth treatment, and inoculated with *Phytophthora capsici* the next day. To monitor the progression of the disease in the pepper plants and the protection afforded by treatment with QST713 or AQ30002 swrA⁻ the plants were monitored over an 8 day period. The chemical fungicide Aliette, which contains aluminum tris(O-ethyl phosphonate), was also tested at 3.2 mg/ml and at 1.6 mg/ml. Treatment with AQ30002 swrA⁻ protected plants for a longer duration with a greater number of total plants surviving than did treatment with QST713 (see FIG. 27).

Example 16

Increase in Chlorophyll Content of Plants Treated with AQ30002

Whole broth from each of *Bacillus subtilis* QST713 (i.e., a mixture of wild type and sand paper-like cells as found in SERENADE®, see FIG. 4) and AQ30002 swrA⁻ was prepared for use as a seed drench. The seed flask containing Luria Broth (LB) was inoculated and grown overnight at 30° C. The next day, 5 ml of the seed flask was inoculated into a soy-based medium. The flask grew until sporulation was complete. Prior to seed treatment the final concentrations of the whole broths were diluted to 4, 8, 16, 32, 64 and 128 oz/acre rate of the commercial SERENADE® product based on CFU/ml.

Plug trays (Hummert, catalog number 14-3128) were filled with seed germination mix, and each cell was seeded with one seed. QualiT 21' tomato seeds were used. Each plug tray was then treated with 2 ml of whole broth sample with the untreated controls receiving 2 ml of water. These trays were placed under high-intensity lights (~300 Einsteins, set to a 16-hour light/8-hour dark schedule) at room temperature. Watering was done as needed. No fertilizer was used.

Tomato plants were observed for plant growth promotion traits two weeks after drenching the seeds. Then the amount of chlorophyll in the leaves was quantified; 3 replicate hole punches were taken from 3 leaves at random in each treatment. The leaf disks were crushed and extracted with 80% Acetone$_{(aq)}$, and the OD$_{600\ nm}$ of the extracts was taken.

Both treatments, QST713 and AQ30002 swrA⁻, had very apparent dose-responses starting at about 16 oz/acre going all the way up to 128 oz/acre that resulted in greener and larger leaves than the H$_2$O control. At lower rates (4-16 oz/acre) the AQ30002 swrA⁻ treatments looked greener than the corresponding treatments in the QST713.

Figure 28:
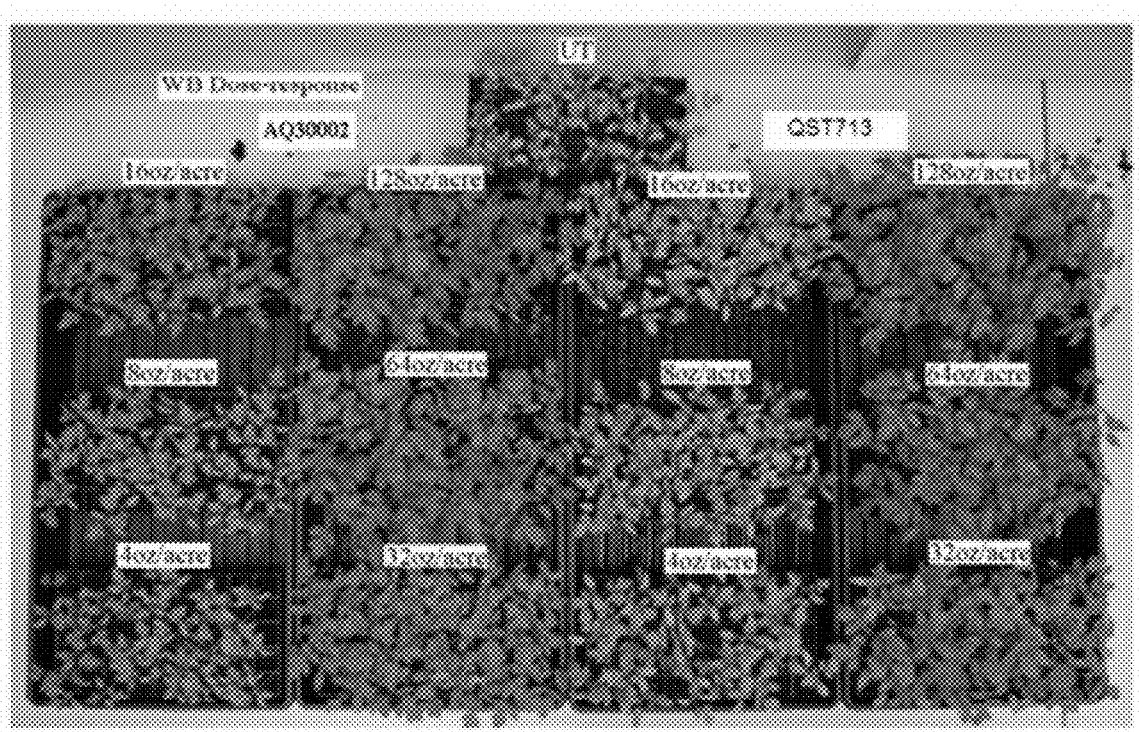
FIG. 28 shows tomato plants treated with increasing doses of AQ30002 swrA− ("AQ30002") and QST713 (a mixture of wild type swrA+ and sandpaper swrA− cells in ratios as found in the SERENADE® product, see, e.g., Example 3 and FIG. 4) ("QST713").
Figure 29:
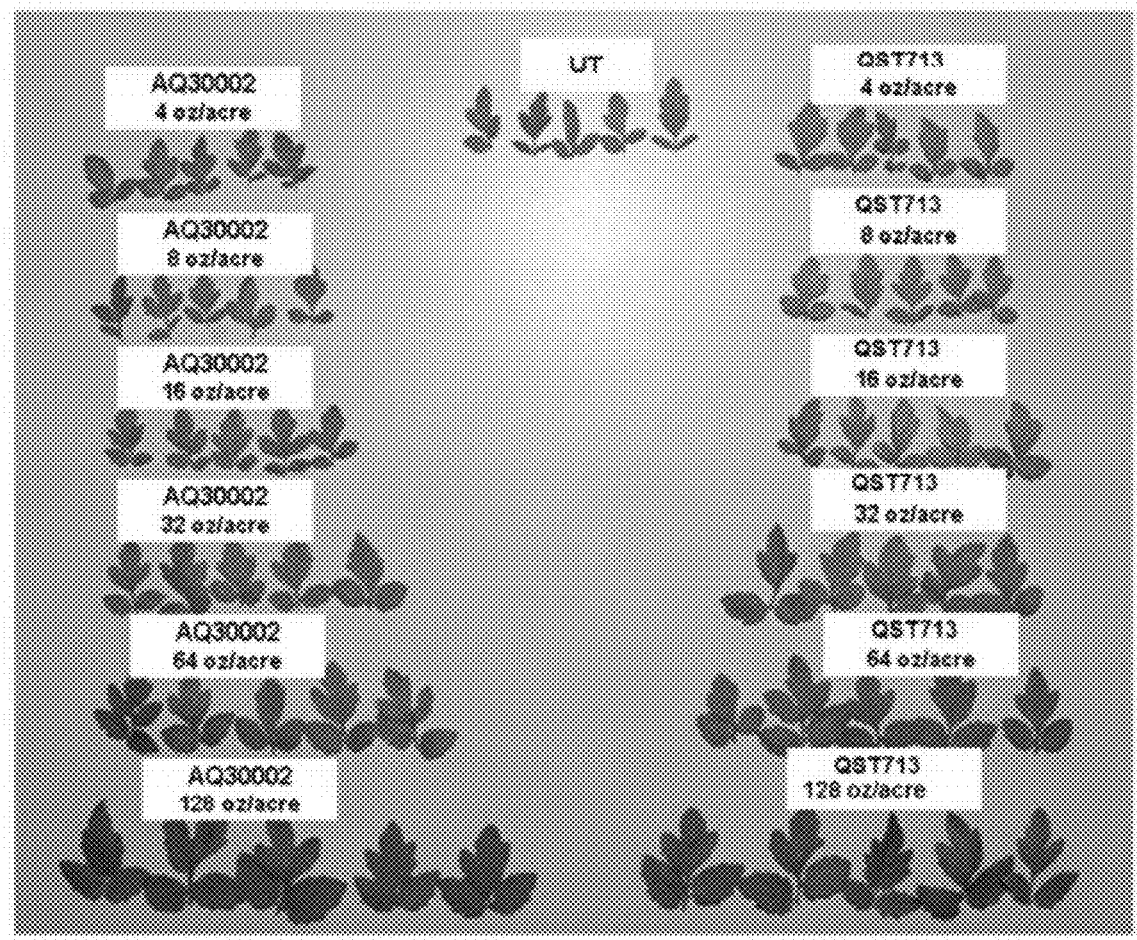
FIG. 29 is a comparison of individual leaves of tomato plants treated with increasing doses of AQ30002 swrA− ("AQ30002") and QST713 (a mixture of wild type swrA+ and sandpaper swrA− cells in ratios as found in the SERENADE® product, see, e.g., Example 3 and FIG. 4) ("QST713").
Figure 30:
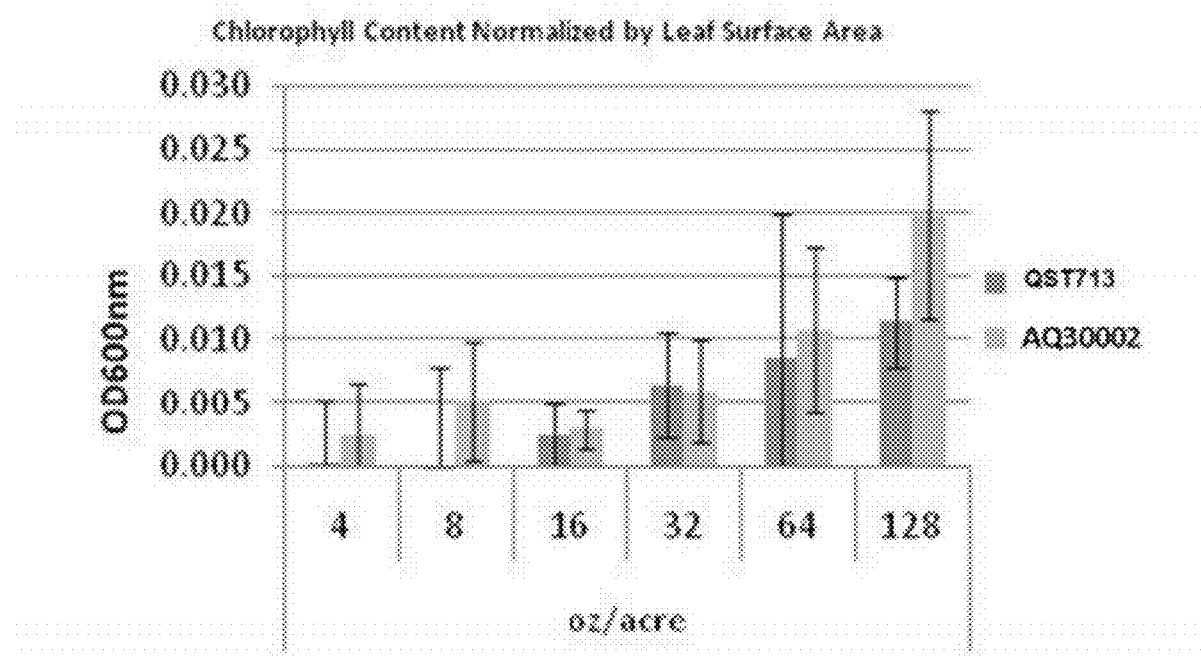
FIG. 30 represents the chlorophyll content in tomato plants treated with increasing doses of AQ30002 swrA− ("AQ30002") and QST713 (a mixture of wild type swrA+ and sandpaper swrA− cells in ratios as found in the SERENADE® product, see, e.g., Example 3 and FIG. 4) ("QST713").

Images of whole tomato plants and of individual leaves can be seen in FIGS. 28 and 29, respectively, comparing QST713 and AQ30002 swrA⁻ treatments. In addition to visual observations, chlorophyll content was also compared between rates of the QST713 and AQ30002 swrA⁻ whole broth. Although not statistically significant, there was a constant trend that leaves harvested from the AQ30002 swrA⁻ treatments had higher chlorophyll amounts than did the QST713 treatments at the corresponding rates (except for at 32 oz/acre where both appeared to have the same amount of chlorophyll). See FIG. 30.

Example 17

Activity of AQ30002 in Tomato Plant Growth Promotion

Whole broth from each of *Bacillus subtilis* QST713 (i.e., a mixture of wild type and sandpaper-like cells as found in SERENADE®, see FIG. 4) and AQ30002 swrA⁻ was prepared for use as an in situ seed treatment. A seed flask containing Luria Broth (LB) was inoculated by picking one colony off of the NA plate, and these flasks will be set to shake at 30° C. and 200 rpm. The next day, 5 ml of the seed flask was inoculated into Medium 2. Medium 2 will contain 5% peptone, 5% dextrose, 3% yeast extract, 3% malt extract, 1.5% proflo cotton seed extract, 10% soy flour and 0.5% MgSO$_4$×7H$_2$O).

Prior to seed treatment the final concentrations of the whole broths was diluted to a 64 oz/acre rate of the commercial SERENADE® product based on CFU/ml. 64 oz/acre refers to the number of colony forming unit per seed, or 2.2×10⁸ CFU/plant. The amounts used herein were calculated based on the cfus/ml of the whole broths.

Plug trays (Hummert, catalog number 14-3128) were filled with seed germination mix, and each cell was seeded with one seed. 'QualiT 21' tomato seeds will be used. Each plug tray was then treated with 2 ml of whole broth sample with the untreated controls receiving 2 ml of water. These trays were placed under high-intensity lights (~300 Einsteins, set to a 16-hour light/8-hour dark schedule) at room temperature. Watering was done as needed. No fertilizer was used.

Tomato plants were observed for plant growth promotion traits two weeks after drenching the seeds. We hypothesized that the plants treated with AQ30002 would all appear greener, taller and generally healthier than plants treated with water. We also hypothesized that the dry weights of all plant tissues treated with AQ30002 would be significantly higher than those of corresponding tissues from untreated plants. However, the results showed that Medium 2 (applied to plants as a control) promoted plant health. Therefore, Applicants were not able to draw definitive conclusions from this assay.

Example 18

In Planta Activity of AQ30002 Against *Pythium ultimum* and *Rhizoctonia solani*

QST713 (i.e., a mixture of wild type and sandpaper-like cells as found in SERENADE®, see FIG. 4) and AQ30002 swrA⁻ strains were grown in Medium 2 (5% peptone, 5% dextrose, 3% yeast extract, 3% malt extract, 1.5% proflo cotton seed extract, 10% soy flour and 0.5% MgSO$_4$×7H$_2$O) and the whole broths were tested against *Pythium ultimum* and *Rhizoctonia solani* at 20% whole broth concentration. The plant pathogens were prepared in a "spawn bag" from Fungi Perfecti (Olympia, Wash.) containing 200 g of vermiculite and 600 ml of potato dextrose (PD) broth. The bag was with a whole plate of about one week-old *Pythium ultimum* or *Rhizoctonia solani* and allowed to grow for one week before use.

The seed germination mix was moistened with 100 ml of deionized water per liter of mix and then infested at a rate of 8 g inoculum per liter mix for *Rhizoctonia solani* and 64 g/L mix for *Pythium ultimum* and was then placed into 2.5 inch pots. Non-infested mix was also used as an uninfested control (UIC). After infestation and placing the mix into the pots, each pot in each treatment was drenched with 10 ml of its respective treatment. After drenching, each pot was planted with about 65 *Brassica* seedlings (Johnny's Broccoli for Sprouting, catalog number 2108) using a calibrated scoop). The seeds were covered with a layer of uninfested potting mix, and the pots were placed in a tray with no holes that was flooded with deionized water until all of the pots were saturated with water. The pots were placed under high-intensity lights and allowed to grow for one week before rating.

Individual seedlings in each replicate were counted for each treatment in each disease so that a quantitative number for seedling germination could be obtained. The results were compared with uninfested controls (UIC) and infested controls (IC) to determine activity. Disease control was determined by the number of seedlings that emerged and survived in the soil inoculated with the specific pathogen. There was no difference in disease control as seen before with the same strains grown in soy-based medium.

Example 19

In Planta Activity of AQ30002 Against *Phytophthora capsici*

The QST713 ((i.e., a mixture of wild type and sandpaper-like cells as found in SERENADE®, see FIG. 4) and AQ30002 swrA⁻ strains were grown in Medium 2 (5% peptone, 5% dextrose, 3% yeast extract, 3% malt extract, 1.5% proflo cotton seed extract, 10% soy flour and 0.5% $MgSO_4 \times 7H_2O$) and the whole broths was tested against *Phytophthora capsici* at 20% concentration. Zoospores of *Phytophthora capsici* were prepared on V-8 agar and were diluted to $2 \times 10^4$ zoospores/ml for inoculation (10 ml/plant).

Two-week-old peppers (variety 'California Wonder') were planted in potting mix, drenched with 10 ml of whole broth treatment, and inoculated with *Phytophthora capsici* the next day. One week later, the test was rated for kill/no kill out of the total number of peppers for each treatment. These ratings were compared to the infested controls (IC) and the uninfested controls. The chemical fungicide Aliette, which contains aluminum tris(O-ethyl phosphonate), was tested at 3.2 mg/ml and at 1.6 mg/ml.

To monitor the progression of the disease in the pepper plants and the protection afforded by treatment with QST713 or AQ30002 the plants were monitored over an 8 day period. Treatment with AQ30002 protected plants for a longer duration with a greater number of total plants surviving than did treatment with QST713 (i.e., a mixture of wild type and sandpaper-like cells as found in SERENADE®, results not shown).

Example 20

Tomato Plant Growth Promotion by a *Bacillus subtilis* 3610 SwrA⁻ Mutant

Whole broth from each of 3610WT *Bacillus subtilis* (i.e., wild type cells, referred to herein as 3610 or 3610WT) and 3610 swrA⁻ was prepared as a seed drench. The 3610WT *Bacillus subtilis* is described in Kearns, 2004. The 3610 swrA⁻ mutant refers to the swrA⁻ mutant described in Kearns, 2004, having an insertion in a contiguous stretch of eight A:T base pairs occurring at position 26-34 in 3610. Each strain was streaked out onto Nutrient Agar (NA) 3 days before inoculation into a seed flask. The seed flask containing Luria Broth (LB) was inoculated by picking one colony off of the NA plate, and these flasks were set to shake at 30° C. and 200 rpm. The next day, 5 ml of the seed flask was inoculated into a soy-based medium.

Prior to seed drench, the final concentrations of the whole broths were diluted to a 64 oz/acre rate of the commercial SERENADE® product based on CFU/ml. 64 oz/acre refers to the number of colony forming unit per seed, or $2.2 \times 10^8$ CFU/plant. The amounts used herein were calculated based on the cfus/ml of the whole broths.

Plug trays (Hummert, catalog number 14-3128) were filled with Sunshine #3 potting mix (Sun Gro Horticulture) (moistened and sterilized for one hour, then left to vent for three days), and each cell was seeded with one seed. 'Spring Treat Hybrid' corn seeds, 'Derkwin' wheat seeds, and 'QualiT 21' tomato seeds were used. Thus, the tests included both monocotyledonous species (i.e., corn and wheat) and dicotyledonous species (i.e., tomato). Each plug tray was then treated with 2 ml of whole broth sample with the untreated controls receiving 2 ml of water. Plug trays were watered from the bottom by flooding a tray with no holes and placing the plug trays inside. These trays were placed under high-intensity lights (~300 Einsteins, set to a 16-hour light/8-hour dark schedule) at room temperature. Watering was done as needed. No fertilizer was used.

Tomato plants were observed for plant growth promotion traits two weeks after drenching the seeds. The leaf surface area was then quantified.

Figure 31:
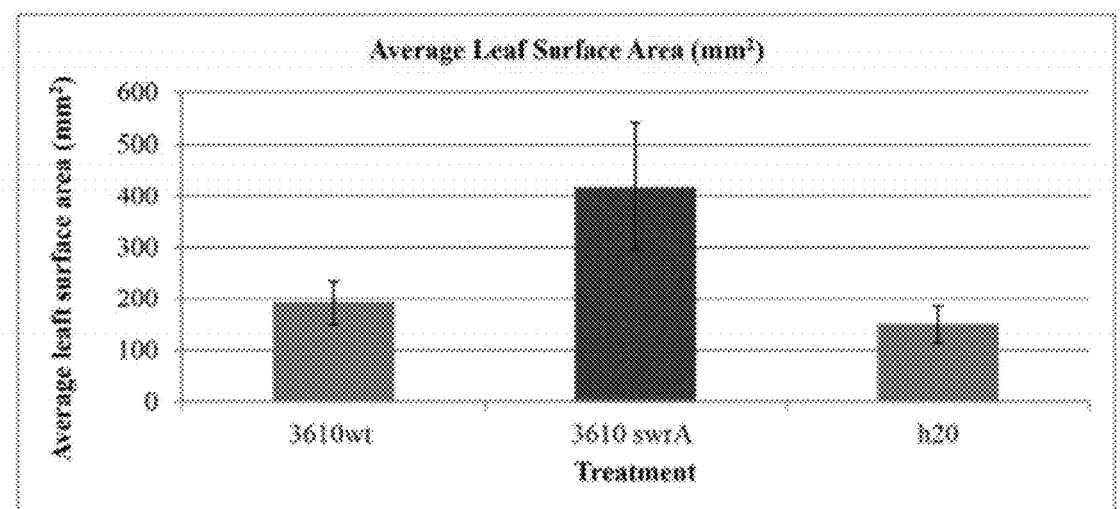
FIG. 31 represents average leaf surface area (of five replications) of plants treated with 3610WT and 3610swrA− (designated as 3610swrA in the graph).
Figure 32:
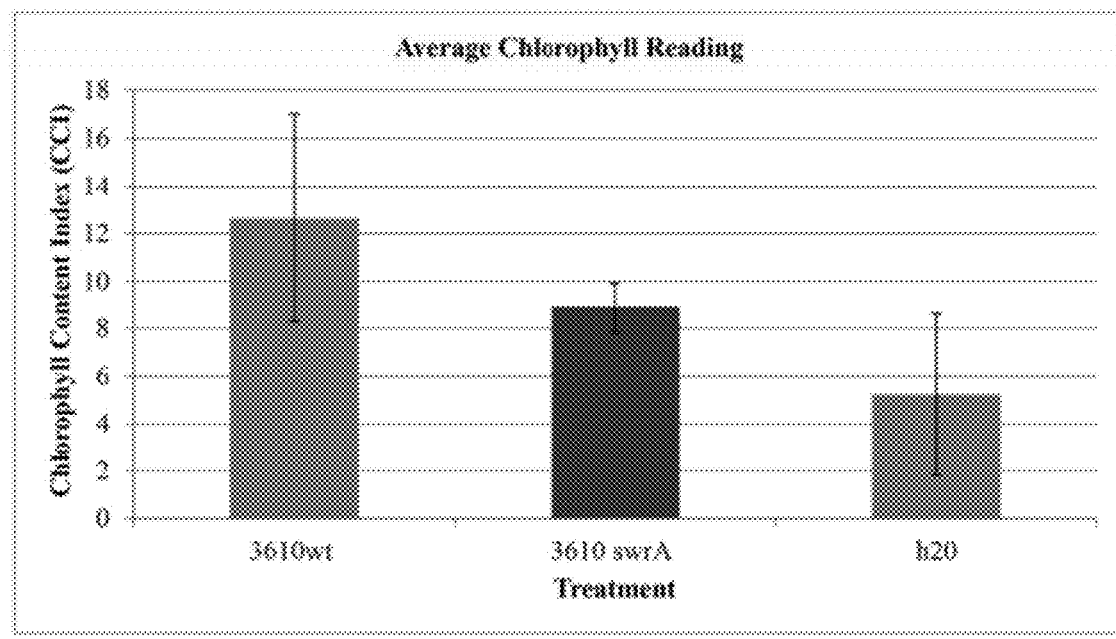
FIG. 32 represents chlorophyll readings of plants treated with 3610WT and 3610 swrA− (indicated in the figure as 3610swrA). Results are an average of chlorophyll levels in the first true leaf of five randomly selected tomato seedlings.

The 3610 WT-treated plants did not appear greener or taller from the water-treated plants. In contrast, 3610 swrA⁻ treated plants appeared greener and taller than 3610WT-treated plants (data not shown). These results were confirmed quantitatively by looking at the leaf surface area of 3610 swrA⁻ treated plants (FIG. 31). Average chlorophyll readings of the first true leaf of five randomly selected tomato seedlings did not show higher chlorophyll levels for 3610 swrA⁻ treated plants (FIG. 32).

Note that similar experiments were conducted with wheat and corn. 3610 WT-treated plants and 3610 swrA⁻ treated plants were comparable in terms of height and color, based on qualitative observations, although both were taller and greener than the water-treated controls. However, these types of differences are very subtle in monocots (in a short term greenhouse assay) so might not have been discernible through this qualitative study.

Example 21

In Planta Activity of 3610 swrA⁻ Against *Phytophthora capsici*

The 3610WT and 3610 swrA⁻ strains, as described above, were grown in flasks in a soy-based medium and the whole broths were tested against *Phytophthora capsici* at 20% concentration. The *Phytophthora capsici* was grown on V-8 agar for 1-2 weeks. At the end of this time, the outer ¼ inch of the plate was cut out and discarded with sterile tweezers. The plate was flooded with sterile deionized water up to the level of the agar and left at room temperature under light for 2 days to facilitate sporangial production. The plate was then chilled for an hour and a half at 4° C. and then left at room temperature for another hour to release the zoospores in the sporangia. Zoospore concentration was quantified under the microscope with a hemacytometer by capturing 3 photographs at random and averaging the zoospore count. The zoospore concentration was then diluted to $2 \times 10^4$ zoospores/ml for inoculation (10 ml/plant).

Figure 33:
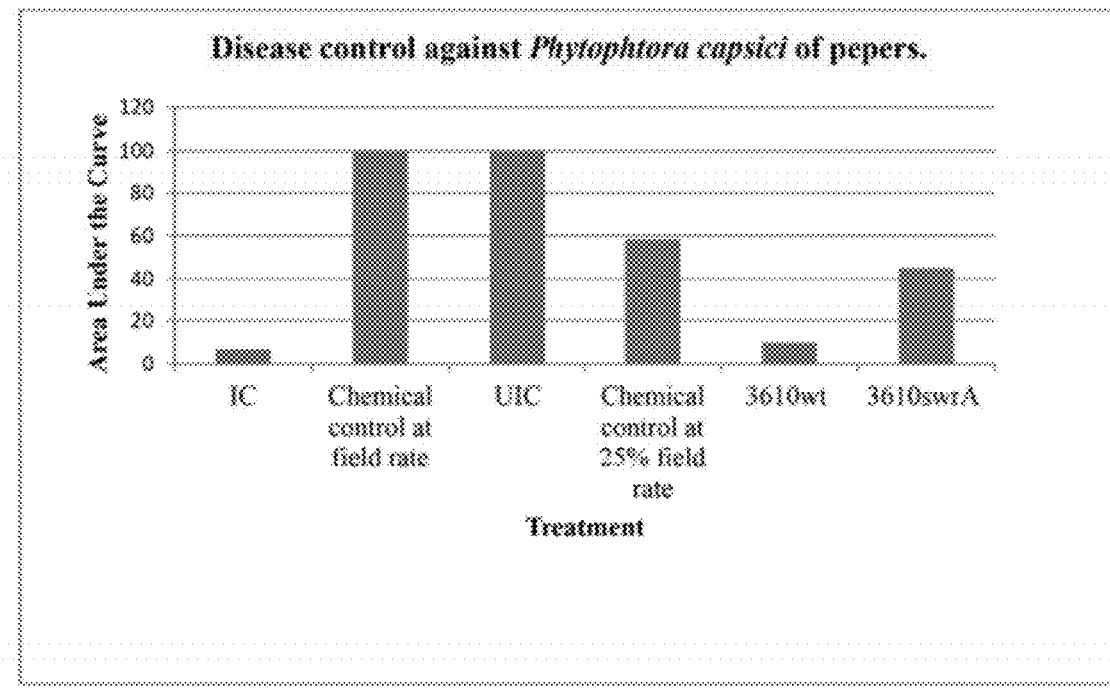
FIG. 33 represents activity of 3610WT and 3610swrA⁻ (designated as 3610swrA in the graph) against *Phytophtora capsici* of pepper.

Two-week-old peppers (variety 'California Wonder') planted in potting mix were each drenched with 10 ml of whole broth treatment, and inoculated with *Phytophthora capsici* the next day. The plants were monitored over an 8 day period. These ratings were then compared to the infested controls (IC) and the uninfested controls (see. FIG. 33). The chemical fungicide Aliette, which contains aluminum tris(O-ethyl phosphonate), was also tested at 3.2 mg/ml and at 1.6 mg/ml.

Treatment with 3610 swrA− protected plants for a longer duration with a greater number of total plants surviving than did treatment with 3610 (see FIG. 33).

Example 22

Activity of AQ30002 Against Nematodes

Studies were conducted with cucumber seeds var. *Sultan* to determine activity of AQ30002 against *Meloidogyne javanica*, root knot nematode. 50 ml centrifuge tubes containing 20 g sand and one ungerminated seed were treated with different rates of whole broth of AQ30002. To obtain whole broth cultures of AQ30002, seed flasks containing Luria Broth (LB) were inoculated with AQ30002 and grown overnight at 30° C. The next day, aliquots from each seed flask were inoculated into 200 ml of a soy-based medium in a 1 L shake flask and grown until sporulation. Briefly, the shake flask culture was maintained at a temperature between 30° C. and 32° C. and at a shaker setting of 200 to 220 rpm. After approximately 3 days of incubation, when cell growth and metabolite production had stopped, the culture broth was harvested.

The treated seeds were allowed to germinate and grow in the greenhouse. Four to five days after treatment (DAT) each tube was inoculated with 100 second-stage juvenile root knot nematodes. 10 DAT the seedlings were scored for percentage root galling on a 0-4 scale, which is described in Table 4.

The roots were then stained with acid fuschin to observe nematode penetration and development and observed under a Leica dissecting microscope. For nematode penetration, the total nematode juveniles inside each root were counted. For nematode development, total fat juveniles including late second stage juvenile (J2's) and third stage juvenile (J3's) were counted. Penetration of nematodes into the root and nematode development after penetration were scored as detailed in Table 4. For details on techniques used, see C. O. Omwega, et al., "A Nondestructive Technique for Screening Bean Germ Plasm for Resistance to *Meloidogyne incognita*," Plant Disease (1988) 72(11): 970-972).

TABLE 4

Rating Scheme for Nematode Antagonistic Activity of Bacterial Whole Broths. The galling index was based on the percentage of root galling. The penetration scale was calculated as the mean total number of juvenile nematodes relative to the number of juvenile nematodes in the untreated control (UTC). The development scale reflects the total number of fat juvenile nematodes (late J2 stage/J3 stage) inside the root.

| Galling Index | | Penetration Scale | | Development scale | |
| --- | --- | --- | --- | --- | --- |
| 0 | None | 0 | None | 0 | None |
| 1 | 1-24% | 1 | 1-10% | 1 | 1-3 |
| 2 | 25-49% | 2 | 11-50% | 2 | 3-10 |
| 3 | 50-74% | 3 | 51-75% | 3 | 11-30 |
| 4 | >75% | 4 | 76-100% | 4 | >30 |

Figure 34:
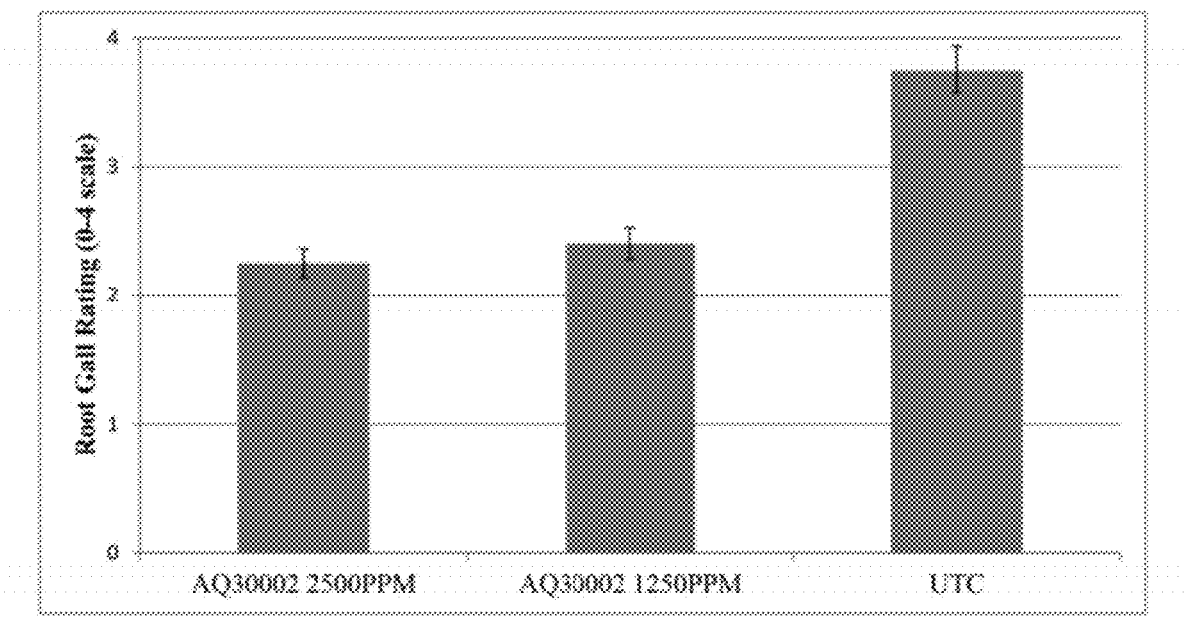
FIG. 34 shows the effect of AQ30002 swrA⁻ ("AQ30002") whole broth treatment on galling of roots infested with root knot nematodes.
Figure 35:
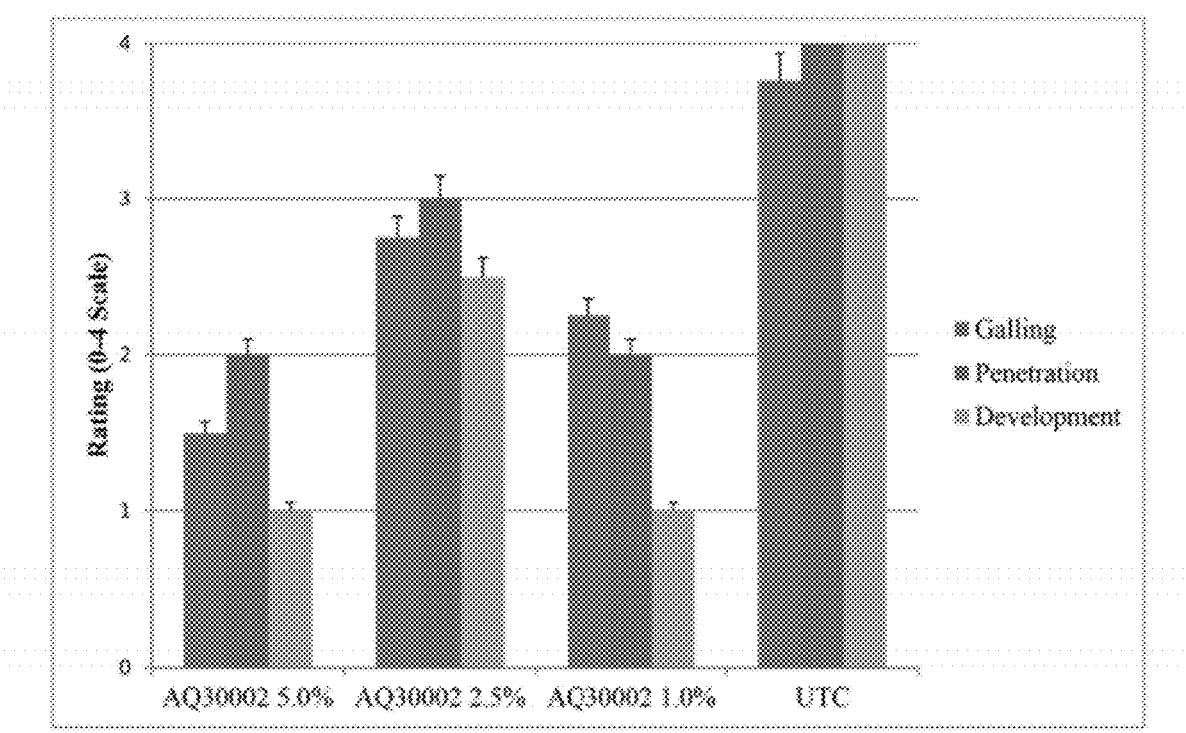
FIG. 35 shows the effect of treatment with AQ30002 swrA⁻ ("AQ30002") at various rates on seedlings infested with root knot nematodes. Specifically, results show extent of root galling and effects on nematode penetration and development.

FIG. 34 shows that application of AQ30002 whole broth decreases root galling. FIG. 35 shows that application of various rates of AQ30002 decrease galling, penetration and development compared to the untreated control. Note that because the data is based on the above rating system it is not always possible to observe a dose response.

Example 23

Efficacy of AQ30002 for Control of Root-Knot Nematodes in Tomatoes

Another experiment was conducted with tomato seeds to test efficacy of AQ30002 against root knot nematode (*M. javanica*) eggs. AQ30002-Batch1 and AQ30002-Batch2 were prepared in bioreactors at different times. Briefly, a vial of stock culture was thawed and transferred to a sterilized flask of Difco Nutrient Broth. The flask culture was then incubated on a rotary shaker at a temperature between 28° C. and 32° C. at a rotation speed of 200 to 220 rpm to promote cell growth and obtain high cell density and then added to 12 L of a soy-based growth medium in a 20 L bioreactor. The bioreactor was set at a temperature setting between 30° C. and 32° C., at an agitation setting of 500 to 1000 rpm, to a pH buffered between 6 and 8, and to an aeration between 0.5 and 1.0 VVM. After approximately 3 days of incubation, when cell growth and metabolite production had stopped, the culture broth was harvested.

Figure 36:
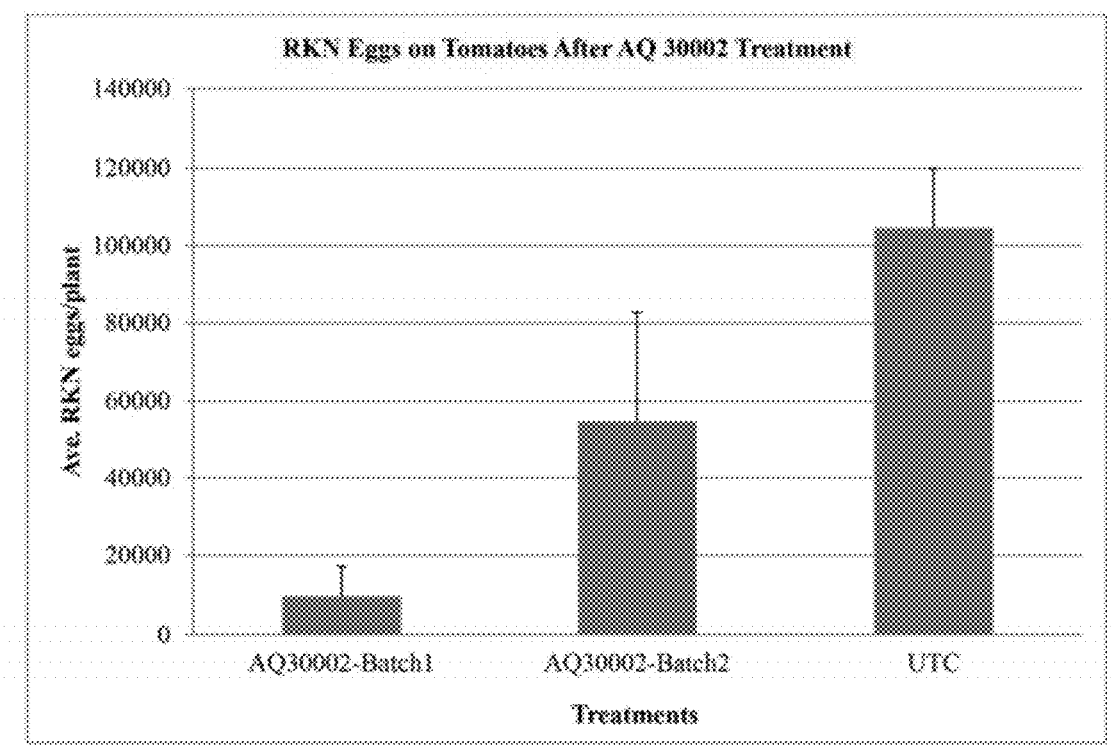
FIG. 36 represents root knot nematode eggs per plant treated with various batches of AQ30002 swrA⁻ ("AQ30002") as compared to untreated plants (designated as UTC in the figure).

Three-week old tomato plants were treated with AQ30002 by drench. Pots were then kept in a greenhouse for ten days before being inoculated with 5000 root-knot nematode ("RKN") eggs per pot. Plants were harvested forty-two days after nematode inoculation. Eggs were collected from the roots of the tomato plants using a 1% NaOCl solution as detailed in Hussey R S, Barker K R, "A Comparison of Methods of Collecting Inocula of *Meloidogyne* spp., Including a New Technique," Plant Disease Reporter, 1973; 57:1025-1028. AQ30002 decreased the number of root knot nematode eggs observed per plant. Data represents direct counts of eggs rather than a scoring system. Results as compared to an untreated sample (UTC) are shown in FIG. 36.

Example 24

Screening for swrA− Spontaneous Mutants

Screening for swrA− spontaneous mutants from *Bacillus subtilis* clade strains can be conducted as follows. 250 mL of Luria Broth (LB) liquid media in a 1 liter flask is inoculated with a single colony from a suitable agar plate. This is cultured for 16-20 hours at 30° C. at 200 rpm in an orbital shaker.

The resulting culture will be serially diluted to $1\times10^3$, $1\times10^6$, and $1\times10^9$ in phosphate buffered solution and 100 µl of each dilution plated onto suitable agar plate and incubated for 12-16 hours at 37° C. Dilution plates which yielded 150-200 individual colonies are moved to 4° C. refrigerator for 24-48 hours. Following 24-48 hours at 4° C., potential swrA⁻ isolates are apparent due to the intense white, sandpaper-like morphology on the agar plates whereas isolates which are swrA⁺ do not exhibit this morphology and often become translucent and difficult to see on the plate.

Potential swrA⁻ mutants are collected and cultured in LB overnight at 30° C. at 250 rpm. Genomic DNA isolation is performed using the MoBio ultraClean® Microbial DNA Isolation Kit centrifugation protocol provided with the MoBio Kit. Mutants are identified by PCR and sequencing of the swrA locus, using the genomic DNA isolated above and PCR amplify using PCR primer list below for the Bacillus species specific or general primers that are of interest for the strain being screened.

```
Bacillus amyloliquefaciens
                              (SEQ ID NO: 14)
BA_swrA_PCRF    AAACAATGAAAAAGCCGTTCTGG (SEQ ID NO: 15)
BA_swrA_PCRR    TCCGTGATAATCAAAAGGCC Bacillus pumilus
                              (SEQ ID NO: 16)
BP_swrA_PCRF    AAAGAATGATCTTCAGCTAC (SEQ ID NO: 17)
BP_swrA_PCRR    ATTAAAAACAGACCGACCGC Bacillus licheniformis
                              (SEQ ID NO: 18)
BL_swrA_PCRF    CATAATGAATAGAATTGACCCG (SEQ ID NO: 19)
BL_swrA_PCRR    GAAACCCAGCTTGTCTAAAG Bacillus subtilis
                              (SEQ ID NO: 20)
BS_swrA_PCRF    AATGAAACTTTTGCAAGTTGCC (SEQ ID NO: 21)
BS_swrA_PCRR    AATCGATATTCCGAGTCCAC Unidentified Bacillus strains
                              (SEQ ID NO: 22)
Bac_swrA_PCRF   ACGCTKTAYAARTGGCTSAC (SEQ ID NO: 23)
Bac_swrA_PCRR   TCATCCAKAYCGTVACATTDG
```

PCR protocol and reaction conditions for amplifying swrA locus plus approximately 150 nucleotides of 3' and 5' UTR are shown below:

PCR Reaction Components per reaction
2.5 µl gDNA—≤250 ng final
5 µl GoTAQ 5× Buffer—1× final
1 µl GoTAQ MgCl$_2$—1 mM final
0.5 µl 10 mM dNTPs—0.2 mM final
0.25 µl 0.1 nMol Forward Primer—1 pMol final
0.25 µl 0.1 nMol Reverse Primer—1 pMol final
0.25 µl GoTAQ—1× final
15.25 µl H$_2$O
25 µl total reaction volume
Suitable PCR cycling conditions shown below:
94° C. 2:00 min
94° C. 0:30 min
55° C. 0:30 min
72° C. 2:00 min
25 cycles
72° C. 5:00 min
4° C. forever 5% of the PCR reaction is visualized on a 1% Agarose gel with suitable DNA dye and sizing ladder. PCR products are single bands approximately 700 nucleotides long. Clean 5 µl of amplified DNA prior to sequencing with 2 µl of ExoSap-It enzyme. Cleaned amplicon is sequenced with either the forward or reverse PCR primer using Sanger sequencing. The swrA locus sequence is compared to a wildtype reference strain, preferably of the same species, using ClustalW sequence alignment tool and any nucleic acid changes, deletions or insertions identified.

Mutation in the swrA locus leads to altered colony morphology, enhanced chaining during liquid growth compared to wild type swrA⁺, loss of swarming on 0.7% agar for swarming Bacilli, and/or more robust root biofilm formation.

Example 25

Generating swrA⁻ Mutants by Various Methods

Antisense constructs for swrA knockdown in swrA⁺ Bacillus strains may be constructed by PCR amplifying the reverse complement of the swrA coding region from genomic DNA derived from either QST713 or other swrA⁺ Bacilli. PCR primers are designed with restriction enzymes compatible for insertion into previously constructed endoPro_swrA plasmid vector designed to be compatible with the Integrative and Conjugative Element (ICE) element present in Bacillus subtilis MMB869 (Wiep Klaas Smits and Alan D. Grossman, "The Transcriptional Regulator Rok Binds A+T-Rich DNA and Is Involved in Repression of a Mobile Genetic Element in Bacillus subtilis," PLoS Genetics (2010) 6(11): e1001207; Catherine A. Lee, et al., "Identification and characterization of int (integrase), xis (excisionase) and chromosomal attachment sites of the integrative and conjugative element ICEBs1 of Bacillus subtilis," Molecular Microbiology (2007) 66(6): 1356-1369). The swrA coding region is inserted from endoPro_swrA plasmid by restriction digest and the reverse complement of the swrA gene inserted. The swrA antisense construct may be confirmed as correctly inserted into plasmid vector without PCR introduced nucleic acid changes by sequencing purified plasmid DNA. See Example 7.

Mutation in the swrA locus leads to altered colony morphology, enhanced chaining during liquid growth compared to wild type swrA⁺, loss of swarming on 0.7% agar for swarming Bacilli, and/or more robust root biofilm formation.

The mariner based transposon TnYLB-1 (Le Breton, Y., Mohapatra, N. R., and W. G. Haldenwang, 2006. In Vivo Random Mutagenesis of Bacillus subtilis by Use of TnYLB-1, a mariner-Based Transposon, Appl. Environ. Microbiol. 72:327-333) may also be used to generate swrA⁻ mutants. Due to the presence of the Himar-1 transposase, mariner recognizes, excises, and inserts itself at two inverted insertion (IS) elements carrying with it any exogenous DNA residing between the IS elements. TnYLB is a modified mariner transposon for use with Bacillus. A kanamycin resistance marker is inserted between the IS elements for rapid selection of integrants. The TnYLB is delivered on the plasmid pMarA (Le Breton et al., 2006—from above). In addition to conferring Kanamycin resistance to the host Bacillus, insertion commonly generates loss of function mutations due to the disruption of an open reading frame. By screening for loss of swarming ability or sandpaper like colony morphologies and confirmation of transposon insertion at the swrA locus, swrA⁻ mutant strains can be generated.

The pMarA plasmid which encodes the mariner IS elements, kanamycin resistant gene, the himar1 gene outside the IS elements (to ensure that the element is stable in the genome) is introduced to a swrA+ *Bacillus* strain by electroporation. The pMarA plasmid backbone has an mls (Macrolide-Lincosamide-Streptogramin B) resistance gene to ensure loss of the pMarA plasmid following transposition. It has a temperature sensitive origin which allows for mls or kanamycin selection. The swrA+ *Bacillus* strain containing the pMarA plasmid is grown in 3 ml LB+mls overnight at room temperature in a roller drum. The swrA+ *Bacillus* strain containing the pMarA plasmid is dilution plated onto LB (to determine total colony forming units) and LB with 20 µg/ml kanamycin (to determine number of transposants) and incubated at 45° C. overnight. Colonies are restruck onto LB plates with kanamycin and mls plates. Kanmycin resistant/mls sensitive colonies are retained for further analysis. Potential transposon insertions into the swrA locus have sandpaper-like colony morphology, decreased swarming ability on 0.7% LB agar plates.

Upon identification of putative swrA transposon insertions, the exact location of the insertion is determined by inverse PCR (iPCR). Genomic DNA from transposon mutants is isolated and digested with a high frequency restriction enzyme such as Sau3 AI or Taq1. The digested DNA is re-ligated to form circularized DNA fragments. Circularized fragments which contain one IS element from the transposon and neighboring host genomic DNA successfully yield PCR fragments when using primers designed within the TnYLB transposon.

```
iPCR primers:
                                        (SEQ ID NO: 24)
2507      AGGAGGAATTCTACGGAAGTGTTAATTTCATAC (SEQ ID NO: 25)
2508      TCCATGCTCGAGGAAGAGC (SEQ ID NO: 26)
2509      ACAGAAAGTCTCGAGATCGTC (SEQ ID NO: 27)
2510      CTCCTGGATCCTCAATGGCTTTTTGGAAATCAG
```

The iPCR products are purified and sequenced with the outward facing amplification primer. Sequence tags are generated for each mutant and blasted against the genomic sequence proximal to the swrA locus. Transposons which contain swrA locus genomic DNA likely disruptive swrA function.

Knock down of the swrA locus by transposition leads to altered colony morphology, enhanced chaining during liquid growth compared to wild type swrA+, loss of swarming on 0.7% agar for swarming Bacilli, and/or more robust root biofilm formation.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. swrA mutant cells of *Bacillus subtilis* QST713 deposited under the accession number NRRL B-50420, wherein the mutant cells consist of a base pair deletion at position 26 of SEQ ID NO: 1.

2. The swrA mutant cells of the *Bacillus subtilis* QST713, wherein the mutant cells are of the strain AQ30002 or QST30002 deposited under the accession number NRRL B-50421.

3. A composition comprising spore-forming bacterial cells, wherein at least 25% of the total spore-forming bacterial cells in the composition are the swrA mutant cells of claim 1.

4. A composition comprising mutant cells derived from *Bacillus subtilis* QST713 cells deposited under the accession number NRRL B-50420, wherein the mutant cells have a mutation in the swrA gene, wherein the mutation is a base pair deletion at position 26 of SEQ ID NO: 1 and wherein the mutant cells have the ability to form a compact biofilm on a plant surface, the ability to enhance the health of a plant, and/or the ability to increase the yield of a plant compared to the *Bacillus subtilis* QST713 cells having the wild type swrA gene.

5. The composition of claim 4, wherein the mutant cells are of the strain AQ30002 or QST30002 deposited under the accession number NRRL B-50421.

6. The composition of claim 4, wherein the composition comprises at least one carrier.

7. The composition of claim 4, wherein the composition further comprises an active ingredient in addition to the mutant cells.

8. The composition of claim 7, wherein the active ingredient is a chemical or another strain of bacteria.

9. The composition of claim 8, wherein the active ingredient is selected from the group consisting of a herbicide, a fungicide, a bactericide, an insecticide, a nematicide, a miticide, a plant growth regulator, a plant growth stimulant, and a fertilizer.

* * * * *

SEQUENCE LISTING

```
<160> NUMBER OF SEQ ID NOS: 43

<210> SEQ ID NO 1
<211> LENGTH: 351
<212> TYPE: DNA
<213> ORGANISM: Bacillus subtilis

<400> SEQUENCE: 1
ttgaagaggg caagtattgt gcgtgaaaaa aaatattatg aattagtgga acaactaaaa      60
gacagaacaa aagacgtcac attttcatca acaaaagcac taagtcttct tatgctgttc     120
agcagatacc tggtcaatta cacaaatgtt gaatgcgttc acgaaatcaa tgaagagtgt     180
gcgaagcatt atttcactta cttaatgaaa aaccataaac gtttaggaat taatctgacg     240
gatattaagc ggtccatgct tctgatcagc ggcgtgatcg aggtggaggt tgaccactat     300
ctgaaagatt tctctctctc aaatgtaacg ttgtggatga cggaagagag a              351

<210> SEQ ID NO 2
<211> LENGTH: 117
<212> TYPE: PRT
<213> ORGANISM: Bacillus subtilis

<400> SEQUENCE: 2
```

```
Met Lys Arg Ala Ser Ile Val Arg Glu Lys Lys Tyr Tyr Glu Leu Val
1               5                   10                  15

Glu Gln Leu Lys Asp Arg Thr Lys Asp Val Thr Phe Ser Ser Thr Lys
            20                  25                  30

Ala Leu Ser Leu Leu Met Leu Phe Ser Arg Tyr Leu Val Asn Tyr Thr
        35                  40                  45

Asn Val Glu Cys Val His Glu Ile Asn Glu Glu Cys Ala Lys His Tyr
    50                  55                  60

Phe Thr Tyr Leu Met Lys Asn His Lys Arg Leu Gly Ile Asn Leu Thr
65                  70                  75                  80

Asp Ile Lys Arg Ser Met Leu Leu Ile Ser Gly Val Ile Glu Val Glu
                85                  90                  95

Val Asp His Tyr Leu Lys Asp Phe Ser Leu Ser Asn Val Thr Leu Trp
            100                 105                 110

Met Thr Glu Glu Arg
        115

<210> SEQ ID NO 3
<211> LENGTH: 350
<212> TYPE: DNA
<213> ORGANISM: Bacillus subtilis

<400> SEQUENCE: 3
ttgaagaggg caagtattgt gcgtgaaaaa aatattatga attagtggaa caactaaaag      60
acagaacaaa agacgtcaca ttttcatcaa caaaagcact aagtcttctt atgctgttca     120
gcagatacct ggtcaattac acaaatgttg aatgcgttca cgaaatcaat gaagagtgtg     180
cgaagcatta tttcacttac ttaatgaaaa accataaacg tttaggaatt aatctgacgg     240
atattaagcg gtccatgctt ctgatcagcg gcgtgatcga ggtggaggtt gaccactatc     300
tgaaagattt ctctctctca aatgtaacgt tgtggatgac ggaagagaga             350

<210> SEQ ID NO 4
<211> LENGTH: 351
<212> TYPE: DNA
<213> ORGANISM: Bacillus subtilis

<400> SEQUENCE: 4
ttcaagaggg caagtattgt gcgtgaaaaa aaatattatg aattagtgga acaactaaaa      60
gacagaacaa agacgtcac attttcatca caaaagcac taagtcttct tatgctgttc     120
agcagatacc tggtcaatta cacaaatgtt gaatgcgttc acgaaatcaa tgaagagtgt     180
gcgaagcatt atttcactta cttaatgaaa aaccataaac gtttaggaat taatctgacg     240
gatattaagc ggtccatgct tctgatcagc ggcgtgatcg aggtggaggt tgaccactat     300
ctgaaagatt tctctctctc aaatgtaacg ttgtggatga cggaagagag a              351

<210> SEQ ID NO 5
<211> LENGTH: 351
<212> TYPE: DNA
<213> ORGANISM: Bacillus amyloliquefaciens

<400> SEQUENCE: 5
ttgaagaggg caagtattgt gcgtgaaaaa aaatattatg aattagtgga acaactaaaa      60
gaccgaacaa agacgttac attttcatca caaaagcac taagtcttct tatgctgttc     120
agcagatacc tggtcaatta cacaaatgtt gaatgtgttc acgatatcaa tgaggagtgt     180
```

```
gcaaagcatt atttcaccta cttaatgaaa aaccataaac gtttaggaat caatctgacg      240
gatattaaac ggtccatgct tttgatcagc ggtgtaatcg aggtggaagt cgaccactat      300
ctgaaagatt tctctctttc aaatgtgacg ttgtggatga cggaagagag a               351
```

<210> SEQ ID NO 6
<211> LENGTH: 351
<212> TYPE: DNA
<213> ORGANISM: Bacillus pumilus

<400> SEQUENCE: 6

```
ttgaaaaggg caagtattgt gagagagaaa aaatattacg agttggtaga ggagcttaag       60
agtcgtacga aagatgtgac gttttccgct acaaaggcat taagtctgct catgctgtta      120
agcaggtact tggtcaatta cacaacggta gaatcagtcg acgaaataga tgaagactgt      180
gctgagatat acttcaatta tttaatggat aatcataaga gacttggtat aaacttaacc      240
gacatcaaga gatcgatgca gctgcttggc ggcatactag atgtagatgt caatcactac      300
ttaaaagatt tttcactgtc gaatgtcaca ctttggatga atcaggagaa a               351
```

<210> SEQ ID NO 7
<211> LENGTH: 351
<212> TYPE: DNA
<213> ORGANISM: Bacillus subtilis
<220> FEATURE:
<221> NAME/KEY: misc_feature
<222> LOCATION: (345)..(345)
<223> OTHER INFORMATION: n is a, c, g, or t

<400> SEQUENCE: 7

```
ttgaagaggg caagtattgt gcgtgaaaaa aaatattatg aattagtgga acaattaaaa       60
gacagaacac aagacgtaac attttcagct acaaaagcac taagtcttct tatgctgttc      120
agcagatatt tggtcaatta caccaatgtc gaatcagtaa atgacattaa tgaggaatgc      180
gccaaacatt attttaacta cttaatgaaa aaccataagc gattaggaat taatctgaca      240
gatataaaaa ggtcgatgca tctaatcagc gggttattgg atgtggatgt aaaccactat      300
ttaaaggatt tttcactatc gaatgtcacg ctgtggatga cgcangagag a               351
```

<210> SEQ ID NO 8
<211> LENGTH: 351
<212> TYPE: DNA
<213> ORGANISM: Bacillus pumilus

<400> SEQUENCE: 8

```
ttgaaaaggg caagtattgt gagagagaaa aaatattacg agttggtaga ggagcttaag       60
agtcgtacga aagatgtgac gttttcggct acaaaggcat taagtctact catgctgtta      120
agcaggtact tggtcaatta cacaacggta gaatcagtcg acgagatcga tgaagactgt      180
gctgagatat acttcaatta tttaatggat aatcataaga gacttggtat aaacttaacc      240
gacatcaaga ggtccatgca gcttctcggc ggcatactag atgtagatgt gaatcactat      300
ttaaaagatt tttcactgtc gaatgtcaca ctttggatga atcaggagaa a               351
```

<210> SEQ ID NO 9
<211> LENGTH: 351
<212> TYPE: DNA
<213> ORGANISM: Bacillus atrophaeus

<400> SEQUENCE: 9

```
ttgaagaggg caagtattgt gcgtgaaaaa aaatactatg aattagtgga acaattaaaa       60
```

```
gaccgaacac aagacgtaac attttcagct acaaaagcac taagtcttct aatgctcttt      120
agcagatatt tagtcaatta cacaaatgta gaatcagtga acgatattaa tgaggaatgc      180
gccgagcatt attttaatta tttaatgaaa aatcataaac ggttgggaat caatctgaca      240
gacataaaac gatcaatgct cctcatcggc ggtgtgttgg acgtcgaggt aaaccattat      300
ttaaaggatt tctctctgtc taatgtgacg ctctggatga atcaggagag a               351
```

<210> SEQ ID NO 10
<211> LENGTH: 351
<212> TYPE: DNA
<213> ORGANISM: Bacillus licheniformis

<400> SEQUENCE: 10

```
ttgaaaaggg caagtattgt gagagagaaa aaatactatg aattagtgga gcagttaaaa       60
gttcgatcac aagacgttac gttttccgct acaaaggcag taggattgct tatgctgttc      120
agcagatacc tcgtgaacta cacttcggtc gaaagtgtgg aagatattaa tgaggattgc      180
gcggaacttt atttcaacta cttgatggac aaccacaagc ggctcggcat caatctgacc      240
gacatcaagc ggtcaatgca gctgatagga gatattcttg atgtcgaggt caatcattac      300
ctgaaagatt tttctttgtc gaatgtgacg ctttggatga gccaggagaa a               351
```

<210> SEQ ID NO 11
<211> LENGTH: 672
<212> TYPE: DNA
<213> ORGANISM: Bacillus subtilis

<400> SEQUENCE: 11

```
atgaagattt acggagtata tatggaccgc ccgctttctg caggggaaga ggatcggatg       60
atggcggccg tgtccgccga aaagcgggaa aaatgccggc gcttttacca taaggaggat      120
gctcaccgca ccttgatcgg cgacatgctg atccgcaccg ctgcggcgaa ggcttacgga      180
cttgatccgg ccgggatttc attcggcgtc caggaatacg gaaagccgta catccccgcg      240
cttccggaca tgcactttaa catttcccac tccgggcgct ggatcgtgtg cgccgttgat      300
tcaaaaccga tcggcattga tattgaaaaa atgaagcccg gcacgattga tatcgccaaa      360
cggttttttt cgccgacgga atacagtgat ctgcaagcga acaccccga tcagcagacc       420 gattattttt accatctgtg gtcgatgaaa gaaagcttta tcaagcaggc cggaaaaggg      480
ctttccctgc cgcttgattc attcagcgtc cgccttaaag acgacggcca tgtgtccatt      540
gagctcccgg acgacatgaa ccttgtttc atccgcacat atgatgcgga cgaggagtat       600
aagctggccg tttgtgcggc gcatcccgat ttttgtgacg ggattgagat gaaaacgtat      660
gaaaagctgc tg                                                          672
```

<210> SEQ ID NO 12
<211> LENGTH: 1791
<212> TYPE: DNA
<213> ORGANISM: Bacillus subtilis

<400> SEQUENCE: 12

```
atgattttg cattggatac gtatctcgtt ttactttccg ttgttatagg atatcaattt        60
tttgaggatt cttatcactt ttatgactcc ggagcgttgc tgctgactgc cgtgagcatg      120
ttgatcagcc atcatgtatg cgcttttatg tttcaccagt ataagcaggt atggacgtac      180
acgggaatag gcgagctgct tgatctgctg aagggggatca cgctgtccgc agctgtgaca      240
```

| | |
|---|---|
| gccgccgtcc aataeggggt gttccacacg attttgttcc ggctgttggc cgtcagctgg | 300 |
| atggttcagc tattgttcat cggaggaagc cggatgattt cacgggtgct gaaagaaacg | 360 |
| atcggcagga agcaaaatga ctcttcccgg gcgctgatca tcggcgcagg tgcgggaggg | 420 |
| acgctgctcg tccgtcagct tacccagaaa acgatctcg gaatcatgcc tgtggctttt | 480 |
| attgatgatg atcagacaaa gcataagctt gaaatcatgg gcctgccgt catcggcgga | 540 |
| aaagaaagca ttatgccggc ggtgcagagg ctgagaattc accatatcat cattgccatt | 600 |
| ccgtctcttt gcacccatga gcttcagacg ttatacaaag aatgtgtgca gacgggcgcc | 660 |
| catattaaaa tcatgccgca atttgatgag atcctgctcg aacgcaggc tgccggacac | 720 |
| atcagagatg taaaagccga agatctgctc ggcagaaagc cggtcaccct tgatacgagc | 780 |
| aaaatttctg acagcatcaa gggaaaaacg attctggtca cgggcgccgg cggctcaatc | 840 |
| ggttctgaga tctgccgcca gatcagcgcg tttcttccgc gggaaatcgt ccttctcggc | 900 |
| cacggggaga acagcattca ttccgtacat accgagctgt ccgcacgctt cggcaaagag | 960 |
| gtgctctttc acgcggagat cgccgatatt caggacagag ataaaatctt tgctttgatg | 1020 |
| aaaaaatacg agccgcacgt cgtctatcat gcggctgccc ataaacatgt gccgttaatg | 1080 |
| gaacataatc cggaagaagc cgttaaaaac aacattatcg gcacgaaaaa tgtcgccgaa | 1140 |
| gccgccgaca tgtgcggaac ggaaacattc gtgctgattt cttctgacaa agcggtcaat | 1200 |
| ccggccaatg tcatgggcgc gacgaaacgg tttgcggaaa tggtcatcat gaacctcgga | 1260 |
| aaggtcagca gcaccaaatt cgccgccgtc cgtttcggaa atgtgctcgg aagccgcggc | 1320 |
| agcgtcattc cgattttcaa aaagcagatt gaaaaaggcg accccgtcac cgtcacgcac | 1380 |
| ccggcgatga caagatattt tatgacgatt cccgaagcgt caagactcgt cattcaggcg | 1440 |
| ggggcgcttg caaagggcg gcagattttc gttctggata tgggagaacc cgtcaaaatc | 1500 |
| gtcgatctgg ccaaaaacct gattcattta tcaggctata cgacagaaca gattcccatc | 1560 |
| gaattctccg gcatccgtcc gggagaaaag atgtatgaag aattgctgaa tcataatgaa | 1620 |
| gtacatacgg agcagatttt tccgaaaatc catatcggga aagcggtgga cgggaattgg | 1680 |
| gccgtactca tccgtttttat ggaggaattc agccgtctgc ctgaagaaga gctgagaaaa | 1740 |
| aggctgtttg aggcgatcga atcagtacat gaagaagcgg ccgcaggcgt g | 1791 |

<210> SEQ ID NO 13
<211> LENGTH: 138
<212> TYPE: DNA
<213> ORGANISM: Bacillus subtilis

<400> SEQUENCE: 13

| | |
|---|---|
| gtggaaaaca aattagaaga agtaaagcaa ttattattcc gacttgaaaa tgatatcaga | 60 |
| gaaacaaccg actcattacg aaacattaac aaaagcattg atcagctcga taaattctca | 120 |
| tatgcaatga aaatttct | 138 |

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14

| | |
|---|---|
| aaacaatgaa aaagccgtt ctgg | 24 |

```
<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tccgtgataa tcaaaaggcc                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aaagaatgat cttcagctac                                               20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
attaaaaaca gaccgaccgc                                               20

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
cataatgaat agaattgacc cg                                            22

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gaaacccagc ttgtctaaag                                               20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
aatgaaactt ttgcaagttg cc                                            22

<210> SEQ ID NO 21
<211> LENGTH: 20
<212> TYPE: DNA
<213> ORGANISM: Artificial Sequence
<220> FEATURE:
<223> OTHER INFORMATION: Primer
```

<400> SEQUENCE: 21
aatcgatatt ccgagtccac                                               20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
acgctktaya artggctsac                                               20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
tcatccakay cgtvacattd g                                             21

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24
aggaggaatt ctacggaagt gttaatttca tac                                33

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
tccatgctcg aggaagagc                                                19

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
acagaaagtc tcgagatcgt c                                             21

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
ctcctggatc tcaatggct ttttggaaat cag                                 33

<210> SEQ ID NO 28
<211> LENGTH: 352

<212> TYPE: DNA
<213> ORGANISM: Bacillus subtilis

<400> SEQUENCE: 28

```
ttgaagaggg caagtattgt gcgtgaaaaa aaatattat gaattagtgg aacaattaaa      60
agacagaaca caagacgtaa cattttcagc tacaaaagca ctaagtcttc ttatgctgtt    120
cagcagatat ttggtcaatt acaccaatgt cgaatcagta aatgacatta atgaggaatg    180
cgccaaacat tattttaact acttaatgaa aaaccataag cgattaggaa ttaatctgac    240
agatataaaa aggtcgatgc atctaatcag cgggttattg gatgtggatg taaaccacta    300
tttaaaggat ttttcactat cgaatgtcac gctgtggatg acgcaagaga ga            352
```

<210> SEQ ID NO 29
<211> LENGTH: 299
<212> TYPE: DNA
<213> ORGANISM: Bacillus subtilis

<400> SEQUENCE: 29

```
ttgaagaggg caagtattgt gcgtgaaaaa aaatattatg aattagtgga caactaaaa      60
gacagaacaa aagacgtcac attttcatca acaaaagcac taagtcttct tatgctgttc    120
agcagatacc tggtcaatta cacaaatgtt gaatgcgttc acgaaatcaa tgaagagtgt    180
gcgaagcatt atttcactta cttaatgaaa accataaac gtttaggaat taatctgacg    240
gatattaagc ggtccatgct tctgatcagc ggcgtgatcg aggtggaggt tgaccacta    299
```

<210> SEQ ID NO 30
<211> LENGTH: 299
<212> TYPE: DNA
<213> ORGANISM: Bacillus subtilis

<400> SEQUENCE: 30

```
ttcaagaggg caagtattgt gcgtgaaaaa aaatattatg aattagtgga caactaaaa      60
gacagaacaa aagacgtcac attttcatca acaaaagcac taagtcttct tatgctgttc    120
agcagatacc tggtcaatta cacaaatgtt gaatgcgttc acgaaatcaa tgaagagtgt    180
gcgaagcatt atttcactta cttaatgaaa accataaac gtttaggaat taatctgacg    240
gatattaagc ggtccatgct tctgatcagc ggcgtgatcg aggtggaggt tgaccacta    299
```

<210> SEQ ID NO 31
<211> LENGTH: 298
<212> TYPE: DNA
<213> ORGANISM: Bacillus subtilis

<400> SEQUENCE: 31

```
ttgaagaggg caagtattgt gcgtgaaaaa aatattatga attagtggaa caactaaaag      60
acagaacaaa agacgtcaca ttttcatcaa caaaagcact aagtcttctt atgctgttca    120
gcagataccc ggtcaattac acaaatgttg aatgcgttca cgaaatcaat gaagagtgtg    180
cgaagcatta tttcacttac ttaatgaaaa accataaacg tttaggaatt aatctgacgg    240
atattaagcg gtccatgctt ctgatcagcg gcgtgatcga ggtggaggtt gaccacta     298
```

<210> SEQ ID NO 32
<211> LENGTH: 299
<212> TYPE: DNA
<213> ORGANISM: Bacillus amyloliquefaciens

<400> SEQUENCE: 32

```
ttgaagaggg caagtattgt gcgtgaaaaa aaatattatg aattagtgga acaactaaaa    60
gaccgaacaa aagacgttac attttcatca acaaaagcac taagtcttct tatgctgttc   120
agcagatacc tggtcaatta cacaaatgtt gaatgtgttc acgatatcaa tgaggagtgt   180
gcaaagcatt atttcaccta cttaatgaaa accataaaac gtttaggaat caatctgacg   240
gatattaaac ggtccatgct tttgatcagc ggtgtaatcg aggtggaagt cgaccacta    299
```

<210> SEQ ID NO 33
<211> LENGTH: 299
<212> TYPE: DNA
<213> ORGANISM: Bacillus subtilis

<400> SEQUENCE: 33

```
ttgaagaggg caagtattgt gcgtgaaaaa aaatattatg aattagtgga acaattaaaa    60
gacagaacac aagacgtaac attttcagct acaaaagcac taagtcttct tatgctgttc   120
agcagatatt tggtcaatta caccaatgtc gaatcagtaa atgacattaa tgaggaatgc   180
gccaaacatt atttttaacta cttaatgaaa accataagc gattaggaat taatctgaca   240
gatataaaaa ggtcgatgca tctaatcagc gggttattgg atgtggatgt aaaccacta    299
```

<210> SEQ ID NO 34
<211> LENGTH: 300
<212> TYPE: DNA
<213> ORGANISM: Bacillus subtilis

<400> SEQUENCE: 34

```
ttgaagaggg caagtattgt gcgtgaaaaa aaaatattat gaattagtgg aacaattaaa    60
agacagaaca caagacgtaa cattttcagc tacaaaagca ctaagtcttc ttatgctgtt   120
cagcagatat ttggtcaatt acaccaatgt cgaatcagta atgacattaa tgaggaatg   180 cgccaaacat tattttaact acttaatgaa aaccataag cgattaggaa ttaatctgac   240
agatataaaa aggtcgatgc atctaatcag cgggttattg gatgtggatg taaaccacta   300
```

<210> SEQ ID NO 35
<211> LENGTH: 299
<212> TYPE: DNA
<213> ORGANISM: Bacillus atrophaeus

<400> SEQUENCE: 35

```
ttgaagaggg caagtattgt gcgtgaaaaa aaatactatg aattagtgga acaattaaaa    60
gaccgaacac aagacgtaac attttcagct acaaaagcac taagtcttct aatgctcttt   120
agcagatatt tagtcaatta cacaaatgta gaatcagtga acgatattaa tgaggaatgc   180
gccgagcatt attttaatta tttaatgaaa aatcataaac ggttgggaat caatctgaca   240
gacataaaac gatcaatgct cctcatcggc ggtgtgttgg acgtcgaggt aaaccatta    299
```

<210> SEQ ID NO 36
<211> LENGTH: 299
<212> TYPE: DNA
<213> ORGANISM: Bacillus pumilus

<400> SEQUENCE: 36

```
ttgaaaaggg caagtattgt gagagagaaa aaatattacg agttggtaga ggagcttaag    60
agtcgtacga aagatgtgac gttttccgct acaaaggcat taagtctgct catgctgtta   120
agcaggtact tggtcaatta cacaacggta gaatcagtcg acgaaataga tgaagactgt   180
gctgagatat acttcaatta tttaatggat aatcataaga gacttggtat aaacttaacc   240
```

```
gacatcaaga gatcgatgca gctgcttggc ggcatactag atgtagatgt caatcacta      299
```

<210> SEQ ID NO 37
<211> LENGTH: 299
<212> TYPE: DNA
<213> ORGANISM: Bacillus pumilus

<400> SEQUENCE: 37

```
ttgaaaaggg caagtattgt gagagagaaa aaatattacg agttggtaga ggagcttaag       60
agtcgtacga aagatgtgac gttttcggct acaaaggcat taagtctact catgctgtta      120
agcaggtact tggtcaatta cacaacggta gaatcagtcg acgagatcga tgaagactgt      180
gctgagatat acttcaatta tttaatggat aatcataaga gacttggtat aaacttaacc      240
gacatcaaga ggtccatgca gcttctcggc ggcatactag atgtagatgt gaatcacta      299
```

<210> SEQ ID NO 38
<211> LENGTH: 117
<212> TYPE: PRT
<213> ORGANISM: Bacillus amyloliquefaciens

<400> SEQUENCE: 38

```
Met Lys Arg Ala Ser Ile Val Arg Glu Lys Lys Tyr Tyr Glu Leu Val
1               5                  10                  15

Glu Gln Leu Lys Asp Arg Thr Lys Asp Val Thr Phe Ser Ser Thr Lys
            20                  25                  30

Ala Leu Ser Leu Leu Met Leu Phe Ser Arg Tyr Leu Val Asn Tyr Thr
        35                  40                  45

Asn Val Glu Cys Val His Asp Ile Asn Glu Glu Cys Ala Lys His Tyr
    50                  55                  60

Phe Thr Tyr Leu Met Lys Asn His Lys Arg Leu Gly Ile Asn Leu Thr
65                  70                  75                  80

Asp Ile Lys Arg Ser Met Leu Leu Ile Ser Gly Val Ile Glu Val Glu
                85                  90                  95

Val Asp His Tyr Leu Lys Asp Phe Ser Leu Ser Asn Val Thr Leu Trp
            100                 105                 110

Met Thr Glu Glu Arg
        115
```

<210> SEQ ID NO 39
<211> LENGTH: 117
<212> TYPE: PRT
<213> ORGANISM: Bacillus subtilis
<220> FEATURE:
<221> NAME/KEY: misc_feature
<222> LOCATION: (115)..(115)
<223> OTHER INFORMATION: Xaa can be any naturally occurring amino acid

<400> SEQUENCE: 39

```
Met Lys Arg Ala Ser Ile Val Arg Glu Lys Lys Tyr Tyr Glu Leu Val
1               5                  10                  15

Glu Gln Leu Lys Asp Arg Thr Gln Asp Val Thr Phe Ser Ala Thr Lys
            20                  25                  30

Ala Leu Ser Leu Leu Met Leu Phe Ser Arg Tyr Leu Val Asn Tyr Thr
        35                  40                  45

Asn Val Glu Ser Val Asn Asp Ile Asn Glu Glu Cys Ala Lys His Tyr
    50                  55                  60

Phe Asn Tyr Leu Met Lys Asn His Lys Arg Leu Gly Ile Asn Leu Thr
65                  70                  75                  80
```

```
Asp Ile Lys Arg Ser Met His Leu Ile Ser Gly Leu Leu Asp Val Asp
                 85                  90                  95

Val Asn His Tyr Leu Lys Asp Phe Ser Leu Ser Asn Val Thr Leu Trp
            100                 105                 110

Met Thr Xaa Glu Arg
        115

<210> SEQ ID NO 40
<211> LENGTH: 117
<212> TYPE: PRT
<213> ORGANISM: Bacillus atrophaeus

<400> SEQUENCE: 40

Met Lys Arg Ala Ser Ile Val Arg Glu Lys Lys Tyr Tyr Glu Leu Val
1               5                   10                  15

Glu Gln Leu Lys Asp Arg Thr Gln Asp Val Thr Phe Ser Ala Thr Lys
            20                  25                  30

Ala Leu Ser Leu Leu Met Leu Phe Ser Arg Tyr Leu Val Asn Tyr Thr
        35                  40                  45

Asn Val Glu Ser Val Asn Asp Ile Asn Glu Glu Cys Ala Glu His Tyr
50                  55                  60

Phe Asn Tyr Leu Met Lys Asn His Lys Arg Leu Gly Ile Asn Leu Thr
65                  70                  75                  80

Asp Ile Lys Arg Ser Met Leu Leu Ile Gly Gly Val Leu Asp Val Glu
                85                  90                  95

Val Asn His Tyr Leu Lys Asp Phe Ser Leu Ser Asn Val Thr Leu Trp
            100                 105                 110

Met Asn Gln Glu Arg
        115

<210> SEQ ID NO 41
<211> LENGTH: 117
<212> TYPE: PRT
<213> ORGANISM: Bacillus pumilus

<400> SEQUENCE: 41

Met Lys Arg Ala Ser Ile Val Arg Glu Lys Lys Tyr Tyr Glu Leu Val
1               5                   10                  15

Glu Glu Leu Lys Ser Arg Thr Lys Asp Val Thr Phe Ser Ala Thr Lys
            20                  25                  30

Ala Leu Ser Leu Leu Met Leu Leu Ser Arg Tyr Leu Val Asn Tyr Thr
        35                  40                  45

Thr Val Glu Ser Val Asp Glu Ile Asp Glu Asp Cys Ala Glu Ile Tyr
50                  55                  60

Phe Asn Tyr Leu Met Asp Asn His Lys Arg Leu Gly Ile Asn Leu Thr
65                  70                  75                  80

Asp Ile Lys Arg Ser Met Gln Leu Leu Gly Gly Ile Leu Asp Val Asp
                85                  90                  95

Val Asn His Tyr Leu Lys Asp Phe Ser Leu Ser Asn Val Thr Leu Trp
            100                 105                 110

Met Asn Gln Glu Lys
        115

<210> SEQ ID NO 42
<211> LENGTH: 117
<212> TYPE: PRT
<213> ORGANISM: Bacillus pumilus
```

```
<400> SEQUENCE: 42

Met Lys Arg Ala Ser Ile Val Arg Glu Lys Lys Tyr Tyr Glu Leu Val
1               5                   10                  15

Glu Glu Leu Lys Ser Arg Ser Lys Asp Val Thr Phe Ser Ala Thr Lys
                20                  25                  30

Ala Leu Ser Leu Leu Met Leu Leu Ser Arg Tyr Leu Val Asn Tyr Thr
                35                  40                  45

Thr Val Glu Ser Val Asp Glu Ile Asp Glu Asp Cys Ala Glu Ile Tyr
        50                  55                  60

Phe Asn Tyr Leu Met Asp Asn His Lys Arg Leu Gly Ile Asn Leu Thr
65                  70                  75                  80

Asp Ile Lys Arg Ser Met Gln Leu Leu Gly Gly Ile Leu Asp Val Asp
                85                  90                  95

Val Asn His Tyr Leu Lys Asp Phe Ser Leu Ser Asn Val Thr Leu Trp
                100                 105                 110

Met Asn Gln Glu Lys
        115

<210> SEQ ID NO 43
<211> LENGTH: 117
<212> TYPE: PRT
<213> ORGANISM: Bacillus licheniformis

<400> SEQUENCE: 43

Met Lys Arg Ala Ser Ile Val Arg Glu Lys Lys Tyr Tyr Glu Leu Val
1               5                   10                  15

Glu Gln Leu Lys Val Arg Ser Gln Asp Val Thr Phe Ser Ala Thr Lys
                20                  25                  30

Ala Val Gly Leu Leu Met Leu Phe Ser Arg Tyr Leu Val Asn Tyr Thr
                35                  40                  45

Ser Val Glu Ser Val Glu Asp Ile Asn Glu Asp Cys Ala Glu Leu Tyr
        50                  55                  60

Phe Asn Tyr Leu Met Asp Asn His Lys Arg Leu Gly Ile Asn Leu Thr
65                  70                  75                  80

Asp Ile Lys Arg Ser Met Gln Leu Ile Gly Asp Ile Leu Asp Val Glu
                85                  90                  95

Val Asn His Tyr Leu Lys Asp Phe Ser Leu Ser Asn Val Thr Leu Trp
                100                 105                 110

Met Ser Gln Glu Lys
        115
```